United States Patent
Werthmann et al.

(10) Patent No.: US 11,306,086 B2
(45) Date of Patent: Apr. 19, 2022

(54) CRYSTALLINE SALTS OF A B-RAF KINASE INHIBITOR

(71) Applicant: Xynomic Pharmaceuticals, Inc., Dover, DE (US)

(72) Inventors: Ulrike Werthmann, Ingelheim am Rhein (DE); Gerd-Michael Maier, Ingelheim am Rhein (DE); Bodo Betzemeier, Ingelheim am Rhein (DE); Otmar Schaaf, Ingelheim am Rhein (DE)

(73) Assignee: Xynomic Pharmaceuticals, Inc., Dover, DE (US)

( * ) Notice: Subject to any disclaimer, the term of this patent is extended or adjusted under 35 U.S.C. 154(b) by 45 days.

(21) Appl. No.: 16/759,187

(22) PCT Filed: Oct. 26, 2018

(86) PCT No.: PCT/US2018/057792
§ 371 (c)(1),
(2) Date: Apr. 24, 2020

(87) PCT Pub. No.: WO2019/084459
PCT Pub. Date: May 2, 2019

(65) Prior Publication Data
US 2020/0283433 A1 Sep. 10, 2020

Related U.S. Application Data

(60) Provisional application No. 62/577,313, filed on Oct. 26, 2017.

(51) Int. Cl.
*C07D 471/04* (2006.01)
(52) U.S. Cl.
CPC ........ *C07D 471/04* (2013.01); *C07B 2200/13* (2013.01)
(58) Field of Classification Search
CPC .................................................. C07D 471/04
USPC ....................................................... 514/256
See application file for complete search history.

(56) References Cited

U.S. PATENT DOCUMENTS 8,889,684 B2 * 11/2014 Stadtmueller ........ C07D 471/04
514/249

FOREIGN PATENT DOCUMENTS

| WO | WO 2002/000196 | 6/2002 |
| WO | WO 2010/042337 | 4/2010 |
| WO | WO 2012/104388 | 8/2012 |

OTHER PUBLICATIONS

[No Author Listed], "COSMIC v53 Release", Catalogue of Somatic Mutations in Cancer, Wellcome Trust Sanger Institute, May 2011, 6 pages.
Bollag et al., "Clinical efficacy of a RAF inhibitor needs broad target blockade in BRAF-mutant melanoma," Nature, 2010, 467(7315):596-9.
Chapman et al. "Improved Survival with Vemurafenib in Melanoma with Braf V600E Mutation", New Engl. J Med, 2011, 364:2507-2516.
Flaherty et al., "Inhibition of Mutated, Activated BRAF in Metastatic Melanoma," New Engl. J Med., 2010, 363:809-819.
Hoeflich et al., "Oncogenic BRAF is required for tumor growth and maintenance in melanoma models," Cancer Res., 2006, 66:999-1006.
Karasarides et al., "B-RAF is a therapeutic target in melanoma," Oncogene, 2004, 23:6292-6298.
PCT International Preliminary Report on Patentability in International Appln. No. PCT/US2018/057792, dated Apr. 28, 2020, 7 pages.
PCT International Search Report and Written Opinion in International Appln. No. PCT/US2018/057792, dated Jan. 3, 2019, 9 pages.
Rubinstein et al., "Incidence of the V600K mutation among melanoma patients with BRAF mutations, and potential therapeutic response to the specific BRAF inhibitor PLX4032," J Transl. Med., 2010, 8:67.
Tsai et al., "Discovery of a selective inhibitor of oncogenic B-Raf kinase with potent antimelanoma activity," Proc. Natl. Acad. Science., 2008, 105:3041-3046.
Waizenegger et al., "A Novel RAF Kinase Inhibitor with DFG-Out-Binding Mode: High Efficacy in BRAF-Mutant Tumor Xenograft Models in the Absence of Normal Tissue Hyperproliferation," Mal. Cancer Ther., 2016, 15(3):354-65.
Wan et al., "Mechanism of activation of the RAF-ERK signaling pathway by oncogenic mutations of BRAF," Cell, 2004, 116:855-867.
Wellbrock et al., "The RAF proteins take centre stage," Nature Rev. Mal. Cell Biol., 2004, 5:875-885.
Wellbrock et al., "V599EB-RAF is an oncogene in melanocytes," Cancer Res., 2004, 64:2338-2342.
Office Action in Indian Appln. No. 202017021378, dated Nov. 9, 2021, 6 pages.

* cited by examiner

*Primary Examiner* — Niloofar Rahmani
(74) *Attorney, Agent, or Firm* — Fish & Richardson P.C.

(57) ABSTRACT

The present invention is related to crystalline salts of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide, a RAF kinase Inhibitor, useful in the treatment of cancer and other diseases.

20 Claims, 40 Drawing Sheets

Sample: BI00882370SC_PR1BIR05283PA1  File: BI00882370SC_PR1BIR05283PA1_AUS_ETOH
Size: 2.3300 mg  Operator: R. Dukeck
Method: Eq20°C 10K-250   DSC   Run Date: 12-Dec-2011 10:47
Comment: aus EtOH 96%  Instrument: DSC Q2000 V24.8 Build 120

Sample: BI00882370SC_PR1BIR05283PA1  File: BI00882370SC_PR1BIR05283PA1_AUS_ETO
Size: 4.7470 mg  Run Date: 12-Dec-2011 10:48
Method: 10k-250°C   TGA   Instrument: TGA Q5000 V3.13 Build 261
Comment: aus EtOH 96%

CRYSTALLINE SALTS OF A B-RAF KINASE INHIBITOR

CROSS-REFERENCE TO RELATED APPLICATIONS

This application is the national stage entry of International Patent Application No. PCT/US2018/057792, filed Oct. 26, 2018, and claims the benefit of U.S. Provisional Application No. 62/577,313, filed Oct. 26, 2017, the entire disclosure of which is incorporated herein by reference.

FIELD

The present disclosure is related salt forms, and, in particular, crystalline salts of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide (BI 882370), a RAF kinase Inhibitor, useful in the treatment of cancer and other diseases.

BACKGROUND

The compound N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide (BI 882370), having Formula I:

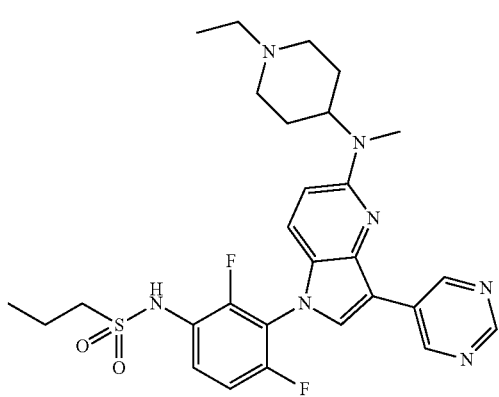

is a RAF kinase inhibitor useful in the treatment of various diseases including cancer. The compound of Formula I, as well as its preparation and use, have been described in WO/2012/104388, which is incorporated herein by reference in its entirety.

The RAS-RAF-MAPK (mitogen-activated protein kinase) signaling pathway plays a critical role in transmitting proliferation signals generated by the cell surface receptors and cytoplasmic signaling elements to the nucleus. Constitutive activation of this pathway is involved in malignant transformation by several oncogenes. Activating mutations in RAS occur in approximately 15% of cancers, and recent data has shown that B-RAF is mutated in about 7% of cancers (Wellbrock et al., "The RAF proteins take centre stage", *Nature Rev. Mol. Cell Biol.*, 2004, 5, 875-885), identifying it as another important oncogene in this pathway. In mammals, the RAF family of serine/threonine kinases comprises three members: A-RAF, B-RAF and C-RAF. However, activating mutations have so far been only identified in B-RAF underlining the importance of this isoform. It is believed that B-RAF is the main isoform that couples RAS to MEK, and that C-RAF and A-RAF signal to ERK only to fine-tune cellular responses (Wellbrock et al. *Nature Rev. Mol. Cell Biol.*, 2004, 5, 875-885). The most common cancer mutation in B-RAF results in a valine to glutamic acid exchange at position 600 of the protein (V600E), which dramatically enhances B-RAF activity, presumably because its negative charge mimics activation loop phosphorylation (Wan et al., "Mechanism of activation of the RAF-ERK signaling pathway by oncogenic mutations of B-RAF", *Cell*, 2004, 116, 855-867). The highest incidence of B-RAF V600 mutations occurs in malignant melanoma (39%), thyroid cancer (46%), colorectal cancer (10%), biliary tract cancer (10%), prostate cancer (4%), ovary cancer (3%) and non-small cell lung cancer (2%), but they also occur at a low frequency in a wide variety of other cancers (frequencies of mutations according to COSMIC (Catalogue Of Somatic Mutations In Cancer; Wellcome Trust Sanger Institute) release v.53, 15 May 2011; http://www.sanger.ac.uk/genetics/CGP/cosmic/). Literature supported the hypothesis that B-RAF$^{V600E}$ mutated tumor cells seem to rely heavily on the continued activation of this pathway—a phenomenon termed "oncogene addiction"—whereas normal B-RAF$^{wt}$ cells use a broader range of signals. This provides an Achilles' heel that can be exploited therapeutically by treating patients with somatically mutated B-RAF$^{V600E}$ using orally available B-RAF inhibitors.

The key role of B-RAF$^{V600E}$ in aberrant ERK signaling and consequently oncogenesis has been demonstrated in several independent experimental approaches such as over-expression of oncogenic/mutated B-RAF in vitro and in vivo (Wan et al., *Cell*, 2004, 116, 855-867; Wellbrock et al., *Cancer Res.* 2004, 64: 2338-2342), siRNA knock-down in vitro (Karasarides et al., Oncogene, "V599EB-RAF is an oncogene in melanocytes", 2004, 23, 6292-6298) or in inducible short-hairpin RNA xenograft models where gain-of-function B-RAF signaling was found to be strongly associated with in vivo tumorigenicity (Hoeflich et al., "Oncogenic BRAF is required for tumor growth and maintenance in melanoma models", *Cancer Res.*, 2006, 66, 999-1006).

Treatment of B-RAFv$^{600E}$ mutated melanoma or colon carcinoma cells induces a B-RAF inhibition phenotype (e.g. reduction of phospho-MEK and phospho-ERK levels, reduction of cyclin D expression and induction of p27 expression). Consequently, these cells are locked in the Gi-phase of the cell cycle and do not proliferate.

Clinical proof of mechanism and proof of concept has been established for treating in cancer in B-RAFv$^{600E}$ mutated melanoma patients treated with Zelboraf®, B-RAF inhibitor (PLX-4032, vemurafenib, from Plexxikon/Daiichi Sankyo/Roche. Bollag et al., "Clinical efficacy of a RAF inhibitor needs broad target blockade in BRAF-mutant melanoma", *Nature*, 2010, 467(7315), 596-9; Flaherty et al., *New Engl. J. Med.*, "Inhibition of Mutated, Activated BRAF in Metastatic Melanoma", 2010, 363, 809-819; Chapman et al. "Improved Survival with Vemurafenib in Melanoma with BRAF V600E Mutation", *New Engl. J. Med*, 2011, 364: 2507-2516. Favorable response rates were observed in both Phase I and Phase III clinical trials. It was reported, that melanoma patients carrying a B-RAFv$^{600K}$ mutation also do respond to therapy (Rubinstein et al., "Incidence of the V600K mutation among melanoma patients with BRAF mutations, and potential therapeutic response to the specific BRAF inhibitor PLX4032", *J Transl. Med.*, 2010, 8, 67).

The most frequent B-RAF mutation is the exchange at amino acid position 600 from valine to glutamate with more than 90% frequency of all B-RAF mutations (Wellbrock et al. *Nature Rev. Mol. Cell Biol.*, 2004, 5, 875-885), the second most frequent mutation is an alteration from valine to lysine, other mutations were found with lower frequency at that position (Wellbrock et al. *Nature Rev. Mol. Cell Biol.*, 2004, 5, 875-885 and frequencies of mutations according to COSMIC (Catalogue Of Somatic Mutations In Cancer; Wellcome Trust Sanger Institute) release v53, 15 May 2011; http://www.sanger.ac.uk/genetics/CGP/cosmic/). Additional mutations were found at e.g. the glycine rich loop (Wellbrock et al. *Nature Rev. Mol. Cell Biol.*, 2004, 5, 875-885). Not all of these rather rare mutations seem to lead to direct activation of B-RAF (Wan et al., "Mechanism of activation of the RAF-ERK signaling pathway by oncogenic mutations of B-RAF", *Cell*, 2004, 116, 855-867).

The compound of Formula I is a highly potent and selective RAF inhibitor that binds to the DFG-out (inactive) conformation of the B-RAF kinase. The compound inhibited proliferation of human B-RAF-mutant melanoma cells with 100 times higher potency (1-10 nmol/L) than vemurafenib, whereas wild-type cells were not affected at 1,000 nmol/L. A solution of the compound administered orally was efficacious in mouse models of B-RAF-mutant melanomas and colorectal carcinomas, and at 25 mg/kg twice daily showed superior efficacy compared with vemurafenib, dabrafenib, or trametinib. The compound was also active in A375 melanoma-bearing mice that were resistant to vemurafenib, particularly when dosed in combination with trametinib. Mice treated with the compound did not show any body weight loss or clinical signs of intolerability, and no pathologic changes were observed in several major organs investigated, including skin. Furthermore, in a pilot study in rats (up to 60 mg/kg daily for 2 weeks), the compound lacked toxicity in terms of clinical chemistry, hematology, pathology, and toxicogenomics. These results are described in Waizenegger et al., *Mol. Cancer Ther.*, 2016, 15(3); 354-65, which is incorporated herein by reference in its entirety.

For the manufacture, purification, and formulation of a drug, it may be advantageous to employ a form of the drug having superior stability or other desirable formulation property exhibited by, for example, one or more salt or crystalline forms of the drug. Formation of salts of basic or acidic drugs can sometimes provide forms of the drug that have advantageous properties such as solubility, non-hygroscopicity, crystallinity, and other physical properties that advantageous for formulating the drug. On the other hand, discovering a suitable salt or other crystalline form that is suitable for formulation is difficult, since there are numerous variables in the formation of a salt or crystalline form. These include the existence of numerous possible acids and bases that might be used as a counter-ion, various stoichiometric ratios that may be possible for combining a given basic or acid drug with an acid or base counter-ion, a wide variety of solvents and solvent systems (including combinations of solvents) that potentially can be used to attempt to form salts or crystalline forms, and a variety of conditions (such as temperature or heating or cooling conditions) under which salts or crystalline forms may be generated. All of these variables of which may affect the properties of the salts or crystalline forms that might be obtained. Salts or solid forms may also have a variety of properties that render them unsuitable for drug development and formulation such as lack of crystallinity (amorphous forms), the presence or formation of multiple crystalline forms, which may interconvert and/or have different properties (polymorphism), lack of aqueous solubility, hygroscopicity, or stickiness of the solid. Furthermore, the formation of salts and crystalline forms and their properties are generally very unpredictable.

Accordingly, the crystalline salt forms of the compound of Formula I provided herein help satisfy the ongoing need for the development of a RAF kinase inhibitor for the treatment of serious diseases.

SUMMARY

The present disclosure provides a crystalline N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt and particular crystalline forms of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt.

In some embodiments, the crystalline salt is substantially anhydrous.

In some embodiments, the crystalline salt is substantially non-solvated.

In some embodiments, the crystalline salt is Form A of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt.

In some embodiments, the crystalline salt has an X-ray powder diffraction pattern comprising at least one of the following peaks, in terms of 2θ: 15.4°±0.5°; 20.0°±0.5°; and 21.8°±0.5°. In some embodiments, the peak at 15.4°±0.5°; 20.0°±0.5°; 21.8°±0.5° is the peak of the highest relative intensity in the X-ray powder diffraction pattern.

In some embodiments, the crystalline salt has an X-ray powder diffraction pattern comprising at least one of the following peaks, in terms of 2θ: 15.4°±0.2°; 20.0°±0.2°; and 21.8°±0.2°. In some embodiments, the peak at 15.4°±0.2°; 20.0°±0.2°; or 21.8°±0.2° is the peak of the highest relative intensity in the X-ray powder diffraction pattern.

In some embodiments, the crystalline salt has an X-ray powder diffraction pattern comprising at least one peak, in terms of 2θ, at 15.4°±0.5°. In some embodiments, the peak at 15.4°±0.5° is the peak of the highest relative intensity in the X-ray powder diffraction pattern.

In some embodiments, the crystalline salt has an X-ray powder diffraction pattern comprising at least one peak, in terms of 2θ, at 15.4°±0.2°. In some embodiments, the peak at 15.4°±0.2° is the peak of the highest relative intensity in the X-ray powder diffraction pattern.

In some embodiments, the crystalline salt has an X-ray powder diffraction pattern comprising the following peaks, in terms of 2θ: 15.4°±0.5°; 20.0°±0.5°; and 21.8°±0.5°. In some embodiments, the peak at 15.4°±0.5°; 20.0°±0.5°; 21.8°±0.5°, is the peak of the highest relative intensity in the X-ray powder diffraction pattern.

In some embodiments, the crystalline salt has an X-ray powder diffraction pattern comprising the following peaks, in terms of 2θ: 15.4°±0.2°; 20.0°±0.2°; and 21.8°±0.2°. In some embodiments, the peak at 15.4°±0.2°; 20.0°±0.2°; or 21.8°±0.2° is the peak of the highest relative intensity in the X-ray powder diffraction pattern.

In some embodiments, the crystalline salt has an X-ray powder diffraction pattern substantially as shown in FIG. 10, FIG. 26, or FIG. 38.

In some embodiments, the crystalline salt has a differential scanning calorimetry thermogram (DSC) substantially as shown in FIG. 11, FIG. 27, or FIG. 39.

In some embodiments, the crystalline salt has a thermogravimetric analysis (TGA) substantially as shown in FIG. 12, FIG. 28 or FIG. 39.

In some embodiments, the crystalline salt is substantially isolated.

The present disclosure provides a composition (e.g., a pharmaceutical composition) comprising the crystalline N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt, or any of the embodiments thereof. The composition may include at least one pharmaceutically acceptable carrier.

The present disclosure provides a dosage form comprising the crystalline salt N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt, or any of the embodiments thereof, or the composition comprising the crystalline salt, or any of the embodiments thereof. The dosage form may be in the form of a tablet.

The present disclosure provides a method for preparing crystalline N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt. The method includes reacting N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide with one equivalent of succinic acid. The method can include crystallizing or recrystallizing the salt from a $C_{1-4}$ alcohol, aqueous $C_{1-4}$ alcohol or ethyl acetate. The method can include crystallizing or recrystallizing the salt from ethanol, isopropanol, aqueous ethanol or aqueous isopropanol, or ethyl acetate.

The present disclosure provides a method of treating a disease in a patient, wherein the disease is associated with abnormal expression or activity of a RAF kinase, comprising administering to the patient a therapeutically effective amount of crystalline N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt, or any of the embodiments thereof, or a composition comprising the crystalline N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt. The present disclosure also provides crystalline N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt, or any of the embodiments thereof, for use in treating a disease associated with abnormal expression or activity of a RAF kinase. Also provided is the use of crystalline N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt, or any of the embodiments thereof, for treating a disease associated with abnormal expression or activity of a RAF kinase. Also provided is the use of crystalline N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt, or any of the embodiments thereof, in the manufacture of a medicament for treating a disease associated with abnormal expression or activity of a RAF kinase.

In some embodiments, the disease is associated with abnormal expression or activity of a B-RAF kinase. In some embodiments, the B-RAF-kinase is a mutated B-RAF kinase. In some embodiments, the B-RAF-kinase is a V600E mutated B-RAF kinase. In some embodiments, the disease is selected from cancer, infections, inflammation and autoimmune diseases.

The present disclosure further provides a method of treating a cancer, comprising administering to the patient a therapeutically effective amount of crystalline N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt, or any of the embodiments thereof, or a composition comprising the crystalline N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt. The present disclosure also provides crystalline N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt, or any of the embodiments thereof, for use in treating cancer. Also provided is the use of crystalline N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt, or any of the embodiments thereof, for treating cancer. Also provided is the use of crystalline N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt, or any of the embodiments thereof, in the manufacture of a medicament for treating cancer.

In some embodiments, the cancer is breast, prostate, colon, endometrial, brain, bladder, skin, uterus, ovary, lung, pancreatic, renal, gastric, or a hematological cancer. In some embodiments, the cancer is malignant melanoma, thyroid cancer, colorectal cancer, biliary tract cancer, prostate cancer, ovary cancer or non-small cell lung cancer In some embodiments, the cancer is associated with expression or activity of a RAF kinase. In some embodiments, the cancer is associated with expression or activity of a B-RAF kinase. In some embodiments, the B-RAF-kinase is a mutated B-RAF kinase. In some embodiments, the B-RAF-kinase is a V600E mutated B-RAF kinase. In some embodiments, the cancer is melanoma. In some embodiments, the cancer is colorectal cancer. In some embodiments, the cancer is colon cancer. In some embodiments, the cancer is thyroid cancer. In some embodiments, the cancer expresses a mutated B-RAF kinase. In some embodiments, the cancer expresses a V600E mutated B-RAF kinase.

DETAILED DESCRIPTION

I. Definitions

Figure 1:
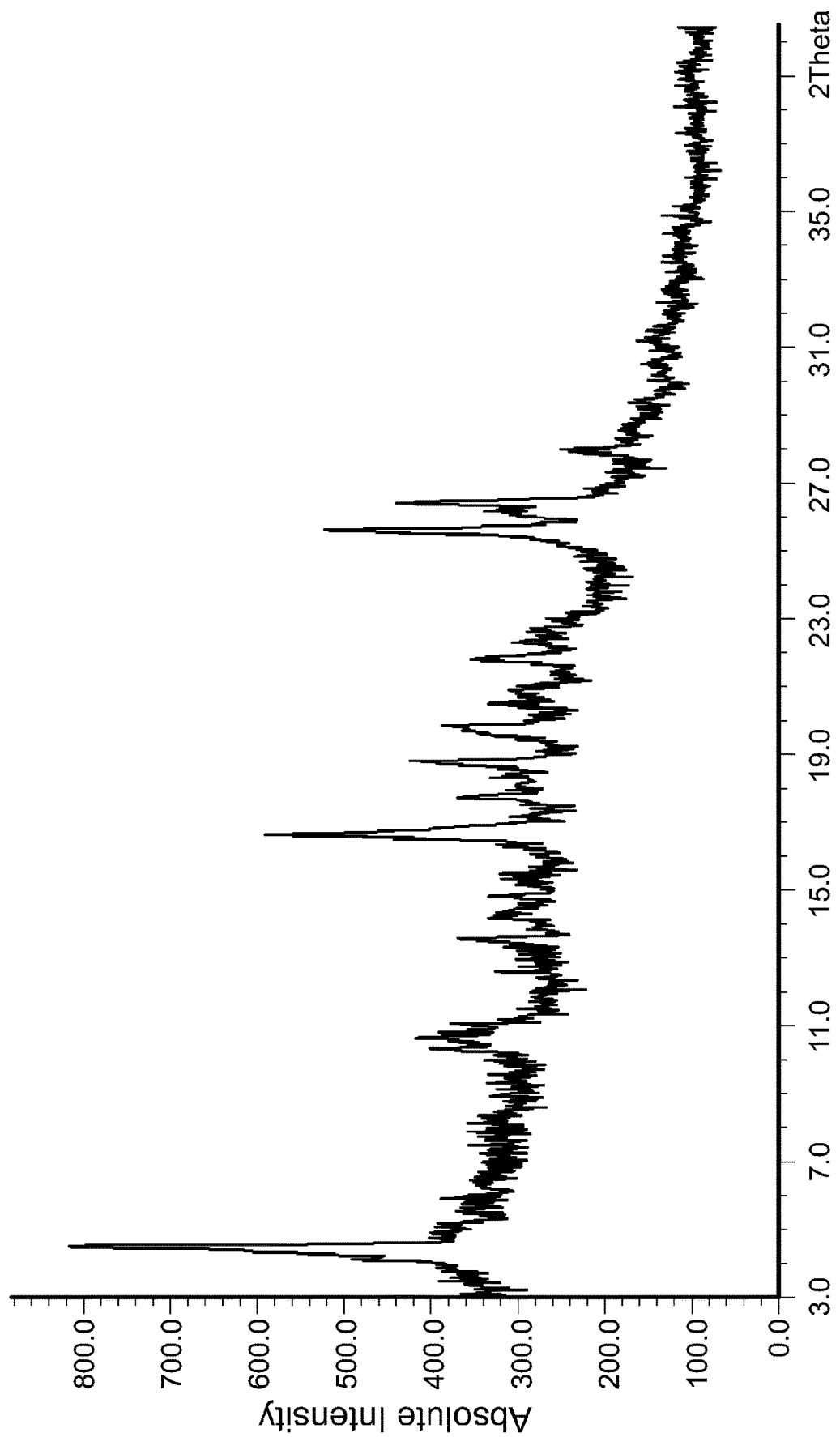
FIG. 1 is an XRPD of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide free base.

Unless defined otherwise, all technical and scientific terms used herein have the same meaning as is commonly understood by one of ordinary skill in the art to which this disclosure belongs.

For the terms "e.g." and "such as," and grammatical equivalents thereof, the phrase "and without limitation" is understood to follow unless explicitly stated otherwise.

As used herein, the singular forms "a," "an," and "the" include plural referents unless the context clearly dictates otherwise.

As used herein, the term "about" means "approximately" (e.g., plus or minus approximately 10% of the indicated value).

At various places in the present specification, certain features may be disclosed in groups or in ranges. It is specifically intended that such a disclosure include each and every individual sub-combination of the members of such groups and ranges. For example, the term "$C_{1-4}$ alkyl" is specifically intended to individually disclose (without limitation) methyl, ethyl, $C_3$ alkyl, and $C_4$ alkyl.

The term "individual", "subject" or "patient," used interchangeably, refers to any animal, including mammals, preferably mice, rats, other rodents, rabbits, dogs, cats, swine, cattle, sheep, horses, or primates, and most preferably humans.

The term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting or slowing further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

The phrase "therapeutically effective amount" refers to the amount of active salt or crystalline form or pharmaceutical agent that elicits the biological or medicinal response that is being sought in a tissue, system, animal, individual or human by a researcher, veterinarian, medical doctor or other clinician.

Certain features of the invention, which are, for clarity, described in the context of separate embodiments, can also be provided in combination in a single embodiment.

Conversely, various features of the invention, which are, for brevity, described in the context of a single embodiment, can also be provided separately or in any suitable subcombination.

Abbreviations

The following abbreviations and symbols may be used in the present disclosure: Ac (acetyl); aq. (aqueous); Boc (tert-butyloxycarbonyl); Bu (butyl); ° C. (degrees Celsius); c (concentration); conc. (concentrated); d (day(s)); DCM (dichloromethane); DEA (diethylamine); DIPEA (N-ethyl-N,N-diisopropylamine (Hünig's base)); DMF (N,N-dimethylformamide); DMSO (dimethylsulfoxide); DSC (differential scanning calorimetry); DVS (dynamic vapor sorption); EDTA (ethylenediaminetetraacetic acid); EGTA (ethyleneglycoltetraacetic acid); eq. (equivalent(s)); ESI (electron spray ionization); Et (ethyl); $Et_2O$ (diethyl ether); EtOAc (ethyl acetate); EtOH (ethanol); g (gram(s)); h (hour(s)); HPLC (high performance liquid chromatography); HCl (hydrochloric acid); i (iso); iPrOH (isopropanol); L (liter(s)); LC (liquid chromatography); M (molar); mg (milligram(s)) Me (methyl); MeCN (acetonitrile); MeOH (methanol); min. (minutes); mL (milliliter); mM (millimolar); MPLC (medium pressure liquid chromatography); MS (mass spectrometry); NP (normal phase); Ph (phenyl); Pr (propyl); Py (pyridine); rac (racemic); Rf (retention factor); RH (relative humidity); RP (reversed phase); rps (revolutions per second; rt (ambient temperature); tBu (tert-butyl); TEA (triethylamine); temp. (temperature); tert (tertiary); Tf (triflate); TFA (trifluoroacetic acid); TGA (thermogravimetric analysis); THF (tetrahydrofuran); TLC (thin layer chromatography); tRet. (retention time (HPLC)); UV (ultraviolet), XRPD (X-ray powder diffraction). Other common abbreviations may also be used herein.

II. Crystalline Salts

The present disclosure relates to, inter alia, salt forms, and, in particular, crystalline salt forms of (N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide (BI 882370), having Formula I:

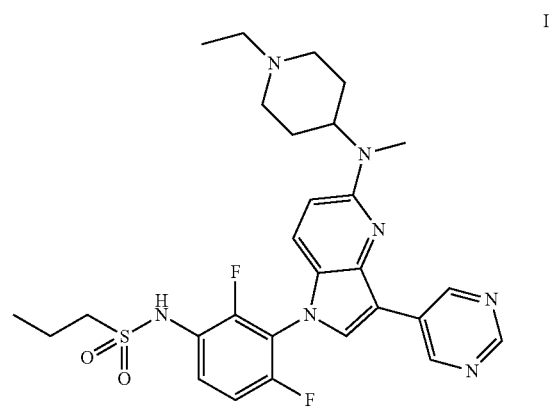 [SMILES: CCCS(=O)(=O)Nc1ccc(F)c(-n2cc(-c3cncnc3)c3nc(N(C)C4CCN(CC)CC4)ccc32)c1F]

which are useful, for example, in the preparation of solid dosage forms of the above compound for the treatment of various diseases, including cancer.

Different salt and crystalline forms of the same substance may have different bulk properties relating to, for example, hygroscopicity, solubility, stability, and the like. Forms with high melting points may have good thermodynamic stability, which can be advantageous in prolonging shelf-life drug formulations containing the particular salt or crystalline form. Forms with lower melting points may be less thermodynamically stable, but are advantageous in that they have increased water solubility, translating to increased drug bioavailability. Forms that are weakly hygroscopic may be desirable for their stability to heat and humidity and resistance to degradation during long storage. Anhydrous forms may be desirable because they can be consistently made without concern for variation in weight or composition due to varying solvent or water content. On the other hand, hydrated or solvated forms may sometimes be advantageous if they are less hygroscopic and show improved stability to humidity under storage conditions.

As used herein, "crystalline form" is meant to refer to a certain lattice configuration of a crystalline substance (which can include the salts described herein). Different crystalline forms of the same substance may have different crystalline lattices (e.g., unit cells) which are attributable to different physical properties that are characteristic of each of the crystalline forms. In some instances, different lattice configurations have different water or solvent content. The different crystalline lattices can be identified by solid-state characterization methods such as by X-ray powder diffraction (XRPD). Other characterization methods such as differential scanning calorimetry (DSC), thermogravimetric analysis (TGA), dynamic vapor sorption (DVS), solid state NMR, and the like further help identify the crystalline form as well as help determine stability and solvent/water content.

Crystalline forms of a substance can include both solvated (e.g., hydrated) and non-solvated (e.g., anhydrous) forms. A hydrated form is a crystalline form that includes water in the crystalline lattice. Hydrated forms can be stoichiometric hydrates, where the water is present in the lattice in a certain water/molecule ratio such as for hemihydrates, monohydrates, dihydrates, etc. Hydrated forms can also be non-stoichiometric, where the water content is variable and dependent on external conditions such as humidity.

Crystalline forms may be characterized by X-ray powder diffraction (XRPD). An XRPD pattern of reflections (peaks) is typically considered a fingerprint of a particular crystalline form. It is well known that the relative intensities of the XRPD peaks can widely vary depending on, inter alia, the sample preparation technique, crystal size distribution, filters, the sample mounting procedure, and the particular instrument employed. In some instances, new peaks may be observed or existing peaks may disappear, depending on the type of instrument or the settings (for example, whether a Ni filter is used or not). As used herein, the term "peak" refers to a reflection having a relative height/intensity of at least about 4% of the maximum peak height/intensity. Moreover, instrument variation and other factors can affect the 2-theta values. Thus, peak assignments, such as those reported herein, can vary by plus or minus about 0.2° (2-theta), and the term "substantially" as used in the context of XRPD herein is meant to encompass the above-mentioned variations.

In the same way, temperature readings in connection with differential scanning calorimetry (DSC), thermogravimetric analysis (TGA), or other thermal experiments can vary about ±4° C. depending on the instrument, particular settings, sample preparation, etc. For example, with DSC it is known that the temperatures observed will depend on the rate of the temperature change as well as the sample preparation technique and the particular instrument employed. Thus, the values reported herein related to DSC thermograms can vary, as indicated above, by ±4° C. Accordingly, a crystalline form reported herein having a DSC thermogram "substantially" as shown in any of the Figures is understood to accommodate such variation.

The salts described herein can be isolated in various crystalline forms, which can include crystalline forms that are anhydrous, hydrated, non-solvated, or solvated. Example hydrates include hemihydrates, monohydrates, dihydrates, and the like. In some embodiments, the crystalline forms are anhydrous and non-solvated. By "anhydrous" is meant that the crystalline form of the compound of Formula I contains essentially no bound water in the crystal lattice structure, i.e., the compound does not form a crystalline hydrate.

In some embodiments, the salts and crystalline forms invention can substantially isolated. By "substantially isolated" is meant that a particular salt or crystalline form of the compound is at least partially isolated from impurities. For example, in some embodiments a salt or crystalline form of the invention comprises less than about 50%, less than about 40%, less than about 30%, less than about 20%, less than about 15%, less than about 10%, less than about 5%, less than about 2.5%, less than about 1%, or less than about 0.5% of impurities. Impurities generally include anything that is not the substantially isolated salt or crystalline form including, for example, other salts or other crystalline forms and other substances.

In some embodiments, a salt or crystalline form is substantially free of other crystalline forms. The phrase "substantially free of other crystalline forms" means that a particular crystalline form comprises greater than about 80%, greater than about 90%, greater than about 95%, greater than about 98%, greater than about 99% or greater than about 99.5% by weight of the particular crystalline form.

The present disclosure provides a crystalline N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt and particular crystalline forms of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt.

The term "monosuccinate salt" means that the succinic acid and N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide base moieties present in the salt are present in a ratio of acid:base of about 1:1, e.g., a ratio in the range from about 0.8:1 to about 1.2:1, from about from about 0.9:1 to about 1.1:1, from about 1:1.2 to about 1:0.8, or from about 1:1.1 to about 1:0.9, e.g., a ratio of about 0.8:1, about 0.9:1, about 1:1, or about 1.1:1, or about 1:0.8, about 1:0.9, about 1:1, about 1:1.1 or about 1:1.2.

As described in further detail below, the crystalline monosuccinate salt of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide has unexpected properties such as improved solubility, improved intrinsic dissolution rate, and improved pharmacokinetic properties compared with the free base and other salt forms of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide.

In some embodiments, the crystalline salt is substantially anhydrous. By "substantially anhydrous" it is meant that the crystalline salt contains less than a stoichiometric equivalent amount of water, and does not contain water as part of the crystal structure of the salt. In some embodiments, water, if present, is present in an amount of about 5% or less, about 4% or less, about 3% or less, about 2% or less, about 1% or less, about 0.5% or less, about 0.2% or less, or about 0.1% or less by weight of the crystalline salt. The use of the term "substantially anhydrous" does not exclude the presence of trace amounts of water.

In some embodiments, the crystalline salt is substantially non-solvated. By "substantially non-solvated" it is meant that the crystalline salt contains less than a stoichiometric equivalent amount of solvent, and does not contain solvent molecules as part of the crystal structure of the salt. In some embodiments, solvent, if present, is present in an amount of about 5% or less, about 4% or less, about 3% or less, about 2% or less, about 1% or less, about 0.5% or less, about 0.2% or less, or about 0.1% or less by weight of the crystalline salt. The use of the term "substantially non-solvated" does not exclude the presence of trace amounts of solvent.

In some embodiments, the crystalline salt is substantially free of solvents other than water. By "substantially free" it is meant that the crystalline salt contains less than a stoichiometric equivalent amount of solvent other than water, and does not contain solvent molecules other than water as part of the crystal structure of the salt. In some embodiments, solvents other than water, if present, are present in an amount of about 5% or less, about 4% or less, about 3% or less, about 2% or less, about 1% or less, about 0.5% or less, about 0.2% or less, or about 0.1% or less by weight of the crystalline salt. The use of the term "substantially free of solvents other than water" does not exclude the presence of trace amounts of such solvents.

In some embodiments, the crystalline salt is Form A of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt (as described in further detail below).

A crystalline form of the salt be identified by unique signatures with respect to, for example, X-ray powder diffraction (XRPD), differential scanning calorimetry (DSC), thermogravimetric analysis (TGA), and dynamic vapor sorption (DVS).

Figure 10:
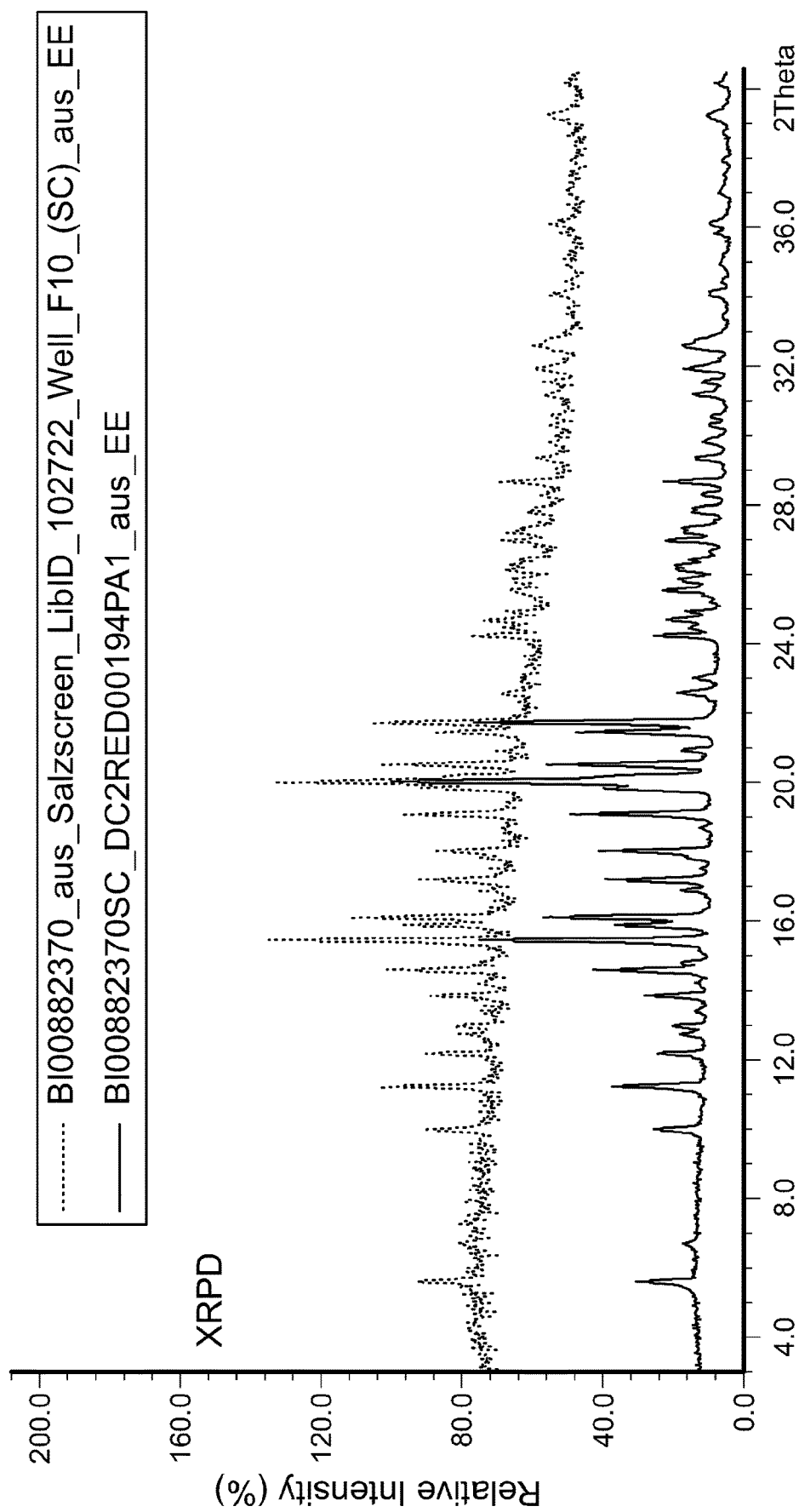
FIG. 10 is a plot of the XRPD of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt with the sample from well F10 (lower plot) compared to the sample obtained from scale-up synthesis (upper plot).
Figure 26:
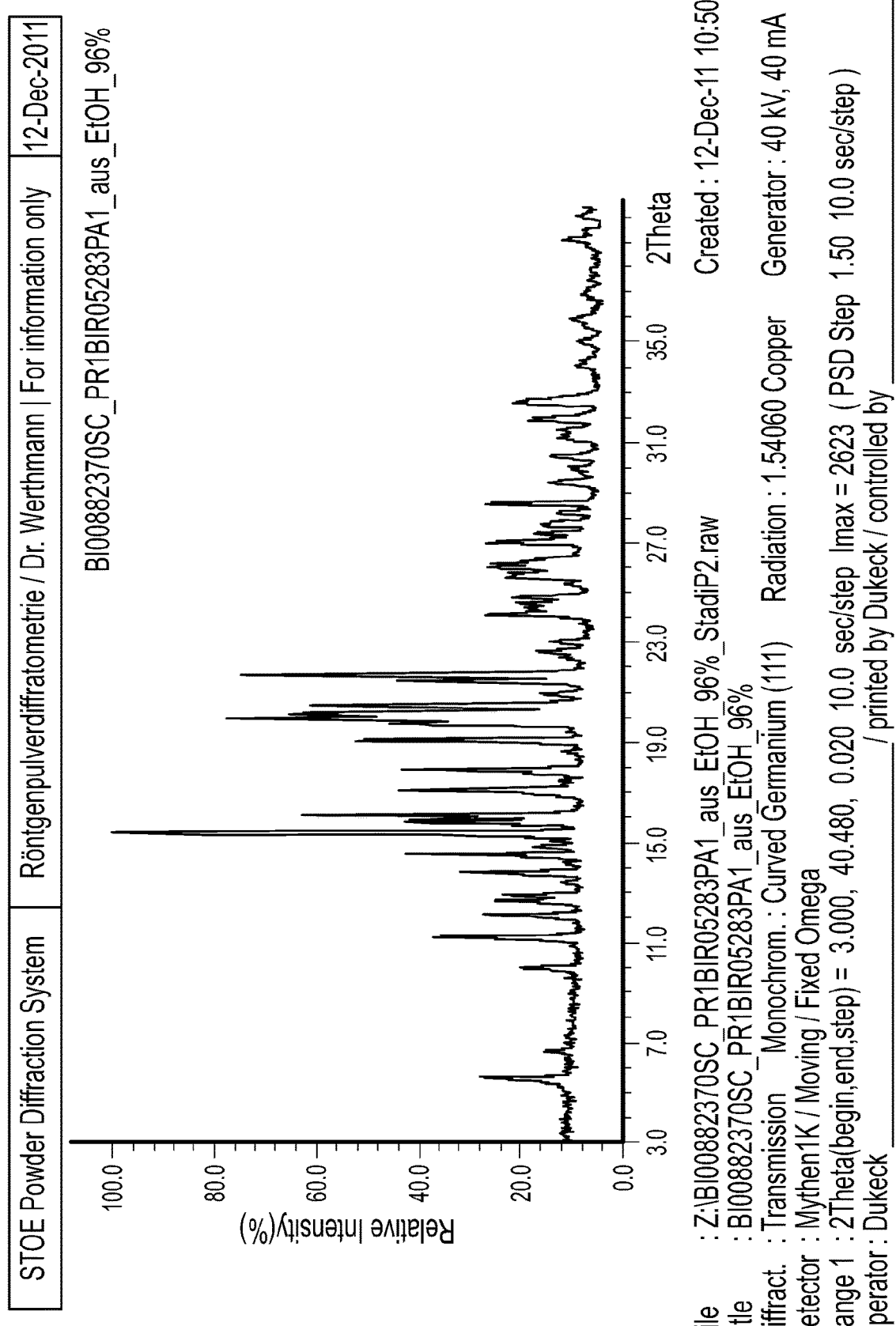
FIG. 26 is a plot of the XRPD of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt).
Figure 38:
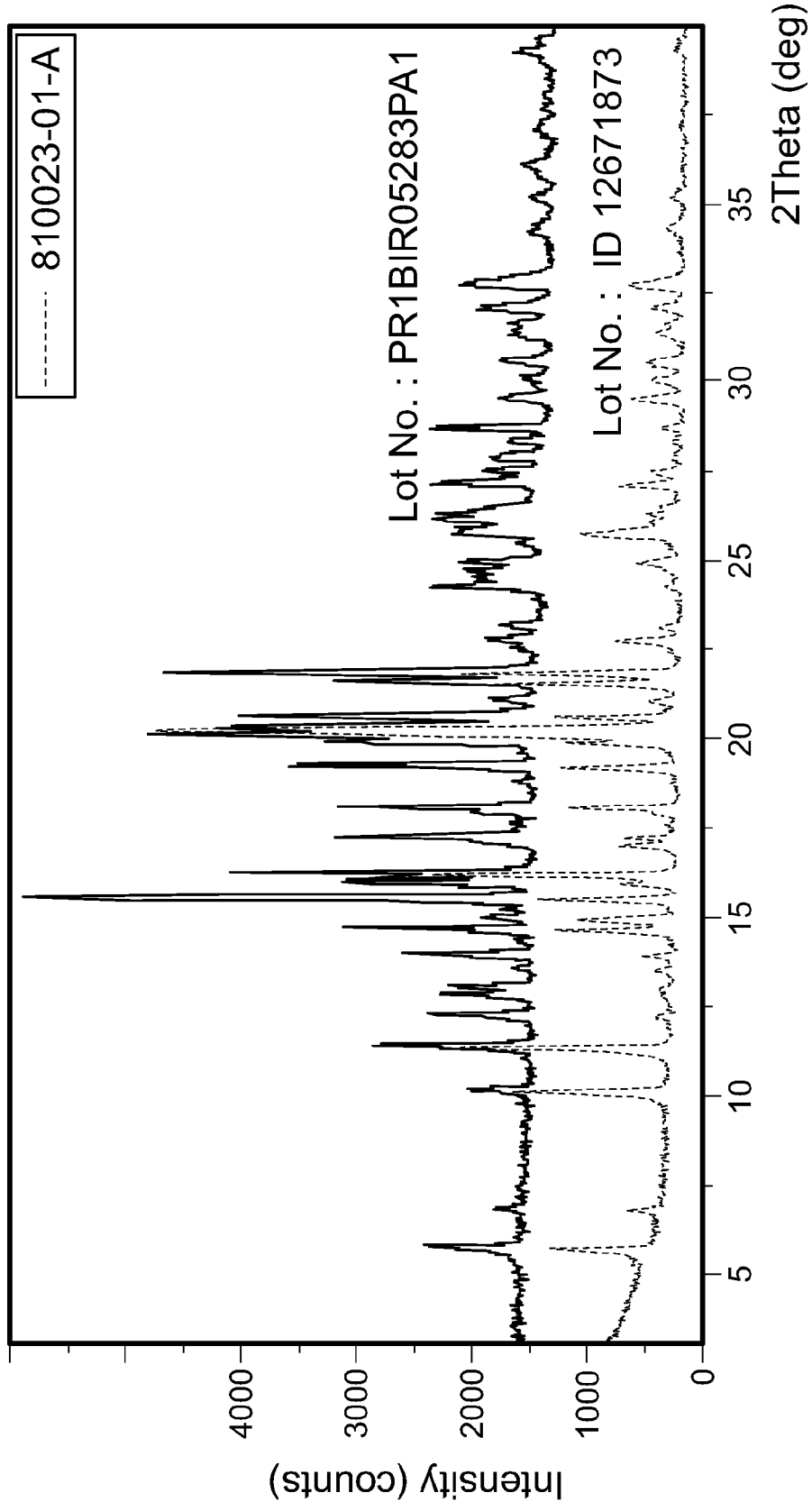
FIG. 38 is a plot of the XRPD of two batches of Form A of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt.

In some embodiments, Form A of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt is characterized by an XRPD pattern substantially as shown in FIG. 10, FIG. 26, or FIG. 38.

In some embodiments, Form A of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt is characterized by an XRPD pattern having substantially as shown in Table 9.

In some embodiments, the crystalline salt has an X-ray powder diffraction pattern comprising at least one of the following peaks, in terms of 2θ: 15.4°±0.5°; 20.0°±0.5°; and 21.8°±0.5°. In some embodiments, the peak at 15.4°±0.5°; 20.0°±0.5°; 21.8°±0.5° is the peak of the highest relative intensity in the X-ray powder diffraction pattern.

In some embodiments, the crystalline salt has an X-ray powder diffraction pattern comprising at least one of the following peaks, in terms of 2θ: 15.4°±0.2°; 20.0°±0.2°; and 21.8°±0.2°. In some embodiments, the peak at 15.4°±0.2°; 20.0°±0.2°; or 21.8°±0.2° is the peak of the highest relative intensity in the X-ray powder diffraction pattern.

In some embodiments, the crystalline salt has an X-ray powder diffraction pattern comprising at least one peak, in terms of 2θ, at 15.4°±0.5°. In some embodiments, the peak at 15.4°±0.5° is the peak of the highest relative intensity in the X-ray powder diffraction pattern.

In some embodiments, the crystalline salt has an X-ray powder diffraction pattern comprising at least one peak, in terms of 2θ, at 15.4°±0.2°. In some embodiments, the peak at 15.4°±0.2° is the peak of the highest relative intensity in the X-ray powder diffraction pattern.

In some embodiments, the crystalline salt has an X-ray powder diffraction pattern comprising the following peaks, in terms of 2θ: 15.4°±0.5°; 20.0°±0.5°; and 21.8°±0.5°. In some embodiments, the peak at 15.4°±0.5°; 20.0°±0.5°; or 21.8°±0.5°. is the peak of the highest relative intensity in the X-ray powder diffraction pattern.

In some embodiments, the crystalline salt has an X-ray powder diffraction pattern comprising the following peaks, in terms of 2θ: 15.4°±0.2°; 20.0°±0.2°; and 21.8°±0.2°. In some embodiments, the peak at 15.4°±0.2°; 20.0°±0.2°; or 21.8°±0.2° is the peak of the highest relative intensity in the X-ray powder diffraction pattern.

In some embodiments, the crystalline salt has an X-ray powder diffraction pattern comprising at least three, at least four, at least five, at least six, at least seven, at least eight, at least nine, or all of the following peaks, in terms of 2θ: 15.4°±0.5°; 16.1°±0.5°; 17.2°±0.5°; 19.1°±0.50; 19.8° 0.50; 20.0°±0.50; 20.2°±0.50; 20.5°±0.50; 21.5°±0.50; and 21.8°±0.5°. In some embodiments, the X-ray powder diffraction pattern comprises a peak at 15.4°±0.5°; 20.0°±0.5°; or 21.80° 0.5° as the peak of the highest relative intensity in the X-ray powder diffraction pattern.

In some embodiments, the X-ray powder diffraction pattern comprises a peak at 15.4°±0.5° as the peak of the highest relative intensity in the X-ray powder diffraction pattern.

In some embodiments, the crystalline salt has an X-ray powder diffraction pattern comprising at least three, at least four, at least five, at least six, at least seven, at least eight, at least nine, or all of the following peaks, in terms of 2θ: 15.4°±0.2°; 16.1°±0.2°; 17.2°±0.2°; 19.1°±0.2; 19.8° 0.2; 20.0°±0.20; 20.2°±0.20; 20.5°±0.20; 21.5°±0.20; and 21.8°±0.2°. In some embodiments, the X-ray powder diffraction pattern comprises a peak at 15.4°±0.2°; 20.0°±0.2°; or 21.80° 0.2° as the peak of the highest relative intensity in the X-ray powder diffraction pattern. In some embodiments, the X-ray powder diffraction pattern comprises a peak at 15.4°±0.2° as the peak of the highest relative intensity in the X-ray powder diffraction pattern.

In some embodiments, the X-ray powder diffraction pattern comprises at least two of the peaks at 15.4°±0.5°; 20.0°±0.5°; or 21.8°±0.5° as the peaks of the highest relative intensity in the X-ray powder diffraction pattern.

In some embodiments, the X-ray powder diffraction pattern comprises at least three of the peaks at 15.4°±0.5°; 20.0°±0.5°; or 21.8°±0.5° as the peaks of the highest relative intensity in the X-ray powder diffraction pattern.

In some embodiments, the X-ray powder diffraction pattern comprises at least two of the peaks at 15.4°±0.2°; 20.0°±0.2°; or 21.8°±0.2° as the two peaks of the highest relative intensity in the X-ray powder diffraction pattern.

In some embodiments, the X-ray powder diffraction pattern comprises the peaks at 15.4°±0.2°; 20.00° 0.2°; or 21.8°±0.2° as the three peaks of the highest relative intensity in the X-ray powder diffraction pattern.

Figure 11:
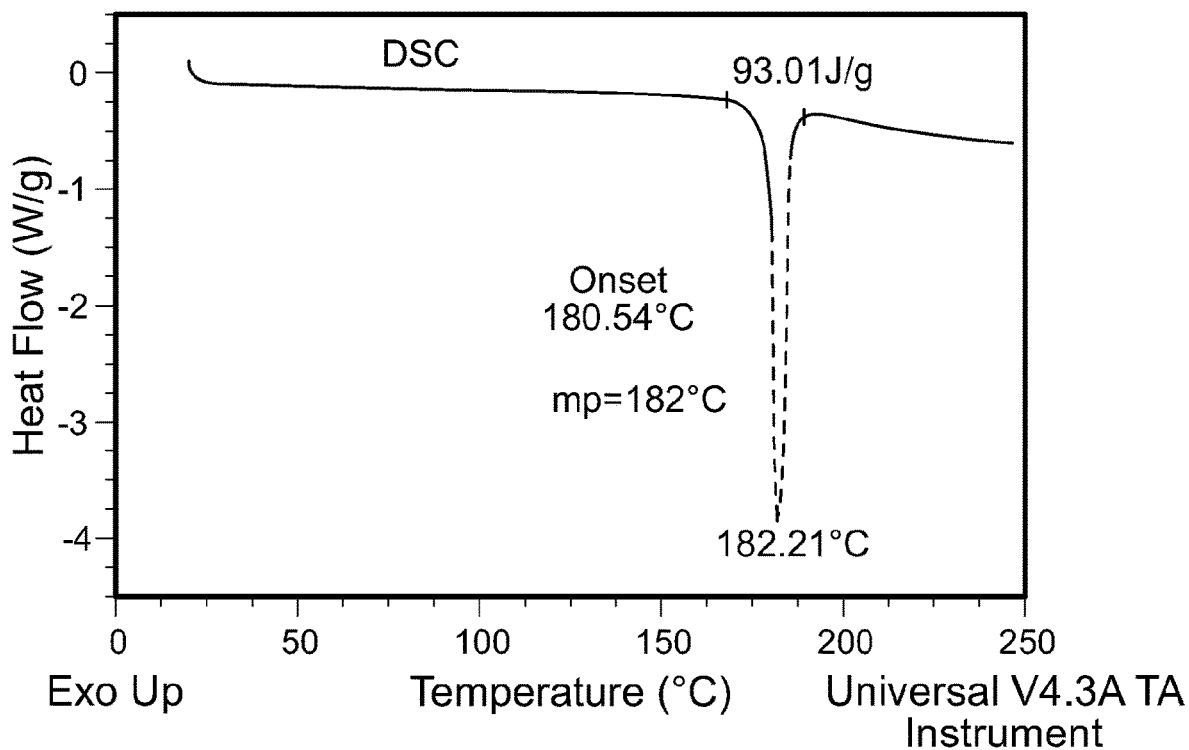
FIG. 11 is a DSC plot of N-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt.
Figure 27:
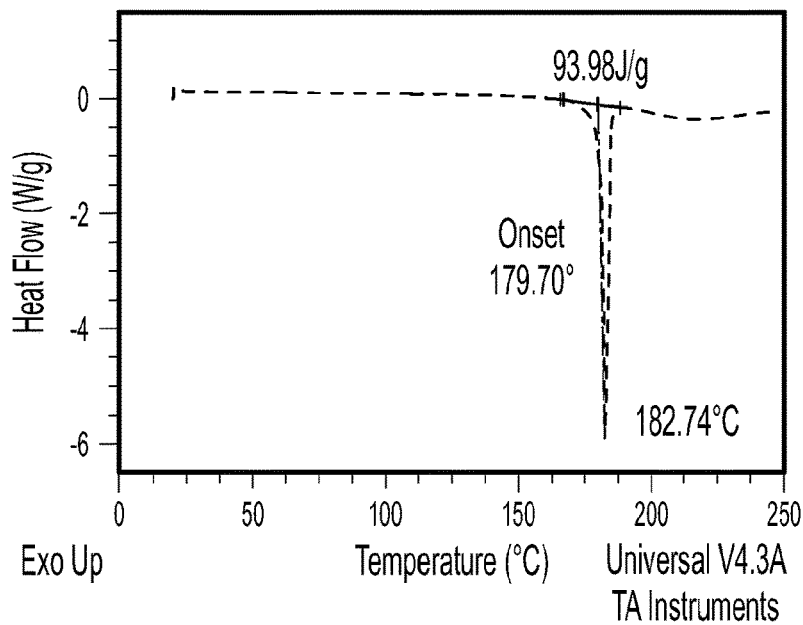
FIG. 27 is a DSC plot of N-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt.
Figure 39:
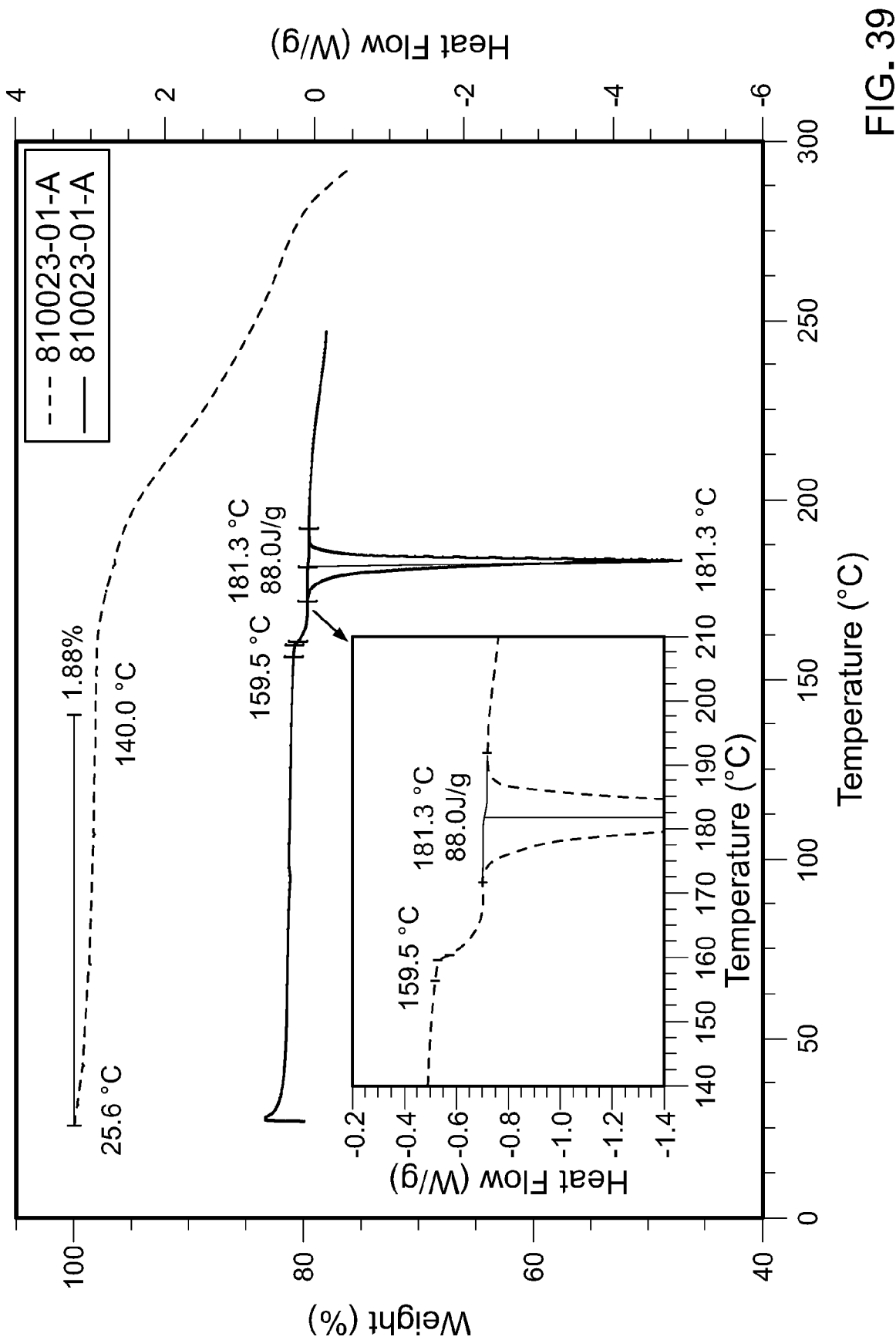
FIG. 39 is a pair of plots of the TGA and DSC analysis of Form A of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt.

In some embodiments, the crystalline salt has a differential scanning calorimetry thermogram (DSC) substantially as shown in FIG. 11, FIG. 27, or FIG. 39.

Figure 12:
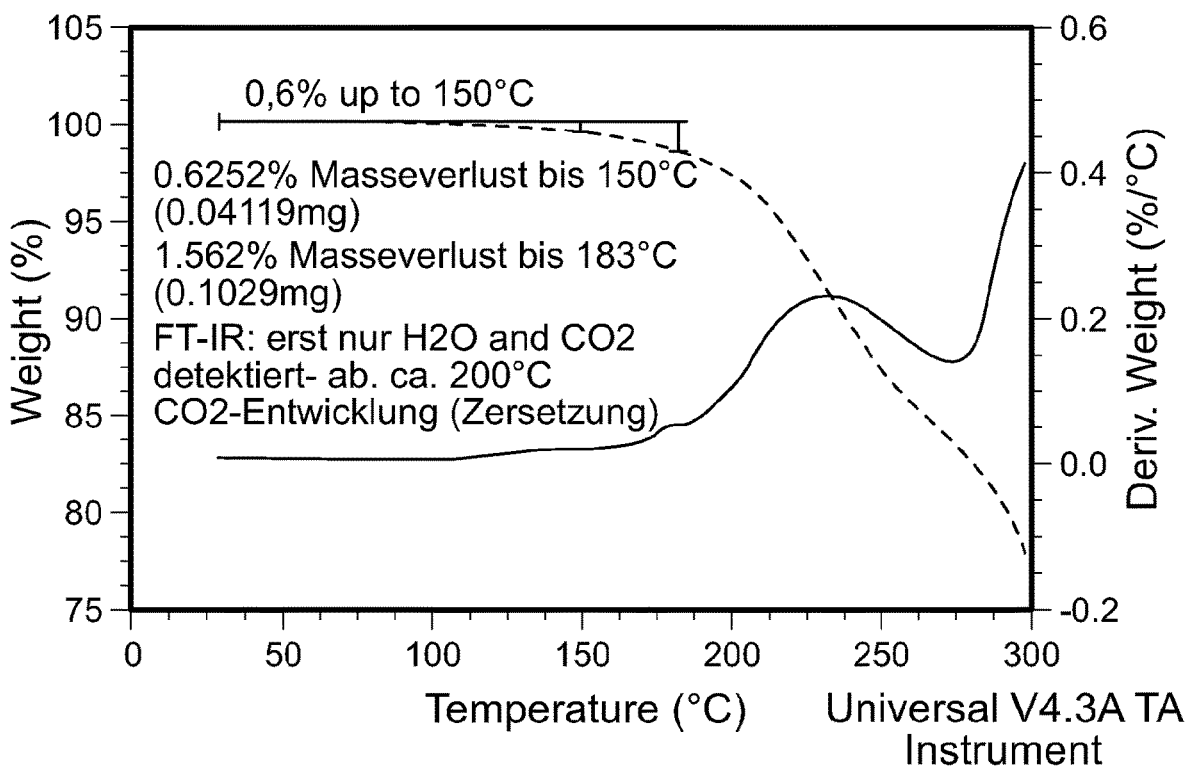
FIG. 12 is a TGA plot of N-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt.
Figure 28:
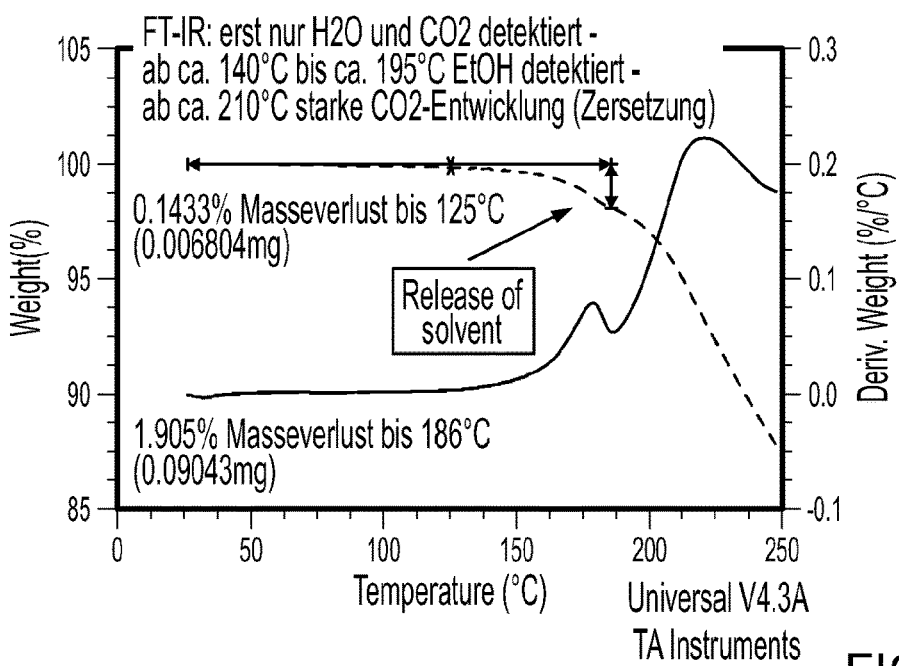
FIG. 28 is a TGA plot of N-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt.

In some embodiments, the crystalline salt has a thermogravimetric analysis (TGA) substantially as shown in FIG. 12, FIG. 28 or FIG. 39.

In some embodiments, the crystalline salt is substantially isolated. In some embodiments, the crystalline salt is at least 80%, at least 90%, at least 95%, at least 96%, at least 97%, at least 98%, at least 99% N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt Form A.

N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt may be prepared by reacting N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide with an appropriate amount, typically about one equivalent, of succinic acid.

The reaction may be carried out in a suitable solvent. The reaction can be carried out by dissolving the N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide and adding succinic acid, which may also be dissolved in the acid. If necessary, heating of the solutions of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide and/or succinic acid may be performed to dissolve the compound. Heating may be to a temperature above room temperature, e.g., about 30° C., about 40° C., about 50° C., about 60° C., about 70° C., about 80° C., about 90° C., or about 100° C. The reaction can be performed for a period of time, e.g., about 5 min., about 10 min., about 20 min., about 30 min., about 40 min., about 50 min., about 1 h, about 2 h, about 3 h, or about 4 h. Following heating, the solution may be cooled, e.g., to a temperature of room temperature or lower, e.g., about 25° C., about 20° C., about 15° C., about 10° C., about 5° C., or about 0° C. Following such cooling, the reaction mixture may be maintained for a further period of time at the lower temperature, e.g., for about 5 min., about 10 min., about 20 min., about 30 min., about 40 min., about 50 min., about 1 h, about 2 h, about 3 h, about 4 h, about 8 h, about 16 h, or about 24 h.

During the steps performed to form the salt or crystalline form thereof, the solution or suspension in which the reaction is carried out may be agitated, e.g., stirred.

Suitable solvents for forming N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinic acid salt, including Form A of the salt, include a $C_{1-4}$ alcohol, aqueous $C_{1-4}$ alcohol or ethyl acetate. The solvents can include methanol, ethanol, isopropanol, aqueous methanol, aqueous ethanol, aqueous isopropanol, or ethyl acetate.

Crystalline N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinic acid salt, and Form A in particular, may result directly from the reaction of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide with succinic acid under appropriate conditions. Alternatively, the crystalline salt, or Form A thereof, can be prepared by crystallizing the salt and/or recrystallizing the salt a suitable solvent.

A suitable procedure for crystallizing the salt or recrystallizing the salt include a solution or suspension of the salt in the suitable solvent. Heating may be to a temperature above room temperature, e.g., about 30° C., about 40° C., about 50° C., about 60° C., about 70° C., about 80° C., about 90° C., or about 100° C. The heating can be performed for a period of time, e.g., about 5 min., about 10 min., about 20 min., about 30 min., about 40 min., about 50 min., about 1 h, about 2 h, about 3 h, or about 4 h. Following heating, the solution may be cooled, e.g., to a temperature of room temperature or lower, e.g., about 25° C., about 20° C., about 15° C., about 10° C., about 5° C., or about 0° C. Following such cooling, the reaction mixture may be maintained for a further period of time at the lower temperature, e.g., for about 5 min., about 10 min., about 20 min., about 30 min., about 40 min., about 50 min., about 1 h, about 2 h, about 3 h, about 4 h, about 8 h, about 16 h, or about 24 h. During the steps performed to crystallize or recrystallize the salt or crystalline form thereof, the solution or suspension in which the reaction is carried out may be agitated, e.g., stirred.

III. Methods of Use

The salts and crystalline forms described in the present disclosure are B-RAF-kinase inhibitors, and are therefore useful in treating pathological disorders (diseases) in which the RAS-RAF-MAPK signaling pathway is activated, particularly cellular proliferative disorders such as cancer. The salts and crystalline forms can inhibit proliferation of cells, in particular by inhibiting entry into the DNA synthesis phase. The treated cells arrest in the Gi phase of the cell cycle. The salts and crystalline forms are therefore useful for treating diseases characterised by excessive or abnormal cell proliferation.

The pathological disorders that can be treated with the salts and crystalline forms described in the present disclosure include diseases associated with abnormal expression or activity of a RAF kinase. The disease may be treated by administering to a patient in need of such treatment a therapeutically effective amount of a crystalline salt, or any of the embodiments thereof, as described herein. In some embodiments, the disease is associated with abnormal expression or activity of a B-RAF kinase. In some embodiments, the disease is associated with abnormal expression or activity of a mutated B-RAF kinase. In some embodiments, the disease is associated with abnormal expression or activity of a V600E mutated B-RAF kinase. In other embodiments, the disease can be associated with expression or activity of a mutated B-RAF kinase selected from the following mutants: R461I, I462S, G463E, G463V, G465A, G465E, G465V, G468A, G468E, N580S, E585K, D593V, F594L, G595R, L596V, T598I, V599D, V599E, V599K, V599R, V600K, and A727V.

The pathological disorders that can be treated with the salts and crystalline forms described in the present disclosure include cancer, infections, inflammation and autoimmune diseases.

The pathological disorders that can be treated with the salts and crystalline forms described in the present disclosure include cancers. The cancers can include tumors and also cancers that do not form tumors such as haematological cancers.

In some embodiments, the cancer is breast cancer, prostate cancer, colon cancer, endometrial cancer, brain cancer, bladder cancer, skin cancer, cancer of the uterus, cancer of the ovary, lung cancer, pancreatic cancer, renal cancer, gastric cancer, or a hematological cancer. In some embodiments, the hematological cancer is acute myeloblastic leukemia, chronic myeloid leukemia, B cell lymphoma, chronic lymphocytic leukemia (CLL), Non-Hodgkins lymphoma, hairy cell leukemia, Mantle cell lymphoma, Burkitt lymphoma, small lymphocytic lymphoma, follicular lymphoma, lymphoplasmacytic lymphoma, extranodal marginal zone lymphoma, activated B-cell like (ABC) diffuse large B cell lymphoma, or germinal center B cell (GCB) diffuse large B cell lymphoma. In some embodiments, the non-Hodgkin lymphoma (NHL) is selected from relapsed NHL, refractory NHL, and recurrent follicular NHL.

In some embodiments, the cancer is breast, prostate, colon, endometrial, brain, bladder, skin, uterus, ovary, lung, pancreatic, renal, gastric, or a hematological cancer.

In some embodiments, the cancer is malignant melanoma, thyroid cancer, colorectal cancer, biliary tract cancer, prostate cancer, ovary cancer or non-small cell lung cancer.

In some embodiments, the cancer is associated with expression or activity of a RAF kinase.

In some embodiments, the cancer is associated with expression or activity of a B-RAF kinase.

In some embodiments, the cancer is associated with expression or activity of a mutated B-RAF kinase.

In some embodiments, the cancer is associated with expression or activity of a V600E mutated B-RAF kinase.

In some embodiments, the cancer is associated with expression or activity of a mutated B-RAF kinase selected from the following mutants: R461I, I462S, G463E, G463V, G465A, G465E, G465V, G468A, G468E, N580S, E585K, D593V, F594L, G595R, L596V, T598I, V599D, V599E, V599K, V599R, V600K, and A727V.

In some embodiments, the cancer is melanoma.

In some embodiments, the cancer is colorectal cancer.

In some embodiments, the cancer is colon cancer.

In some embodiments, the cancer is thyroid cancer.

In some embodiments, the cancer expresses a mutated B-RAF kinase. In some embodiments, the cancer expresses a V600E mutated B-RAF kinase. In some embodiment, the cancer expresses one or more of the following B-RAF kinase mutants: R461I, 1462S, G463E, G463V, G465A, G465E, G465V, G468A, G468E, N580S, E585K, D593V, F594L, G595R, L596V, T598I, V599D, V599E, V599K, V599R, V600K, and A727V.

The following cancers may be treated with compounds according to the invention, without being restricted thereto: brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningiomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon carcinoma, colorectal carcinoma, anal carcinoma, carcinoma of the large bowel, tumours of the small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas (NSCLC) such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypemephroma or Grawitz's tumour; oesophageal cancer or carcinoma of the oesophagus; penile cancer; prostate cancer; throat cancer or carcinomas of the pharynx such as for example nasopharynx carcinomas, oropharynx carcinomas and hypopharynx carcinomas; retinoblastoma, vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidermoid carcinoma and plate epithelial carcinoma of the skin; thymomas, cancer of the urethra and cancer of the vulva.

The new salts and crystalline forms may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The salts and crystalline forms described herein may also be used to treat non-cancer proliferative disorders. Examples of proliferative disorders that can be treated include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

Other diseases that can be treated include viral infections (e.g., Epstein-Barr virus, hepatitis B virus, hepatitis C virus, herpes virus, human immunodeficiency virus, human papilloma virus, Kaposi's sarcoma, adenovirus, poxvirus and other episome-based DNA viruses). The salts and crystalline forms can therefore be used to treat disease and conditions such as herpes simplex infections and reactivations, cold sores, herpes zoster infections and reactivations, chickenpox, shingles, human papilloma virus, cervical neoplasia, adenovirus infections, including acute respiratory disease, and poxvirus infections such as cowpox and smallpox and African swine fever virus. In one particular embodiment, salts and crystalline forms are indicated for the treatment of human papilloma virus infections of skin or cervical epithelia.

Other diseases that can be treated include inflammatory and autoimmune diseases. Examples of autoimmune and inflammatory conditions that can be treated include acute, hyperacute or chronic rejection of transplanted organs, acute gout, acute inflammatory responses (such as acute respiratory distress syndrome and ischemia/reperfusion injury), Addison's disease, agammaglobulinemia, allergic rhinitis, allergy, alopecia, Alzheimer's disease, appendicitis, atherosclerosis, asthma, osteoarthritis, juvenile arthritis, psoriatic arthritis, rheumatoid arthritis, atopic dermatitis, autoimmune alopecia, autoimmune hemolytic and thrombocytopenic states, autoimmune hypopituitarism, autoimmune polyglandular disease, Behcet's disease, bullous skin diseases, cholecystitis, chronic idiopathic thrombocytopenic purpura, chronic obstructive pulmonary disease (COPD), cirrhosis, degenerative joint disease, depression, dermatitis, dermatomyositis, eczema, enteritis, encephalitis, gastritis glomerulonephritis, giant cell arteritis, Goodpasture's syndrome, Guillain-Barre syndrome, gingivitis, Graves' disease, Hashimoto's thyroiditis, hepatitis, hypophysitis, inflammatory bowel disease (Crohn's disease and ulcerative colitis), inflammatory pelvic disease, irritable bowel syndrome, Kawasaki disease, LPS-induced endotoxic shock, meningitis, multiple sclerosis, myocarditis, myasthenia gravis, mycosis fungoides, myositis, nephritis, osteomyelitis, pancreatitis, Parkinson's disease, pericarditis, pernicious anemia, pneumonitis, primary biliary sclerosing cholangitis, polyarteritis *nodosa*, psoriasis, retinitis, scleritis, scleracierma, scleroderma, sinusitis, Sjogren's disease, sepsis, septic shock, sunburn, systemic lupus erythematosus, tissue graft rejection, thyroiditis, type I diabetes, Takayasu's arteritis, urethritis, uveitis, vasculitis, vasculitis including giant cell arteritis, vasculitis with organ involvement such as glomerulonephritis, vitiligo, Waldenstrom macroglobulinemia and Wegener's granulomatosis.

Further diseases include bacterial, fungal and/or parasitic infections; skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. endometrial hyperplasia); bone diseases and cardiovascular diseases (e.g. restenosis and hypertrophy).

The salts and crystalline forms described herein are also suitable for protecting proliferating cells (e.g. hair, intestinal, blood and progenitor cells) from DNA damage caused by radiation, UV treatment and/or cytostatic treatment.

Combination Therapies

The salts and crystalline forms described herein may be used on their own or in combination with other active substances according to the invention, optionally also in combination with other pharmacologically active substances such as other chemotherapeutic agents.

For treating cancer and other proliferative diseases, the compounds of the invention can be used in combination with chemotherapeutic agents, or other anti-proliferative agents. Chemotherapeutic agents which may be administered in combination with the salts and crystalline forms described herein for the treatment of cancer or other proliferative disorders, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor (PDGF)", "fibroblast growth factor (FGF)", "vascular endothelial growth factor (VEGF)", "epidermal growth factor (EGF)", "insuline-like growth factors (IGF)", "human epidermal growth factor (HER, e.g. HER2, HER3, HER4)" and "hepatocyte growth factor (HGF)"), inhibitors are for example "growth factor" antibodies, "growth factor receptor" antibodies and tyrosine kinase inhibitors, such as for example cetuximab, gefitinib, imatinib, lapatinib and trastuzumab); antimetabolites (e.g. antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulfan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); tubuline inhibitors; PARP inhibitors, topoisomerase inhibitors (e.g. epipodophyllotoxins such as for example etoposide and etopophos, teniposide, amsacrin, topotecan, irinotecan, mitoxantron), serine/threonine kinase inhibitors (e.g. PDK 1 inhibitors, B-Raf inhibitors, mTOR inhibitors, mTORC1 inhibitors, PI3K inhibitors, dual mTOR/PI3K inhibitors, STK 33 inhibitors, AKT inhibitors, PLK 1 inhibitors, inhibitors of CDKs, Aurora kinase inhibitors), tyrosine kinase inhibitors (e.g. PTK2/FAK inhibitors), protein interaction inhibitors (e.g. IAP, Mcl-1, MDM2/MDMX), MEK inhibitors, ERK inhibitors, IGF-1R inhibitors, ErbB receptor inhibitors, rapamycin analogs (e.g. everolimus, temsirolimus, ridaforolimus, sirolimus) and various chemotherapeutic agents such as amifostin, anagrelid, clodronat, filgrastin, interferon, interferon alpha, leucovorin, rituximab, procarbazine, levamisole, mesna, mitotane, pamidronate and porfimer.

Other agents which may be administered in combination with the salts and crystalline forms described herein, include 2-chlorodesoxyadenosine, 2-fluorodesoxycytidine, 2-methoxyoestradiol, 2C4, 3-alethine, 131-I-TM-601, 3CPA, 7-ethyl-10-hydroxycamptothecin, 16-aza-epothilone B, A 105972, A 204197, abarelix, abiraterone, aldesleukin, alemtuzumab, alitretinoin, allopurinol, allovectin-7, altretamine, alvocidib, amonafide, anastrozole, anthrapyrazole, AG-2037, AP-5280, apaziquone, apomine, aranose, arglabin, arsenic trioxide, arzoxifene, asparaginase, atamestane, atrasentan, auristatin PE, AVLB, AZ10992, ABX-EGF, AMG-479 (ganitumab), ARRY 162, ARRY 438162, ARRY-300, ARRY-142886/AZD-6244 (selumetinib), ARRY-704/AZD-8330, AR-12, AR-42, AS-703988, AXL-1717, AZD-8055, AZD-5363, AZD-6244, ARQ-736, ARQ 680, AS-703026 (primasertib), avastin, AZD-2014, azacytidine, azaepothilone B, azonafide, BAY-43-9006, BAY 80-6946, BBR-3464, BBR-3576, bevacizumab, bexarotene, BEZ-235, biricodar dicitrate, BCX-1777, BKM-120, bleocin, BLP-25, BMS-184476, BMS-247550, BMS-188797, BMS-275291, BMS-663513, BMS-754807, BNP-1350, BNP-7787, BIBW 2992 (afatinib, tomtovok), BIBF 1120 (vargatef), BI 836845, BI 2536, BI 6727, BI 836845, BI 847325, BI 853520, BIIB-022, bleomycinic acid, bleomycin A, bleomycin B, brivanib, bryostatin-1, bortezomib, brostallicin, busulfan, BYL-719, CA-4 prodrug, CA-4, CapCell, calcitriol, calusterone, canertinib, canfosfamide, capecitabine, carboplatin, carboxyphthalatoplatin, carmustine, CCI-779, CC-115, CC-223, CEP-701, CEP-751, CBT-1 cefixime, ceflatonin, ceftriaxone, celecoxib, celmoleukin, cemadotin, cetuximab, chlorambucil, CH4987655/RO-4987655, chlorotrianisene, cilengitide, cisplatin, CDA-II, CDC-394, CKD-602, CKI-27, cladribine, clofarabine, colchicin, combretastatin A4, COT inhibitors, CHS-828, CH-5132799, CLL-Thera, CMT-3 cryptophycin 52, CTP-37, CTLA-4 monoclonal antibodies, CP-461, CV-247, cyanomorpholinodoxorubicin, cyclophosphamide, cyclosporin, cytarabine, D 24851, dacarbazine, dactinomycin, dalteparin sodium, dasatinib, daunorubicin, decitabine, denileukin, denileukin diftitox, deoxorubicin, deoxyrubicin, deoxycoformycin, depsipeptide, desoxyepothilone B, dexamethasone, dexrazoxane, dexrazoxanet, diethylstilbestrol, diflomotecan, didox, DMDC, dolastatin 10, docetaxel, doranidazole, doxorubicin, dromostanolone propionate, DS-7423, E7010, E-6201, eculizumab, edatrexat, edotreotide, efaproxiral, eflomithine, EGFR inhibitors, EKB-569, EKB-509, enzastaurin, elsamitrucin, epirubicin, epothilone B, epratuzumab, ER-86526, erlotinib, estramustine, ET-18-OCH3, ethynylcytidine, ethynyloestradiol, etoposide phosphate, etoposide, exatecan, exatecan mesylate, exemestane, exisulind, fentanyl citrate, fenretinide, figitumumab, filgrastim, floxuridine, fludarabine, folic acid, fluorouracil, FOLFOX, FOLFOX4, FOLFIRI, formestane, fotemustine, fulvestrant, galarubicin, gallium maltolate, gefinitib, gemcitabine, gemtuzumab, gemtuzumab ozogamicin, gimatecan, glufosfamide, GCS-IOO, GDC-0623, GDC-0941 (pictrelisib), GDC-0980, GDC-0032, GDC-0068, GDC-0349, GDC-0879, G17DT immunogen, GMK, GPX-100, gp100-peptide vaccines, GSK-5126766, GSK-690693, GSK-1120212 (trametinib), GSK-2118436 (dabrafenib), GSK-2126458, GSK-2132231A, GSK-2334470, GSK-2110183, GSK-2141795, GW2016, goserelin acetate, granisetron, herceptin, hexamethylmelamine, histamine, histrelin acetate, homoharringtonine, hyaluronic acid, hydroxyurea, hydroxyprogesterone caproate, ibandronate, ibritumomab, ibritumomab tiuxetan, idarubicin, idatrexate, idenestrol, IDN-5109, ifosfamide, IGF-1R inhibitors, IMC-$1C_{11}$, IMC-A12 (cixutumumab), imatinib mesylate, immunol, indisulam, interferon alpha-2a, interferon alpha-2b, pegylated interferon alpha-2b, interleukin-2, INK-1117, INK-128, INSM-18, ionafamib, ipilimumab, iproplatin, irinotecan, irofulven, isohomohalichondrin-B, isoflavone, isotretinoin, ixabepilone, JRX-2, JSF-154, J-107088, conjugated oestrogens, kahalid F, ketoconazole, KW-2170, KW-2450, lapatinib ditosylate, leflunomide, lenalidomide, lenograstim, letrozole, leucovorin, leuprolide, leuprolide acetate, leuporelin, levamisole, lexidronam, LGD-1550, linezolid, lobaplatin, lutetium texaphyrin, lometrexol, lomustine, losoxantrone, LU 223651, lurtotecan, LY-S6AKT1, LY-2780301, mafosfamide, marimastat, mechloroethamine, megestrol acetate, MEK inhibitors, MEK-162, melphalan, mercaptopurine, methotrexate, methoxsalen, methyltestosterone, methylprednisolone, MEDI-573, MEN-10755, MDX-H210, MDX-447, MDX-1379, MGV, midostaurin, minodronic acid, mitomycin, mitomycin C, mitotane, mitoxantrone, mivobulin, MK-2206, MK-0646 (dalotuzumab), MLN518, motexafin gadolinium, MS-209, MS-275, MX6, nandrolone phenpropionate, nelarabine, neridronate, neratinib, Nexavar, neovastat, nilotinib, nimesulide, nitroglycerin, nofetumomab, nolatrexed, norelin, N-acetylcysteine, N-benzylguanine, oblimersen, omeprazole, oncophage, oncoVEX$^{GM-CSF}$, ormiplatin, ortataxel, oxaliplatin, OX44 antibodies, OSI-027, OSI-906 (linsitinib), 4-1BB antibodies, oxantrazole, oestrogen, paclitaxel, pamidronate, panitumumab, patupilone, pegfilgrastim, PCK-3145, pegaspargase, pegfilgrastim, PBI-1402, PBI-05204, PDO325901, PD-1 antibodies, PEG-paclitaxel, albumin-stabilized paclitaxel, PEP-005, PF-05197281, PF-05212384, PF-04691502, PHT-427, P-04, PKC412, P54, PI-88, pelitinib, pemetrexed, pemetrexed disodium, pentostatin, pentrix, perifosine, perillylalcohol, pertuzumab, PI3K inhibitors, PI3K/mTOR inhibitors, PG-TXL, PG2, PLX-4032/RO-5185426 (vemurafenib), PLX-3603/RO-5212054, PT-100, PWT-33597, PX-866, picoplatin, pipobroman, pivaloyloxymethylbutyrate, pixantrone, phenoxodiol O, PKI166, plevitrexed, plicamycin, polyprenic acid, porfiromycin, prednisone, prednisolone, procarbazine, quinacrine, quinamed, quinupristin, R115777, RAF-265, ramosetron, ranpimase, rasburicase, RDEA-119/BAY 869766, RDEA-436, rebeccamycin analogues, receptor tyrosine kinase (RTK) inhibitors, revimid, RG-7167, RG-7304, RG-7421, RG-7321, RG 7440, rhizoxin, rhuMAb, rinfabate, risedronate, rituximab, robatumumab, rofecoxib, RO-31-7453, RO-5126766, RO-5068760, RPR 109881A, rubidazone, rubitecan, R-flurbiprofen, RX-0201, S-9788, sabarubicin, SAHA, sargramostim, satraplatin, SB 408075, Se-015/Ve-015, SU5416, SU6668, SDX-101, semustin, seocalcitol, SM-11355, SN-38, SN-4071, SR-27897, SR-31747, SR-13668, SRL-172, sorafenib, spiroplatin, squalamine, streptozocin, suberanilohydroxamic acid, sunitinib, sunitinib maleate, sutent, T 900607, T 138067, TAK-733, TAS-103, tacedinaline, talaporfin, tamoxifen, Tarceva, tariquitar, tasisulam, taxotere, taxoprexin, tazarotene, tegafur, temozolamide, teniposide, tesmilifene, testosterone, testosterone propionate, tesmilifene, testolactone, tetraplatin, tetrodotoxin, tezacitabine, thalidomide, theralux, therarubicin, thioguanine, thiotepa, thymalfasin, thymectacin, tiazofurin, tipifamib, tirapazamine, tocladesine, tomudex, topotecan, toremifene, toremofin, tositumomab, trabectedin, TransMID-107, trans-retinic acid, traszutumab, tremelimumab, tretinoin, triacetyluridine, triapine, triciribine, trimetrexate, TLK-286TXD 258, tykerb/tyverb, urocidin, uracil mustard, valrubicin, vatalanib, vinblastine, vincristine, vinflunine, vinorelbine, virulizin, WX-UK1, WX-554, vectibix, vorinostat, xeloda, XELOX, XL-147, XL-228, XL-281, XL-518/R-7420/GDC-0973, XL-765, YM-511, YM-598, ZD-4190, ZD-6474, ZD-4054, ZD-0473, ZD-6126, ZD-9331, ZD1839, ZSTK-474, zoledronate and zosuquidar.

The compounds of the invention can also be used in combination with medical therapy such as surgery or radiotherapy, e.g., gamma-radiation, neutron beam radiotherapy, electron beam radiotherapy, proton therapy, brachytherapy, and systemic radioactive isotopes.

For treating autoimmune or inflammatory conditions, the compound of the invention can be administered in combination with a corticosteroid such as triamcinolone, dexamethasone, fluocinolone, cortisone, prednisolone, or flumetholone.

For treating autoimmune or inflammatory conditions, the compound of the invention can be administered in combination with an immune suppressant such as fluocinolone acetonide (Retisert®), rimexolone (AL-2178, Vexol, Alcon), or cyclosporine (Restasis®).

For treating autoimmune or inflammatory conditions, the compound of the invention can be administered in combination with one or more additional agents selected from Dehydrex™ (Holles Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S, 3S, 4R, 5R)-3, 4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), or thalidomide.

In some embodiments, the compound of the invention can be administered in combination with one or more agents selected from an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

The one or more additional pharmaceutical agents can be administered to a patient simultaneously or sequentially.

IV. Formulation, Dosage Forms and Administration

When employed as pharmaceuticals, the salts and crystalline forms described herein can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. The content of the pharmaceutically active compound should be in the range from 0.1 to 90 wt.-%, preferably 0.5 to 50 wt.-% of the composition as a whole, i.e. an amount which are sufficient to achieve the dosage range specified below.

This invention also includes pharmaceutical compositions which contain, as the active ingredient, the salts and crystalline forms described herein, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound in the form of a salt or crystalline form as described herein can be milled to provide the appropriate particle size prior to combining with the other ingredients. If the salt or crystalline form is substantially insoluble, it can be milled to a particle size of less than 200 mesh. If the salt or crystalline form is substantially water soluble, the particle size can be adjusted by milling to provide a substantially uniform distribution in the formulation, e.g., about 40 mesh.

The salts and crystalline forms described herein may be milled using known milling procedures such as wet milling to obtain a particle size appropriate for tablet formation and for other formulation types. Finely divided (e.g., nanoparticulate) preparations of the salts and crystalline forms described herein can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The salts and crystalline forms described herein can be formulated so as to provide quick, sustained or delayed release of the active ingredient after administration to the patient by employing procedures known in the art.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

The compositions can be formulated in a unit dosage form, each dosage containing from about 5 to about 1,000 mg (1 g), more usually about 100 mg to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient. The doses described can be the specified amount of the particular salt or crystalline form, or an amount of the particular salt or crystalline form that provides the specified dose of the free base compound (namely N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide).

In some embodiments, the compositions of the invention contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient. The doses described can be the specified amount of the particular salt or crystalline form, or an amount of the particular salt or crystalline form that provides the specified dose of the free base compound (namely N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide).

In some embodiments, the compositions of the invention contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient. The doses described can be the specified amount of the particular salt or crystalline form, or an amount of the particular salt or crystalline form that provides the specified dose of the free base compound (namely N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide).

The doses specified may be given once a day, or if necessary, be given several times a day, e.g., two times, three times, or four times a day.

The active compound may be effective over a wide dosage range and is generally administered in a pharmaceutically effective amount. It will be understood, however, that the dose actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a salt or crystalline form as described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient.

The tablets or pills containing the salt or crystalline forms described herein can be coated or otherwise compounded to provide a dosage form affording the advantage of prolonged action. Coated tablets may be prepared by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly, the tablet coating may consist of a number of layers to achieve delayed release, possibly using the excipients mentioned above for the tablets.

For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the salts, crystalline forms and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles. Although liquid formulations in which the salt is dissolved will generally not contain the salt in crystalline form, the salts and crystalline forms described herein will nevertheless be useful for preparing liquid formulations, e.g., by dissolving the salt or crystalline form thereof in a suitable medium.

Solutions for injection and infusion can be prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices that deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1 wt %, at least about 0.25 wt %, at least about 0.5 wt %, at least about 1 wt %, at least about 2 wt %, or at least about 5 wt % of the compound of the invention. The topical formulations can be suitably packaged in tubes of, for example, 100 g, which are optionally associated with instructions for the treatment of the select indication, e.g., psoriasis or other skin condition.

The amount of the salt or crystalline form or composition thereof administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1% to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

It is expected that suitable doses for administration to a human will be in the range from about 50 mg to about 2000 mg, e.g., from about 100 mg to about 2000 mg, about 200 mg to about 2000 mg, about 400 mg to about 2000 mg, about 600 mg to about 2000 mg, about 800 mg to about 2000 mg, about 1000 mg to about 2000 mg, about 1200 mg to about 2000 mg, about 1400 mg to about 2000 mg, about 1500 mg to about 2000 mg, about 1600 mg to about 2000 mg, about 1800 mg to about 2000 mg, from about 50 mg to about 1500 mg, from about 100 mg to about 1500 mg, about 200 mg to about 1500 mg, about 400 mg to about 1500 mg, about 600 mg to about 1500 mg, about 800 mg to about 1500 mg, about 1000 mg to about 1500 mg, about 1200 mg to about 1500 mg, about 1250 mg to about 1500 mg, about 50 mg to about 1000 mg, from about 100 mg to about 1000 mg, about 200 mg to about 1000 mg, about 400 mg to about 1000 mg, about 600 mg to about 1000 mg, about 800 mg to about 1000 mg, from about 50 mg to about 500 mg, from about 100 mg to about 500 mg, about 200 mg to about 500 mg, about 400 mg to about 500 mg, or a dose of about 50 mg, about 100 mg, about 150 mg, about 200 mg, about 250 mg, about 300 mg, about 350 mg, about 400 mg, about 450 mg, about 500 mg, about 600 mg, about 700 mg, about 750 mg, about 800 mg, about 900 mg, about 1000 mg, about 1200 mg, about 1400 mg, about 1500 mg, about 1600 mg, about 1800 mg or about 2000 mg. The suitable dose as specified may the dose of the salt itself, or a dose of the salt that provides the specified amount of the free base compound (namely N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide).

The compositions of the invention can further include one or more additional pharmaceutical agents such as a chemotherapeutic, steroid, anti-inflammatory compound, or immunosuppressant, examples of which are listed hereinabove.

The formulation examples which follow illustrate the present invention without restricting its scope:

Examples of Pharmaceutical Formulations

| A) Tablets | per tablet |
| --- | --- |
| salt or crystalline form of the compound | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
| --- | --- |
| salt or crystalline form of the compound | 80 mg |
| lactose | 55 mg |
| corn starch | 190 mg |
| microcrystalline cellulose | 35 mg |
| polyvinylpyrrolidone | 15 mg |
| sodiumcarboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

V. Kits

The present invention also includes pharmaceutical kits useful, for example, in the treatment or prevention of B-RAF-associated diseases or disorders, such as cancer, which include one or more containers containing a pharmaceutical composition comprising a therapeutically effective amount of a salt or crystalline form as described herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

EXAMPLES

General Methods

In the examples below, except as otherwise indicated, X-Ray Powder Diffraction analysis was carried out on a STOE STADI powder diffractometer in transmission mode fitted with a position-sensitive detector (PSD) and a Cu-anode as X-ray source with monochromated CuKα1 radiation. ($\lambda$=1.54056 Å, 40 kV, 40 mA). General measurement conditions were:
  Start Angle—3°
  Stop Angle—40°
  Sampling—0.02 deg.
  Scan speed—10 s/step.

Differential Scanning Calorimetry (DSC) was carried out on a TA Instrument Differential Scanning Calorimetry, Model Q2000 using a sample size of 8-10 mg. The general experimental conditions were: 25-350° C. at 10° C./min.

Thermogravimetric analysis (TGA) was carried out on a TA Instrument Thermogravimetric Analyzer, Model Q5000 with the following conditions: Ramp at 10° C./min. to 350° C.

Dynamic Vapor Sorption (DVS) was performed in a IGAsorp Water Sorption Analyzer from Hiden Isochema. Adsorption and desorption isotherms were performed at 25° C. with 10% RH step intervals ranging from 0% relative humidity up to 90% relative humidity.

For HPLC-mass spectroscopy/UV-spectrometry, the retention times/MS-ESI⁺ for characterizing the example compounds according to the invention are produced using an HPLC-MS apparatus (high performance liquid chromatography with mass detector). Compounds that elute at the injection peak are given the retention time $t_{Ret.}$=0.00. Methods described in the Examples below are as follows.

HPLC-MS Method A
HPLC: Agilent 1100 Series
MS: Agilent LC/MSD SL
Column: Waters, XBridge™ C18, 5 µm, 2.1×50 mm
Eluent: A: $H_2O$ (5 mM $(NH_4)_2CO_3$, 19 mM $NH_3$)
  B: Acetonitrile HPLC grade
Detection: MS: Positive and negative mode
Mass Range: 120-800 m/z
Flow: 1.20 mL/min.
Column temperature: rt

| Gradient: | |
|---|---|
| 0.00 min. | 5% B |
| 0.00-1.25 min. | 5% → 95% B |
| 1.25-2.00 min. | 95% B |

HPLC-MS Method B
HPLC: Agilent 1100 Series
MS: Agilent LC/MSD SL
Column: Waters, XBridge™ C18, 2.5 µm, 2.1×20 mm
Eluent: A: $H_2O$ (0.1% $NH_3$)
  B: Acetonitrile HPLC grade
Detection: MS: Positive and negative mode
Mass Range: 120-800 m/z
Flow: 1.00 mL/min.
Column temperature: 60° C.

| Gradient: | |
|---|---|
| 0.00 min. | 5% B |
| 0.00-2.50 min. | 5% → 95% B |
| 2.50-2.80 min. | 95% B |

HPLC-MS Method C
HPLC: Agilent 1100 Series
MS: Agilent LC/MSD SL
Column: Waters, Sunfire™ C18, 5 µm, 2.1×50 mm
Eluent: A: $H_2O$ (0.2% HCOOH)
  B: Acetonitrile HPLC grade (0.2% HCOOH)
Detection: MS: Positive and negative mode
Mass Range: 120-800 m/z
Flow: 1.20 mL/min.
Column temperature: rt

| Gradient: | |
|---|---|
| 0.00 min. | 5% B |
| 0.00-1.50 min. | 5% → 95% B |
| 1.50-2.00 min. | 95% B |

Equilibrium Solubility Measurements

Saturated solutions are prepared in well plates by adding an appropriate volume of selected aqueous media (typically in the range of 0.25-1.5 mL) into each well which contains a known quantity of solid drug substance (typically in the range 0.5-5.0 mg). The wells are shaken or stirred for a predefined time period (typically in a range of 2-24 h) and then filtered using appropriate filter membranes (typically PTFE-filters with 0.45 µm pore size). Filter absorption is avoided by discarding the first few drops of filtrate. The amount of dissolved drug substance is determined by UV spectroscopy. In addition, the pH of the aqueous saturated solution is measured using a glass-electrode pH meter.

Intrinsic Dissolution Rate Measurements

The intrinsic dissolution rate of 3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide salts was determined in aqueous media covering a range of pH 1.1-7.4 using the rotating disc method which maintains a constant surface area.

The drug substance (5 mg) was compressed at 356.1 Newtons for 60 s to form a disk. These disks were mounted to sample holders which fit into a miniaturized dissolution testing apparatus. The dissolution media were stirred at 200 rpm at a temperature of 37° C. Samples were automatically withdrawn every second minute from the dissolution vessel and assayed by UV spectrophotometry.

Preparation of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide (BI 882370)

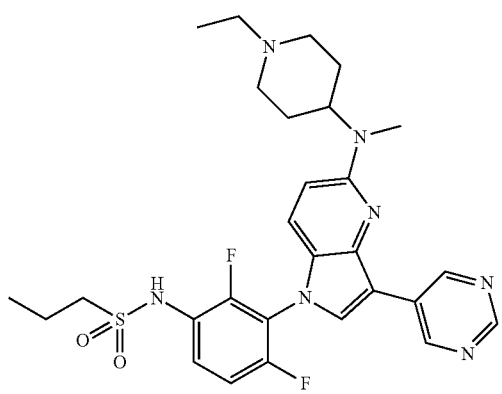 [SMILES: CCCS(=O)(=O)Nc1ccc(F)c(-n2cc(-c3cncnc3)c3nc(N(C)C4CCN(CC)CC4)ccc32)c1F]

Step 1. 4-(6-Methyl-5-nitro-pyridin-2-yl)-piperazine-1-carboxylic acid tert-butyl ester (3)

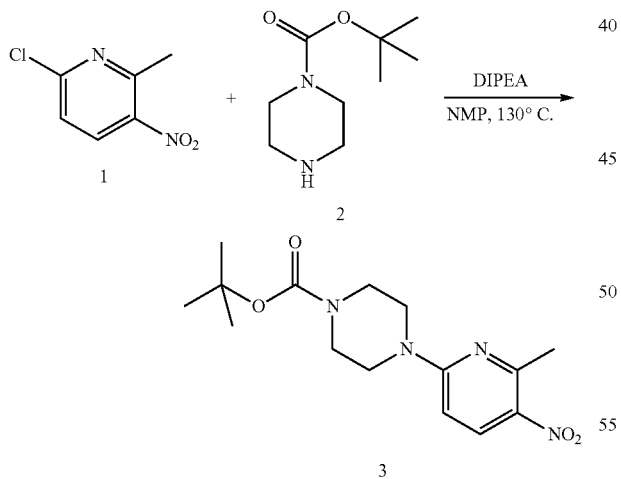

DIPEA (62.82 mL, 0.435 mol) is added to the solution of 6-chloro-3-nitro-2-methylpyridine (1) (50 g, 290 mmol) and N-Boc-piperazine (2) (53.95 g, 290 mmol) in dry MeCN (200 mL) and stirred for 4 h at 50° C. After the reaction is finished the reaction mixture is diluted with MeCN and water and stirred for 30 min. The precipitated product is collected by filtration, washed with water and the solid is dried in vacuo.

Step 2. 4-[6-((E)-2-Dimethylamino-vinyl)-5-nitro-pyridin-2-yl]-piperazine-1-carboxylic acid tert-butyl ester (4)

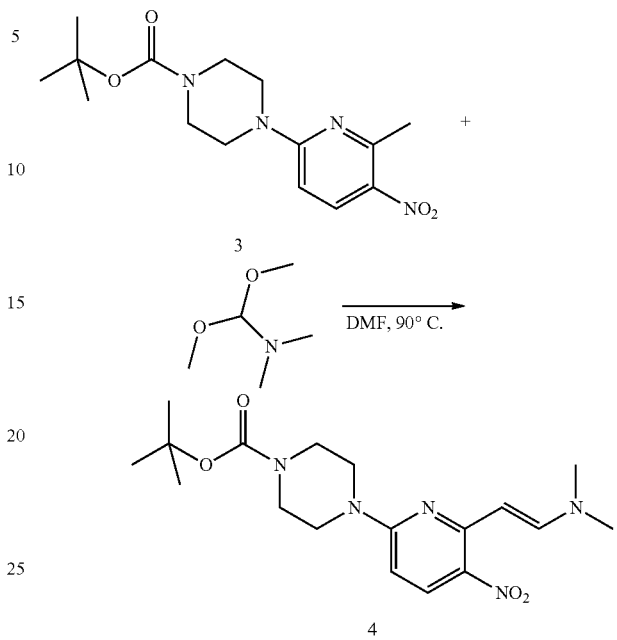

To a stirred solution of 4-(6-methyl-5-nitro-pyridin-2-yl)-piperazine-1-carboxylic acid tert-butyl ester (3) (13 g, 40.3 mmol) in DMF (35 mL) is added N,N-dimethylformamide dimethylacetal (14.47 g, 121 mmol) and stirred in argon atmosphere for 36 h at 90° C. Additional 1.5 eq. of N,N-dimethylformamide dimethylacetal is added and stirred for 12 h at 90° C. The reaction mixture is poured into water and extracted with DCM. The combined organic layers are washed with water, dried over anhydrous $Na_2SO_4$ and concentrated in vacuo. The residue is used without further purification for the next step.

Step 3. 4-(1H-pyrrolo[3,2-b]pyridin-5-yl)piperazine-1-carboxylic acid tert-butyl ester (5)

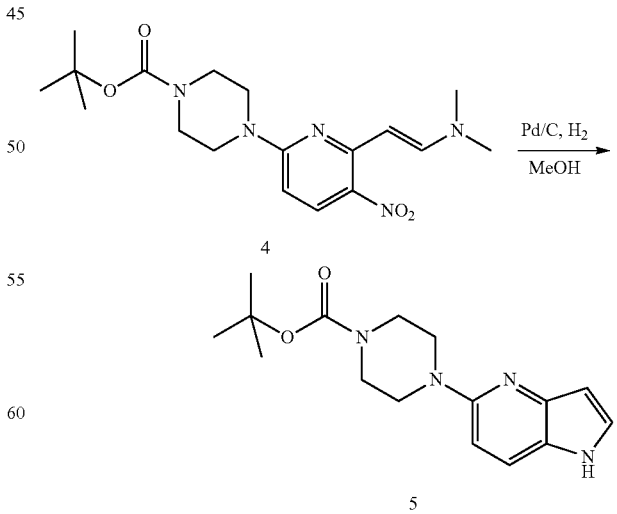

4-[6-((E)-2-Dimethylamino-vinyl)-5-nitro-pyridin-2-yl]-piperazine-1-carboxylic acid tert-butyl ester (36.4 g, 96 mmol) is taken up in MeOH, Pd/C (0.56 g, 10%) is added and the mixture is hydrogenated in an autoclave at 60 psi for 16 h. The reaction mixture is filtered and concentrated under reduced pressure. The residue is purified by column chromatography via NP MPLC. The product containing fractions of compound (5) (HPLC-MS method B: $t_{Ret.}$=1.55 min.; MS $(M+H)^+$=303) are combined and evaporated in vacuo.

Step 4. N-(3-Amino-2,6-difluorophenyl)acetamide (7)

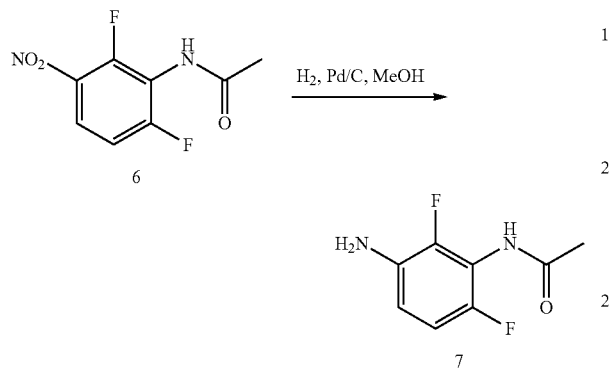

Compound (6) (55.0 g, 254 mmol) is taken-up in MeOH (1.0 L). Pd/C (10.0 g, 10%) is added and the mixture is hydrogenated in an autoclave at 200 psi for 3 h. The reaction mixture is filtered and concentrated under reduced pressure. The residue is purified by NP-MPLC on silica gel using DCM/MeOH (96:4) as eluent. The product containing fractions of the aniline intermediate (HPLC-MS method B: $t_{Ret.}$=0.25 min.; MS $(M-H)^-$=185) are combined and evaporated.

Step 5. N-(2,6-Difluoro-3-(propylsulfonamido)phenyl)acetamide (9)

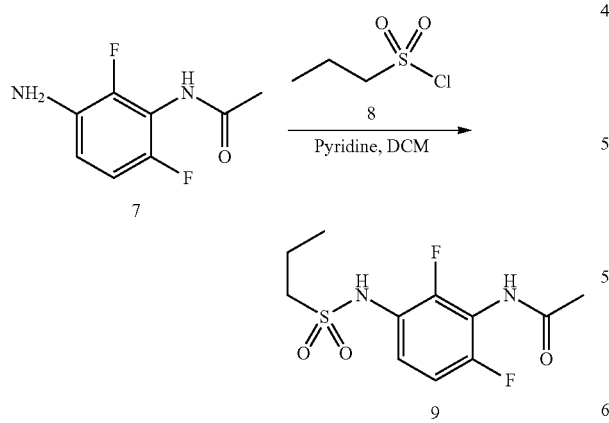

To the aniline intermediate (35.0 g, 188 mmol) in DCM (100 mL) pyridine (6.6 mL, 75 mmol) and n-propane sulfonyl chloride (8) (29.5 mL, 263 mmol) are added and the mixture is stirred at rt for 16 h. The reaction mixture is diluted with EtOAc (200 mL), washed with H₂O and HCl (aq., 1 N) and the layers are separated, dried over MgSO₄ and evaporated to yield the sulfonamide (9) which was used without further purification.

Step 6. N-(3-Amino-2,4-difluorophenyl)propane-1-sulfonamide (10)

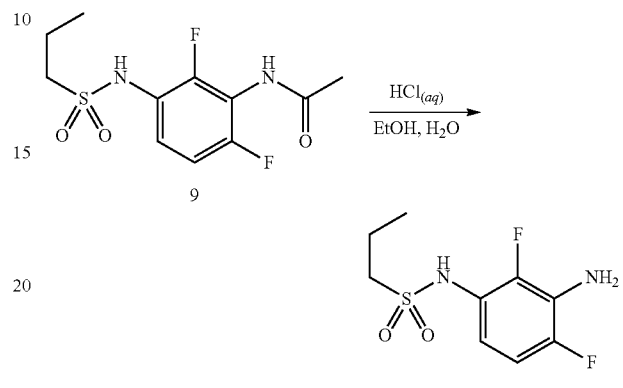

The sulfonylated aniline (9) (38.0 g, 130 mmol) is taken-up in EtOH (250 mL), H₂O (200 mL) and concentrated hydrochloric acid (200 mL) and heated to 80° C. for 2 h. The reaction mixture is concentrated under reduced pressure, aqueous NaOH (4 N) is added until pH=6 is reached and the mixture is extracted 2× with DCM. The combined organic layer is washed with brine, dried over MgSO₄, filtered and evaporated to yield the deacylated aniline (10) (HPLC-MS method B: $t_{Ret.}$=0.22 min.; MS $(M-H)^-$=249) as a hydrochloride which was used without further purification.

Step 7. N-(2,4-Difluoro-3-iodophenyl)propane-1-sulfonamide (11)

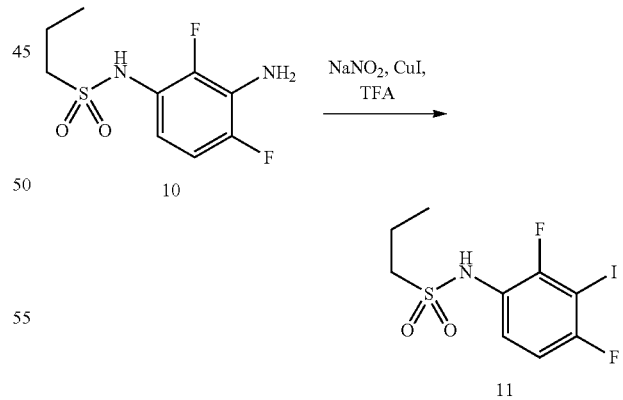

The hydrochloride of compound (10) is taken-up in DCM and extracted with NaHCO₃ solution. The organic layer is dried over MgSO₄, filtered and evaporated. To the free base (10) (3.55 g, 14.21 mmol) in TFA (80 mL) at 0° C. is added NaNO₂ (1.96 g, 28.4 mmol) in small portions and the mixture is stirred for 30 min. KI (23.83 g, 142 mmol) is added and stirring is continued for additional 15 min. The reaction mixture is diluted with Et₂O and stirred for 1 h. Na₂S₂O₃ solution (semiconc.) is added and the mixture is extracted 3× with Et₂O. The combined organic layer is dried over MgSO₄, filtered and concentrated in vacuo. The residue is purified by column chromatography via NP-MPLC. The product containing fractions of compound (11) (HPLC-MS method A: $t_{Ret.}$=1.58 min.; MS (M–H)⁻=360) are combined and evaporated in vacuo.

Step 8. 4-((1-(2,6-Difluoro-3-(propylsulfonamido)phenyl)-1H-pyrrolo[3,2-b]pyridin-5-yl)(methyl)amino)piperidine-1-carboxylic acid tert-butyl ester (12)

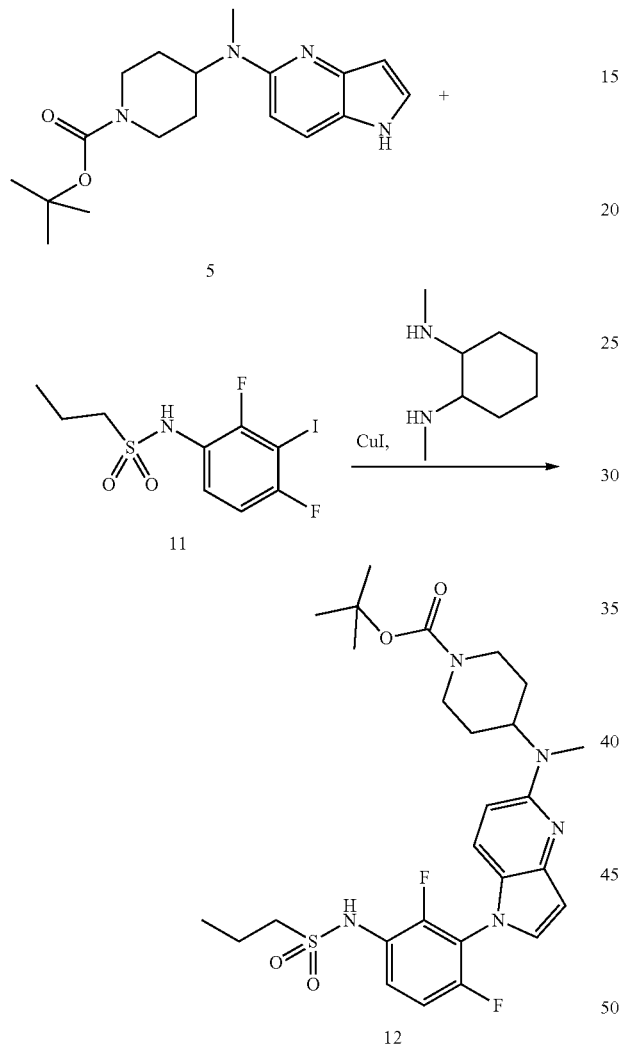

The 1H-pyrrolo[3,2-b]pyridine (5) (10.0 g, 30.27 mmol), sulfonamide (11) (16.4 g, 45.4 mmol), CuI (576 mg, 3.03 mmol), trans-(1R,2R)—N,N'-bismethyl-1,2-cyclohexandiamine (1.91 mL, 12.1 mmol) and Cs₂CO₃ (29.6 g, 90.85 mmol) are taken-up in dry toluene (3 mL) and the resulting mixture is flushed with argon and stirred for 16 h at 120° C. After the addition of further CuI (576 mg, 3.03 mmol), trans-(1R,2R)—N,N'-bismethyl-1,2-cyclohexandiamine (1.91 mL, 12.1 mmol) and Cs₂CO₃ (20.0 g, 60.0 mmol) the reaction mixture is stirred for further 24 h. The solvent is removed in vacuo, the residue is taken up in DCM and extracted with NaHCO₃ solution (semiconc.). The organic layer is dried over MgSO₄, filtered, the solvent is removed in vacuo and the residue is purified via NP-MPLC. The product containing fractions of (12) (HPLC-MS method C: $t_{Ret.}$=1.62 min.; MS (M+H)⁺=564) are combined and the solvent is removed in vacuo.

Step 9. 4-((1-(2,6-Difluoro-3-(propylsulfonamido)phenyl)-3-iodo-1H-pyrrolo[3,2-b]pyridin-5-yl)(methyl)amino)piperidine-1-carboxylic acid tert-butyl ester (13)

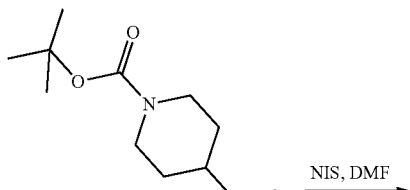

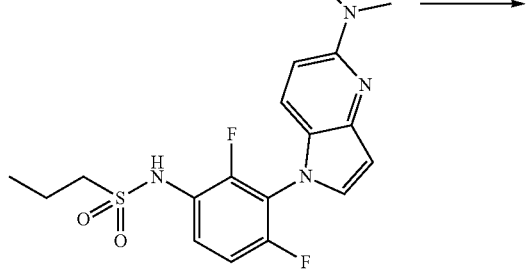

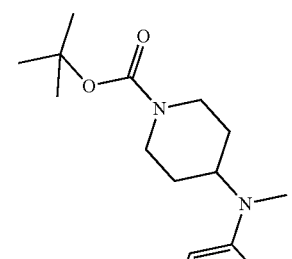

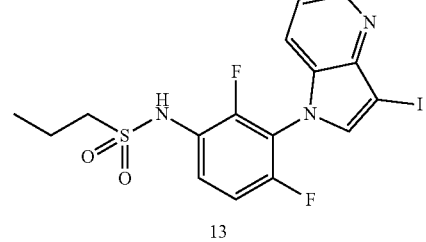

To a solution of sulfonamide (12) (1.078 g, 1.9 mmol) in DMF (4 mL)/THF (100 μL) is added NIS (474 mg, 2.1 mmol) and the mixture is stirred for 1 h at rt. The reaction mixture is diluted with 30 mL DCM and extracted with NaHCO₃ solution (semiconc.). The combined organic layer is dried over MgSO₄, filtered and concentrated under reduced pressure. The residue is purified by column chromatography via RP HPLC. The product containing fractions of (13) (HPLC-MS method B: $t_{Ret.}$=2.035 min.; MS (M+H)⁺=688) are freeze dried.

Step 10. 4-((1-(2,6-Difluoro-3-(propylsulfonamido)phenyl)-3-(pyrimidin-5-yl)-1H-pyrrolo[3,2-b]pyridin-5-yl)(methyl)amino)piperidine-1-carboxylic acid tert-butyl ester (15)

Step 11. N-(2,4-Difluoro-3-(5-(methyl(piperidin-4-yl)amino)-3-(pyrimidin-5-yl)-1H-pyrrolo[3,2-b]pyridin-1-yl)phenyl)propane-1-sulfonamide

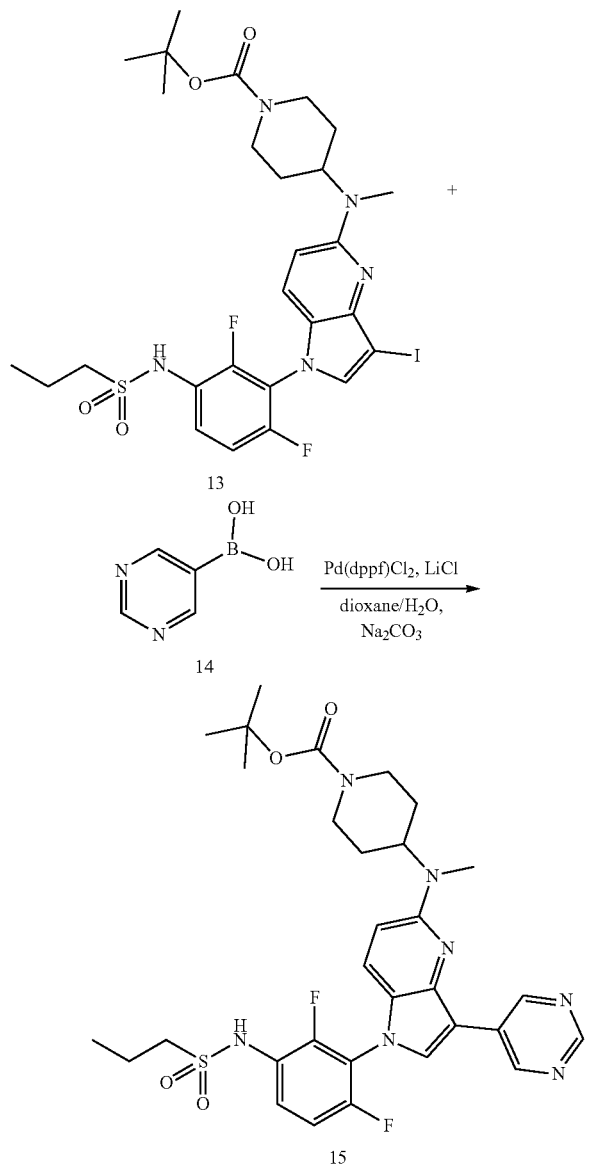

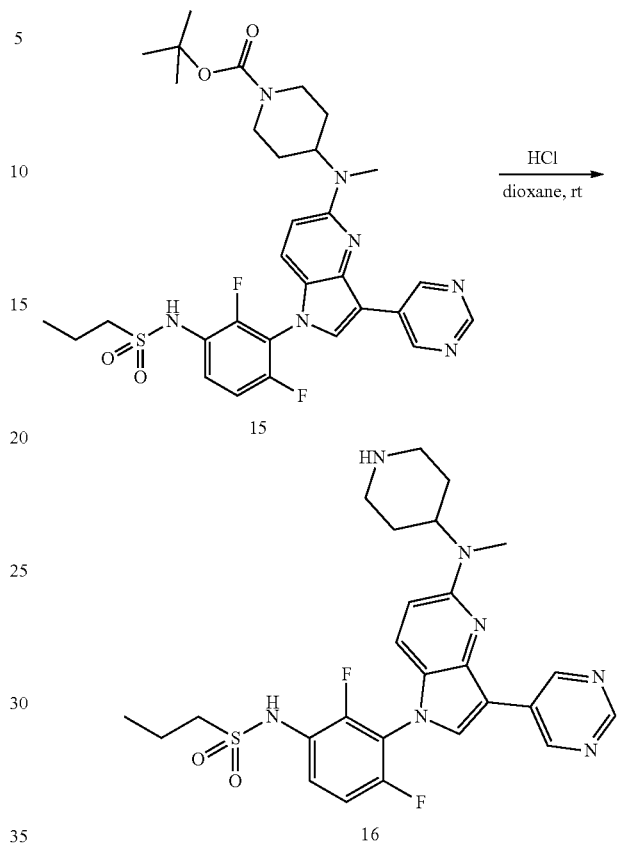

To a solution of example compound (15) (154 mg, 0.24 mmol) in DCM/MeOH (1:1, 4 mL) is added HCl (in dioxane, 4 N, 2 mL) and the mixture is stirred for 3 h at rt. The solvent is removed in vacuo. Obtained compound (16) (HPLC-MS method B: $t_{Ret.}$=1.02 min.; MS (M+H)$^+$=542) is used without further purification.

Step 12. N-(3-(5-(((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide (I)

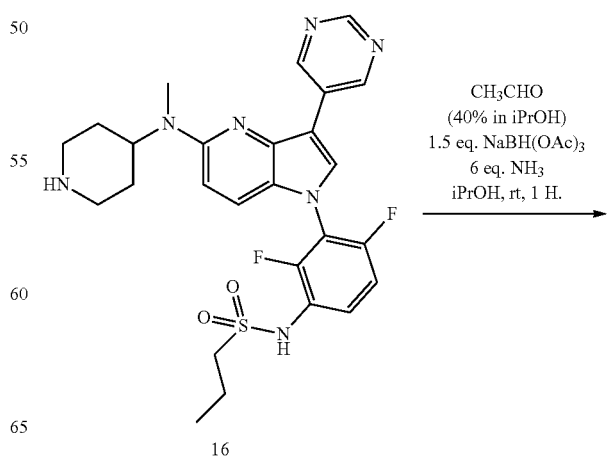

Sulfonamide (13) (770 mg, 1.12 mmol), pyrimidin-5-yl-boronic acid (14) (194 mg, 1.57 mmol), Pd(dppf)Cl$_2$ (82 mg, 0.11 mmol), LiCl (142 mg, 3.35 mmol) and Na$_2$CO$_3$ (294 mg, 2.8 mmol) are taken-up in dioxane/H$_2$O (2:1 mixture, 12 mL), and the resulting mixture is flushed with argon and stirred for 1 h at 100° C. The reaction mixture is diluted with DCM and extracted with NaHCO$_3$ solution (semi-concentrated). The organic layer is dried over MgSO$_4$, filtered, Isolute® is added, the solvent is removed in vacuo and the residue is purified via RP HPLC. The product containing fractions of (15) (HPLC-MS method C: $t_{Ret.}$=2.149 min.; MS (M+H)$^+$=642) are freeze dried.

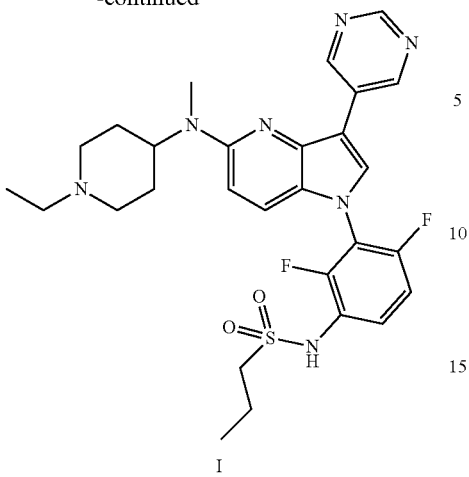

I

Compound I was obtained from compound (16) by reductive alkylation with acetaldehyde (40% in iPrOH) in the presence of 1.5 eq. sodium acetoxyborohydride in iPrOH. The crude product was recrystallized from ethanol to obtain the title compound in 84% yield.

Scale-Up Synthesis of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide (BI 882370)

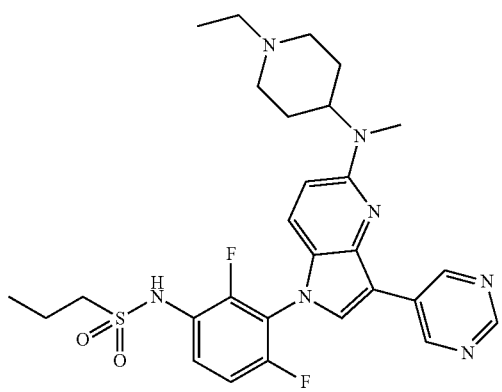 [SMILES: CCCS(=O)(=O)Nc1ccc(F)c(-n2cc(-c3cncnc3)c3nc(N(C)C4CCN(CC)CC4)ccc32)c1F]

15

Step 1. N-(2,4-Difluoro-3-(5-(methyl(piperidin-4-yl)amino)-3-(pyrimidin-5-yl)-1H-pyrrolo[3,2-b]pyridin-1-yl)phenyl)propane-1-sulfonamide

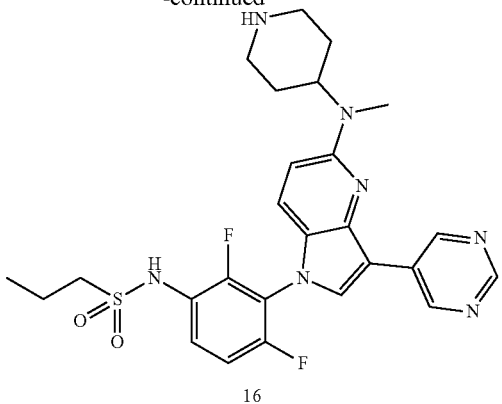

Isopropanol (8.83 kg) and compound (15) (1.80 kg, 2.8 mol) were added into a reactor, and the mixture was stirred and heated to 55~60° C. Concentrated hydrochloric acid (2.76 kg, 28 mol) was dropped into the reactor over than 20 min. at 60-65° C. Then, the reaction mass was heated to 60-70° C. and held for 1 h. The conversion was monitored by HPLC, and reached about 99.5% after about 1 h.

The reaction mass was cooled and the isopropanol was removed by distillation under reduced pressure at not more than 50° C. A brown oil was obtained, dissolved into water (6.75 kg) and washed by extraction with ethyl acetate (2.02 kg) at 20-30° C. The water-phase was cooled to 15-20° C. The pH was adjusted to 8.0-8.5 with 10% aqueous NaOH solution (~8.0 kg) at 20-30° C. The mixture was stirred for 3-4 h at 20-30° C. with the pH adjusted to 8.0-8.5 by addition of 10% NaOH solution every half-hour. The product was isolated by filtration and the cake washed with water (3.6 kg). The solid was dried under vacuum at 45~50 until the water content was not more than 5.5%. This provided about 1.64 kg of crude compound (16) (yield 108% of theoretical; the crude product containing water and NaCl detected). The crude product was used directly).

Step 12. N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide (I)

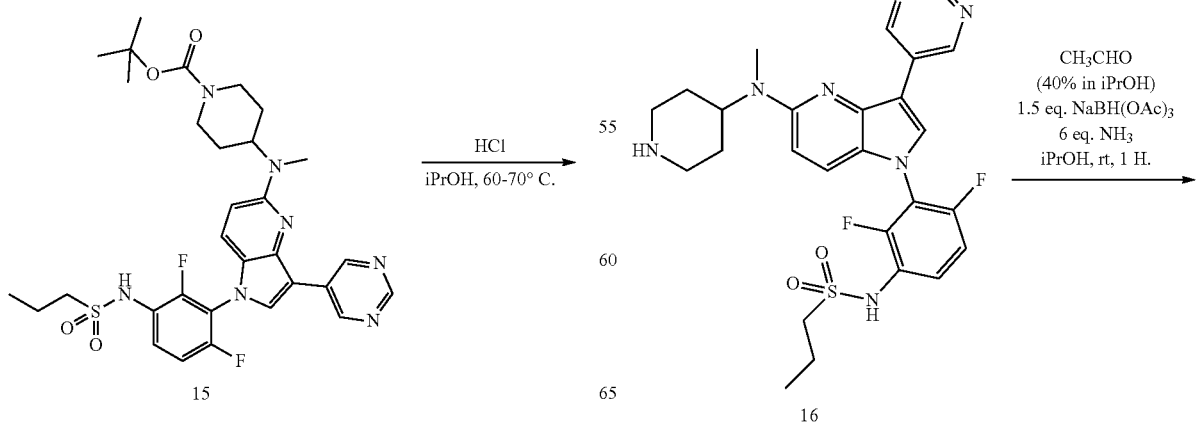

-continued

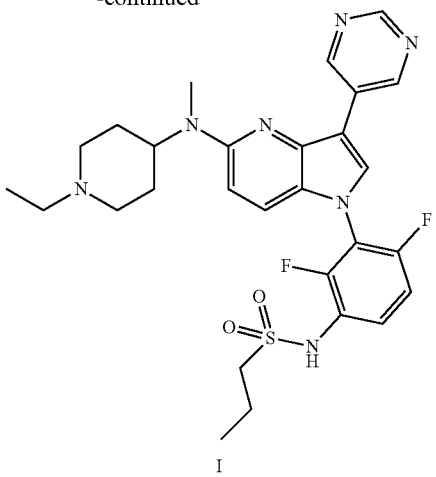

I 2 h at 0-10° C. The reaction mixture was stirred at 0~10° C. under a nitrogen atmosphere for 0.5-1 h. The conversion was monitored by HPLC, and reached about 99.5% after about 0.5-1 h.

Water (15 kg) was added into the reaction mass at a temperature below 15° C. The mixture was stirred at 15-30° C. for 20~30 min. Aqueous ammonia (25%, 1.13 kg, 16.61 mol) was added into the mixture and the mixture was then stirred for 0.5 h. The organic phase was separated and then washed by extraction with water (15 kg) at 20-25° C. Activated charcoal (0.15 kg) was added into the organic phase. The mixture was stirred for 1 h and then filtered. The filtrate was concentrated under reduced pressure at not more than 40° C., and compound (I) (1.58 kg, 100% yield) was obtained as a foamy solid.

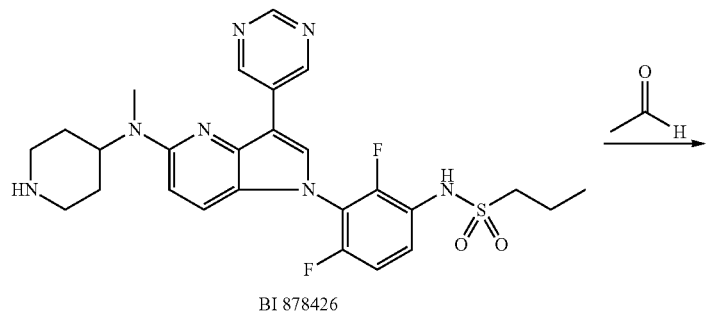

BI 878426

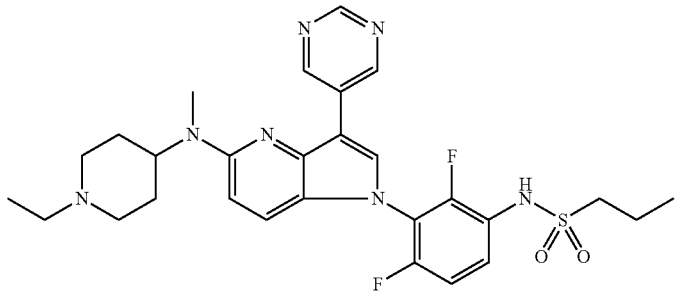

BI 882370

| Name | Molecular Weight | Mole | Weight | Ratio | Supplier |
| --- | --- | --- | --- | --- | --- |
| BI 878426 | 541.62 | 2.77 mol | 1.50 kg | 1.0 eq | Bioduro |
| STAB (95%) | 211.94 | 4.16 mol | 0.93 kg | 1.5 eq | |
| Dichloromethane | N/A | N/A | 19.88 kg | 10.0 v | |
| 40% Acetaldehyde in DCM | 44.05 | 9.71 mol | 1.07 kg | 3.5 eq | |
| $H_2O$ | N/A | N/A | 30.0 kg | 20.0 v | |
| Ammonia | 17.03 | 16.61 mol | 1.13 kg | 6.0 eq | |
| Medicinal Carbon | N/A | N/A | 0.15 kg | 10.0% | |

Process:

Dichloromethane (19.88 kg) and compound (16) (1.5 kg, 2.77 mol) were added into a reactor, and the mixture was stirred and cooled to 0-10° C. under a nitrogen atmosphere. Sodium triacetoxyborohydride (95%, 0.93 kg, 4.16 mol) was added into the mixture at 0-10° C. The mixture was stirred for 20-30 min. at 0-10° C. Acetaldehyde in DCM (40%, 1.07 kg, 9.71 mol) added into the mixture slowly over Investigation of the Crystallinity of N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide Free Base Investigation of the crystallinity of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide free base, obtained by recrystallization from aqueous ethanol, which was used as a starting material to investigate salt formation showed that the compound had low crystallinity, as seen in FIG. 1.

Investigation of Salt Forms of N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide The compound N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide was combined with various acids in various solvent systems.

A 96-well master plate was charged by dosing compound in MeOH (stock solution) with a concentration of approx. 40 mg/mL. This plate was placed in a vacuum oven for liquid removal to obtain the same amount of solid material in each well. Subsequently different solvents/solvent mixtures and the acids were added to the solid material in each well (approx. 500 µL) and the whole plate was heated up to 50° C. for 2 hours while stirring (using a small stirring bar added to each well).

The acids used were as shown in Table 1. The solvents used were as shown in Table 2. Crystallinity of salts obtained either by the slurry experiment or crystallization by evaporation.

Figure 2A:
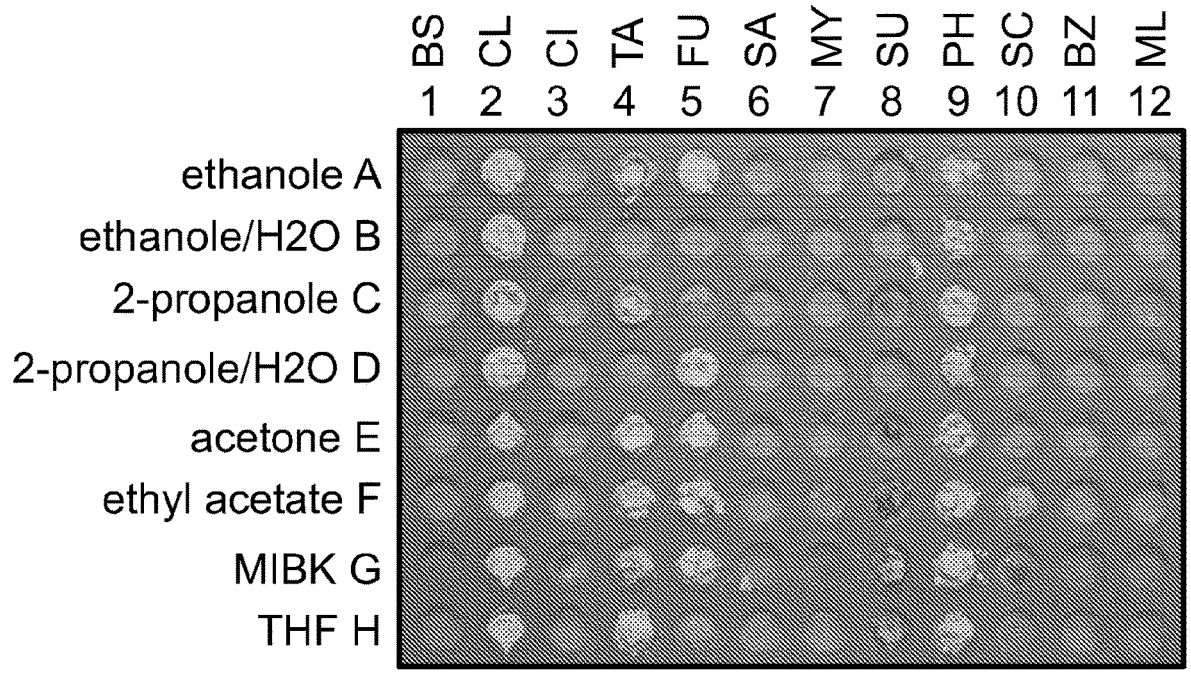
FIG. 2A is an image of a master plate showing salts of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide prepared with various acids and solvents and prepared via crystallization in a slurry experiment.
Figure 2B:
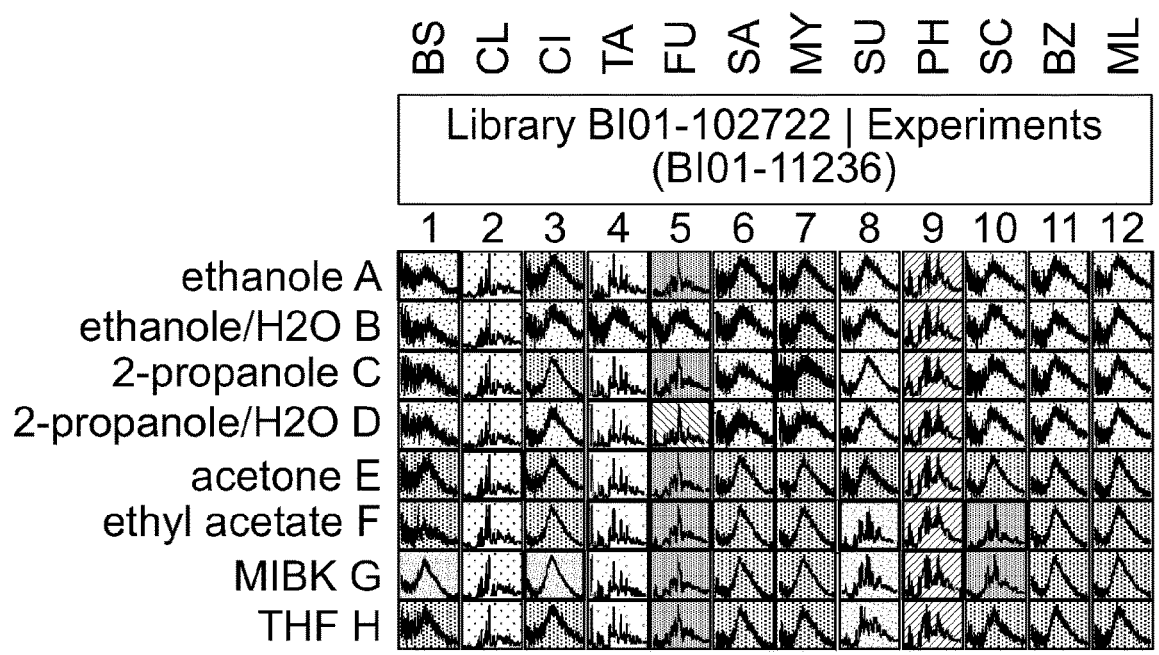
FIG. 2B is a collection of images of XRPD scans performed on each of the master plate wells of FIG. 2A, showing the crystallinity of salts of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide prepared by slurrying with various acids and solvents.

To investigate crystal formation by a slurry experiment, the plate was allowed to cool and the crystallinity of the resulting salts was investigated by XRPD. An image of the master plate showing the salts obtained is shown in FIG. 2A and images of XRPD performed on the salt from each of the master plate wells, showing the crystallinity of the salts formed, is shown in FIG. 2B.

Figure 3A:
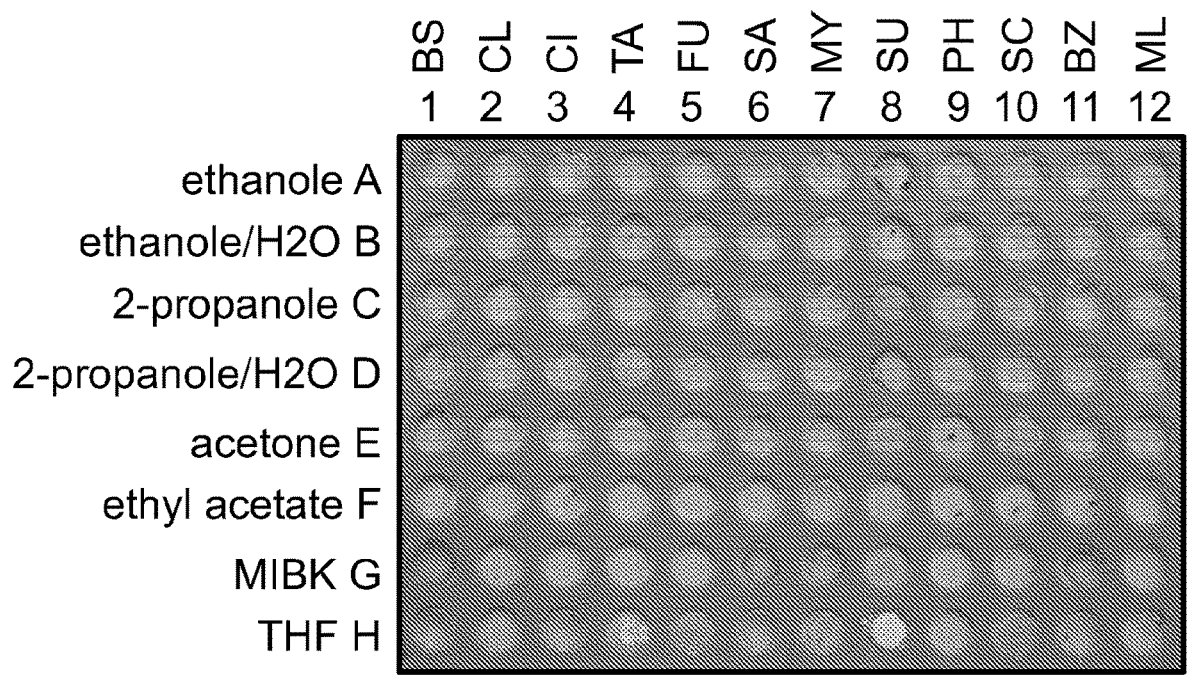
FIG. 3A is an image of an evaporation plate showing salts of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide prepared with various acids and solvents and prepared via crystallization in an evaporation experiment.
Figure 3B:
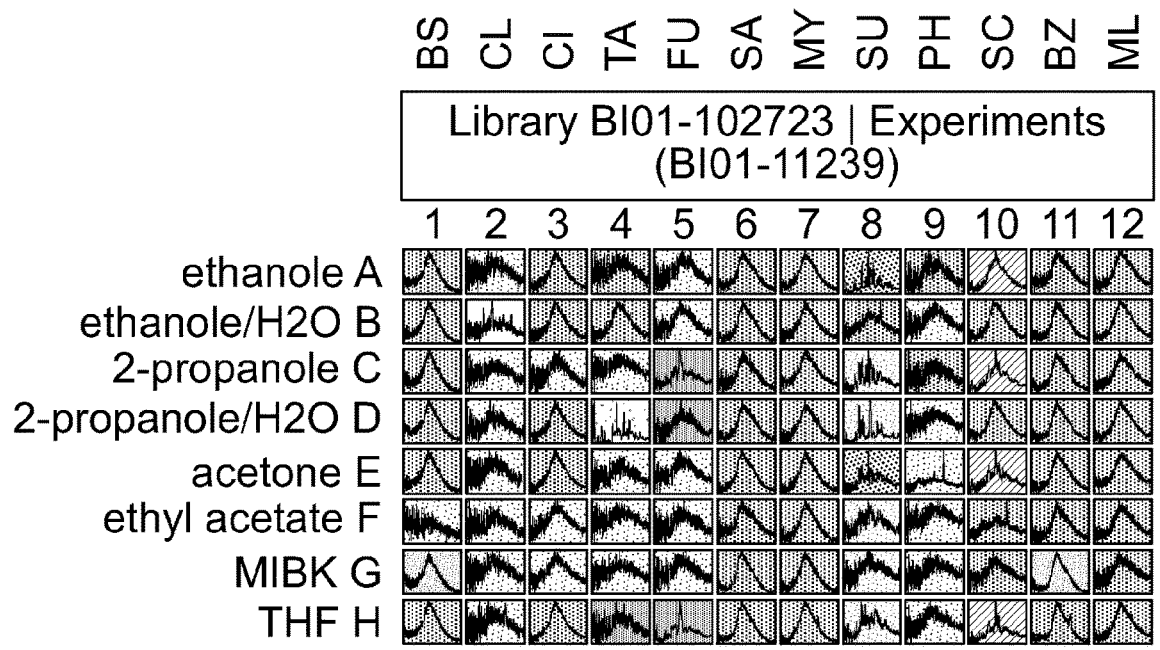
FIG. 3B is a collection of images of XRPD scans performed on each of the master plate wells of FIG. 3A, showing the crystallinity of salts of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide prepared by evaporation with various acids and solvents.

To investigate crystal formation by an evaporation experiment, after the heating period, the solutions were filtered at the same temperature (50° C.) using a preheated filter plate to ensure that no non-dissolved material can be transferred into the other crystallization plates. The filtrate was dispensed into an evaporation plate (approx. 200 µL). The solvents were allowed to evaporate, and the crystallinity of the resulting salts was investigated by XRPD. An image of the master plate showing the salts obtained is shown in FIG. 3A and images of XRPD performed on the salt from each of the evaporation plate wells, showing the crystallinity of the salts formed, is shown in FIG. 3B.

TABLE 1

Salts Used for Salt Form Investigation

| Entry | Acid (Please confirm acids used) | Code |
|---|---|---|
| 1 | Free base (No acid added) | BS |
| 2 | Hydrochloric acid | CL |
| 3 | Citric Acid | CI |
| 4 | Tartaric Acid | TA |
| 5 | Fumaric Acid | FU |
| 6 | Salicylic Acid | SA |
| 7 | R-Mandelic | MY |
| 8 | Sulfuric acid | SU |
| 9 | Phosphoric Acid | PH |
| 10 | Succinic Acid | SC |
| 11 | Benzoic Acid | BZ |
| 12 | Maleic Acid | ML |

TABLE 2

Solvents Used for Salt Form Investigation

| Entry | Solvent |
|---|---|
| A | Ethanol |
| B | Aq. Ethanol (90%) |
| C | 2-Propanol (iPrOH) |
| D | Aq. iPrOH/(90%) |
| E | Acetone |
| F | Ethyl acetate |
| G | Methyl isobuyl ketone (MIBK) |
| H | Tetrahydrofuran (THF) |

Based on the initial screening, six crystalline salts were formed, chloride (CL), fumarate (FU), phosphate (PH), succinate (SC), sulfate (SU) and tartrate (TA), as summarized in Table 3.

TABLE 3

Results of Initial Salt Form Investigation

| Salt Form | No. of Occurrences | Crystallinity | Representative Well (Master Plate) | Crystallization Solvent |
|---|---|---|---|---|
| Free Base | 0 | Amorphous | | |
| Hydrochloride | 9 | High | E2 | Acetone |
| Fumarate (form I) | 9 | Medium | F5 | Ethyl acetate |
| Fumarate (form II) | 1 | Medium | D5 | Aq. iPrOH (90%) |
| Tartrate | 8 | High | F4 | Ethyl acetate |
| Phosphate | 8 | Medium | G9 | MIBK |
| Succinate | 7 | Medium | F10 | Ethyl acetate |
| Sulfate | 8 | Medium | F8 | Ethyl acetate |

Figure 4:
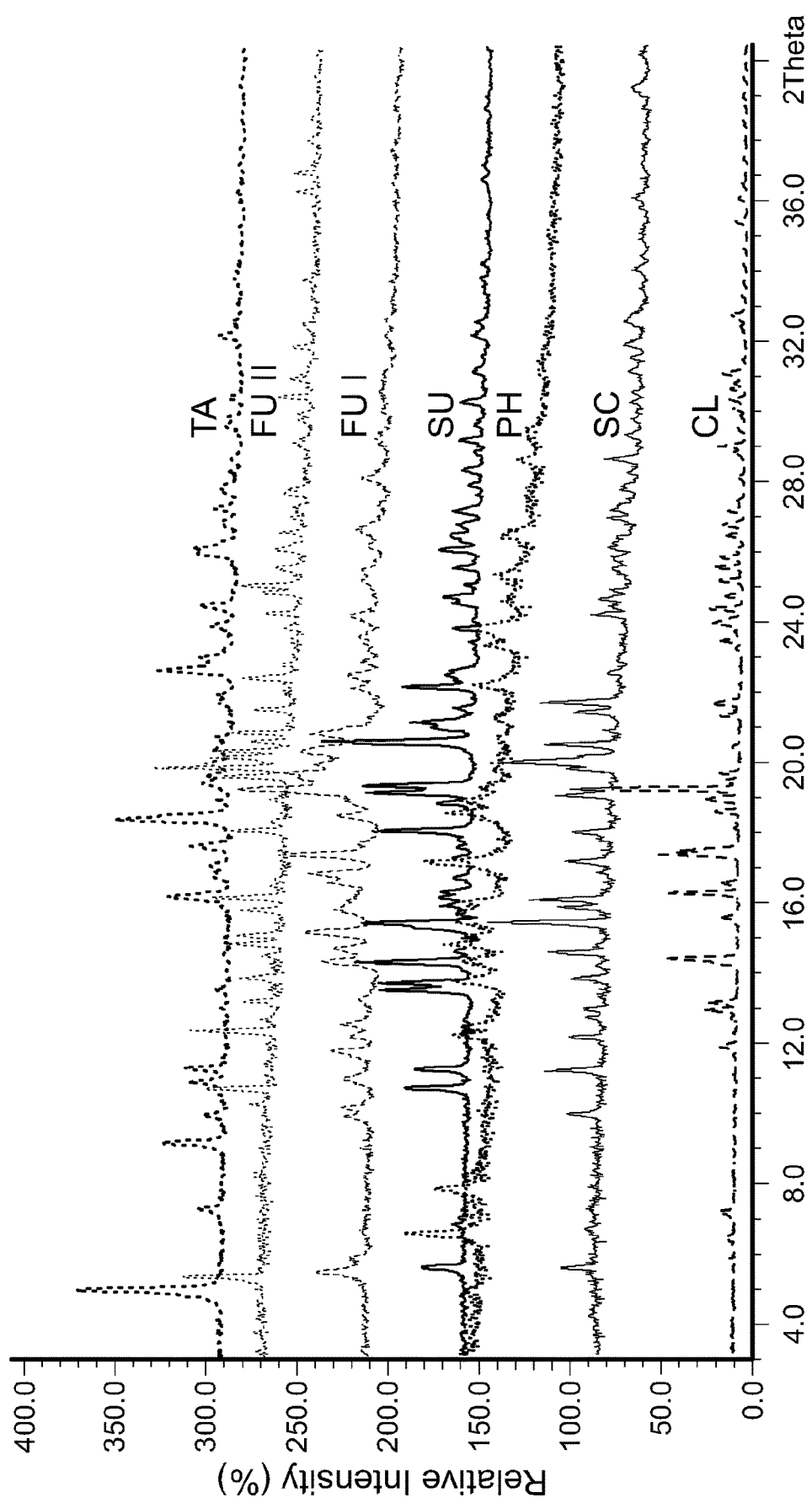
FIG. 4 is a collection of images of XRPD scans performed on samples of various crystalline salts of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide.

Images of XRPD performed on samples of each of the salt forms summarized in Table 3 are shown in FIG. 4.

Scale-Up Synthesis of Salt Forms of N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide Based on the results of the initial salt form identification, the chloride (CL), fumarate (FU), phosphate (PH), succinate (SC), sulfate (SU) and tartrate (TA) were re-synthesized on a scale of about 50 mg. Except for the phosphate, it was possible to obtain crystalline forms of each of the chloride (CL), fumarate (FU), succinate (SC), sulfate (SU) and tartrate (TA) salts as summarized in Table 4.

TABLE 4

Results of Initial Salt Form Investigation

| Salt Form | Crystallization Solvent | Crystallinity | Notes |
|---|---|---|---|
| Hydrochloride | Acetone | High | Same as hydrochloride from initial salt form investigation |
| Tartrate | Ethyl acetate | Medium | Same as tartrate from initial salt form investigation |
| Fumarate (form I) | Ethyl acetate | Medium-High | Same as Form I from initial salt form investigation |
| Fumarate (form II) | iPrOH/H2O | Amorphous | |

TABLE 4-continued

Results of Initial Salt Form Investigation

| Salt Form | Crystallization Solvent | Crystallinity | Notes |
|---|---|---|---|
| Sulfate | Ethyl acetate | High | Same as sulfate from initial salt form investigation |
| Sulfate | THF | Amorphous | |
| Phosphate | MIBK | Amorphous | Same as sulfate from initial salt form investigation |
| Succinate | Ethyl acetate | High | Ethyl acetate |

Data for N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt obtained by scale-up are shown in FIGS. 5-9.

Figure 5:
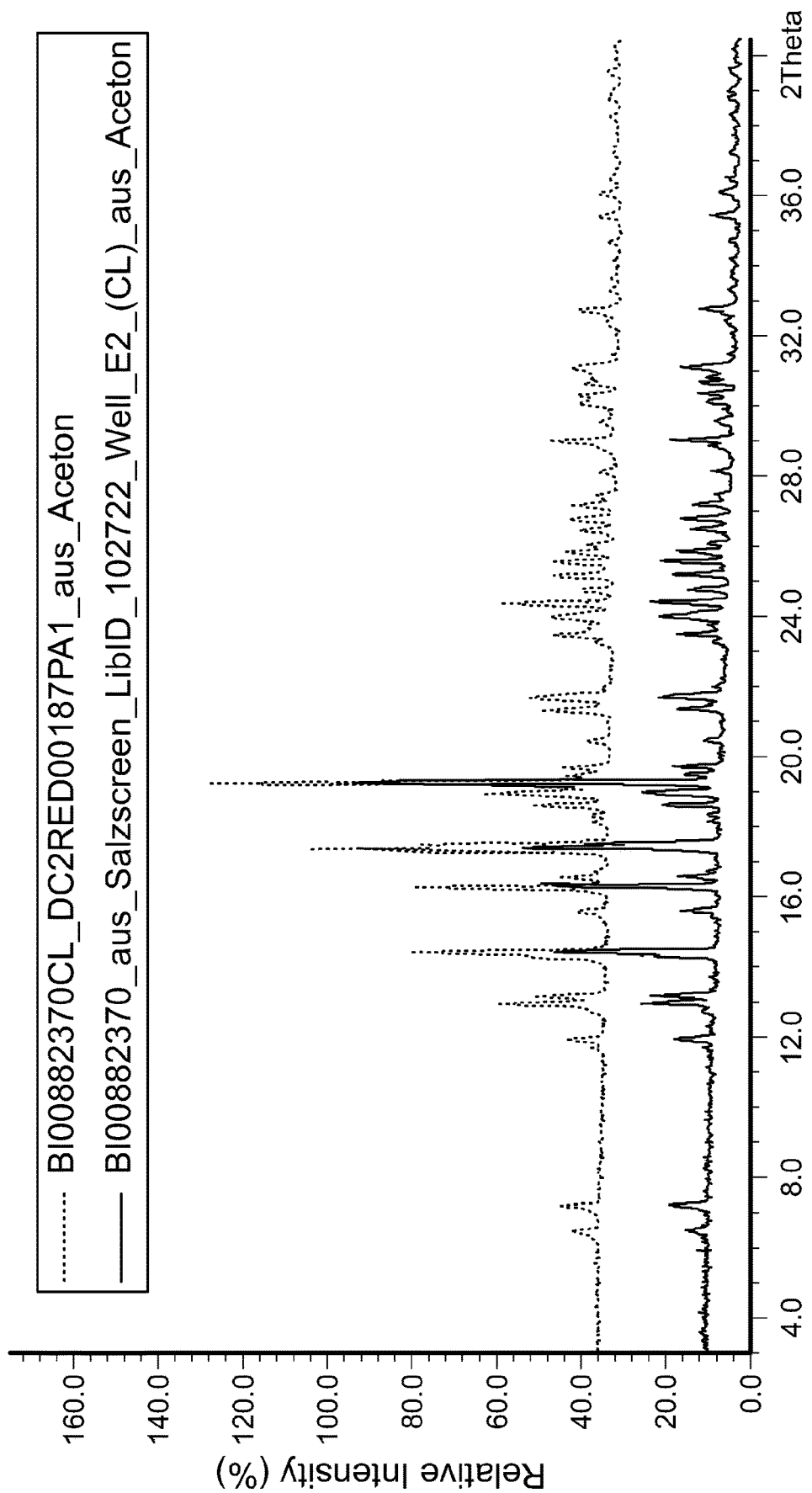
FIG. 5 is a plot of the XRPD of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt with the sample from well E2 (lower plot) compared to the sample obtained from scale-up synthesis (upper plot).

FIG. 5 is a plot of the XRPD of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt with the sample from well E2 (lower plot) compared to the sample obtained from scale-up synthesis (upper plot).

Figure 6:
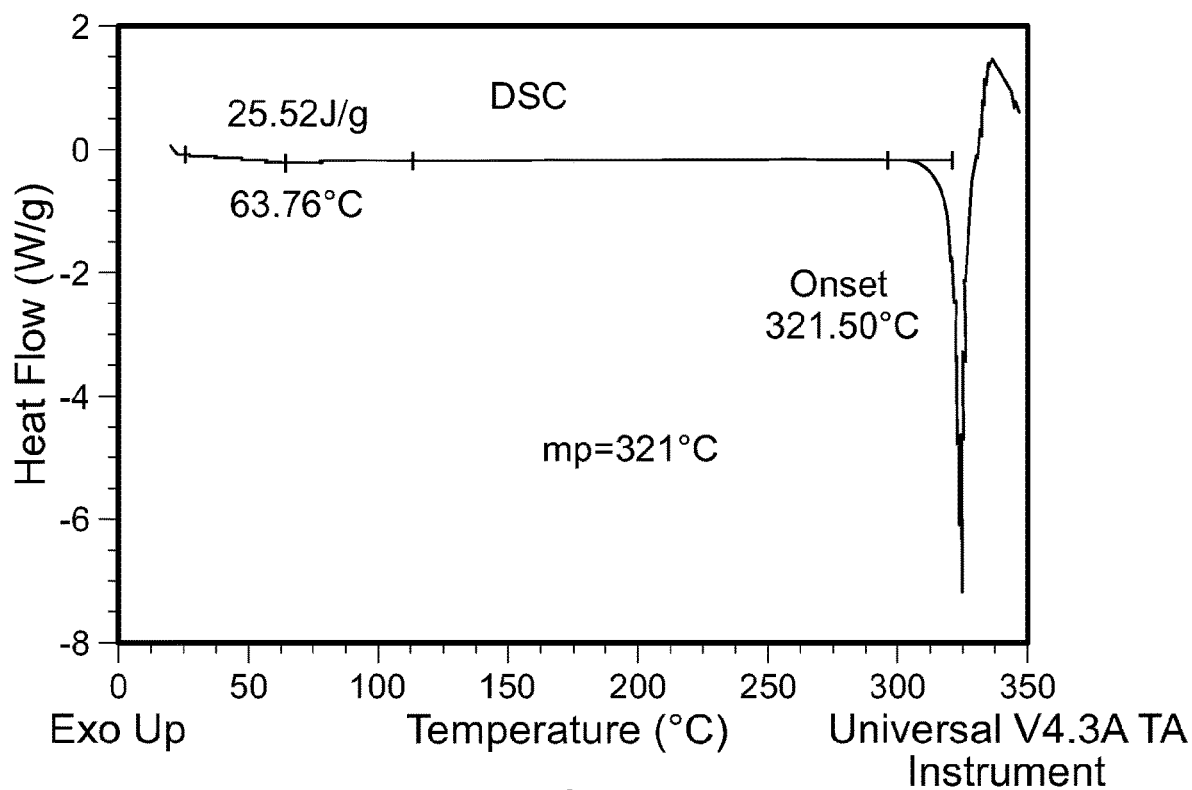
FIG. 6 is a DSC plot of N-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt.

FIG. 6 is a DSC plot of N-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt. The sample showed an endotherm at about 321° C.

Figure 7:
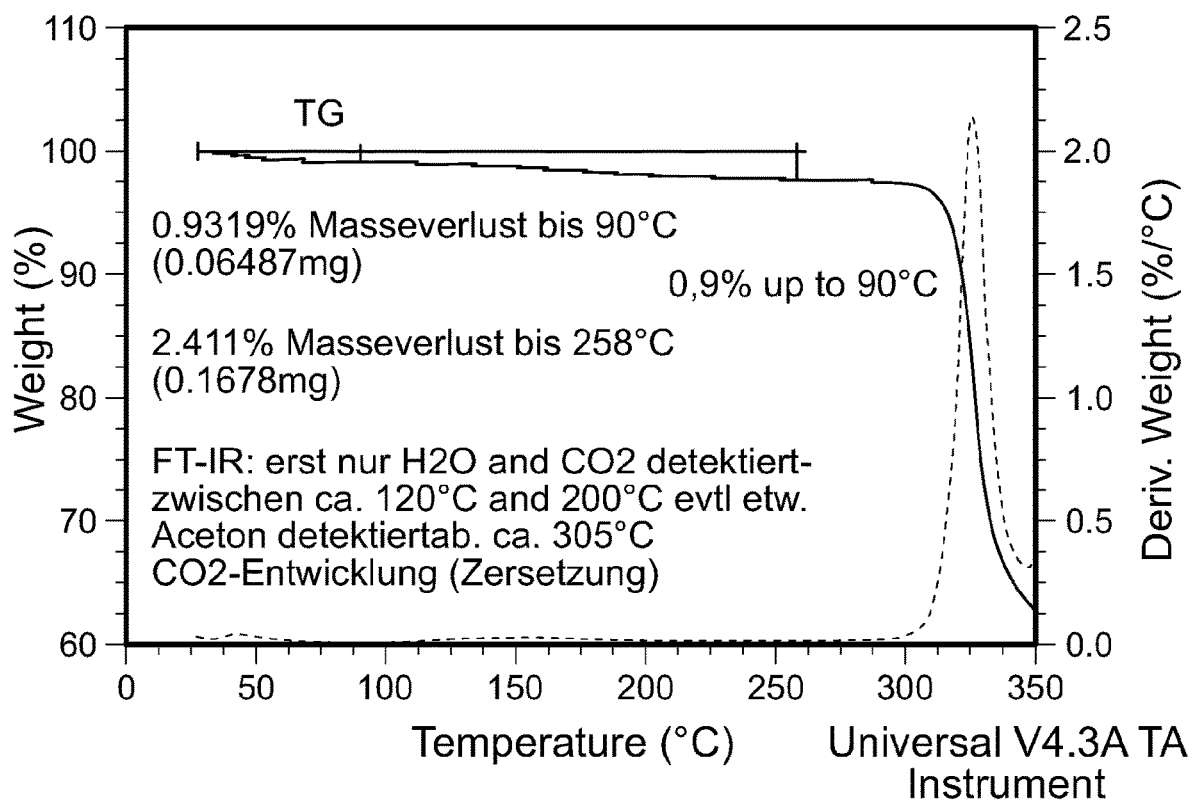
FIG. 7 is a TGA plot of N-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt.

FIG. 7 is a TGA plot of N-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt.

Figure 8:
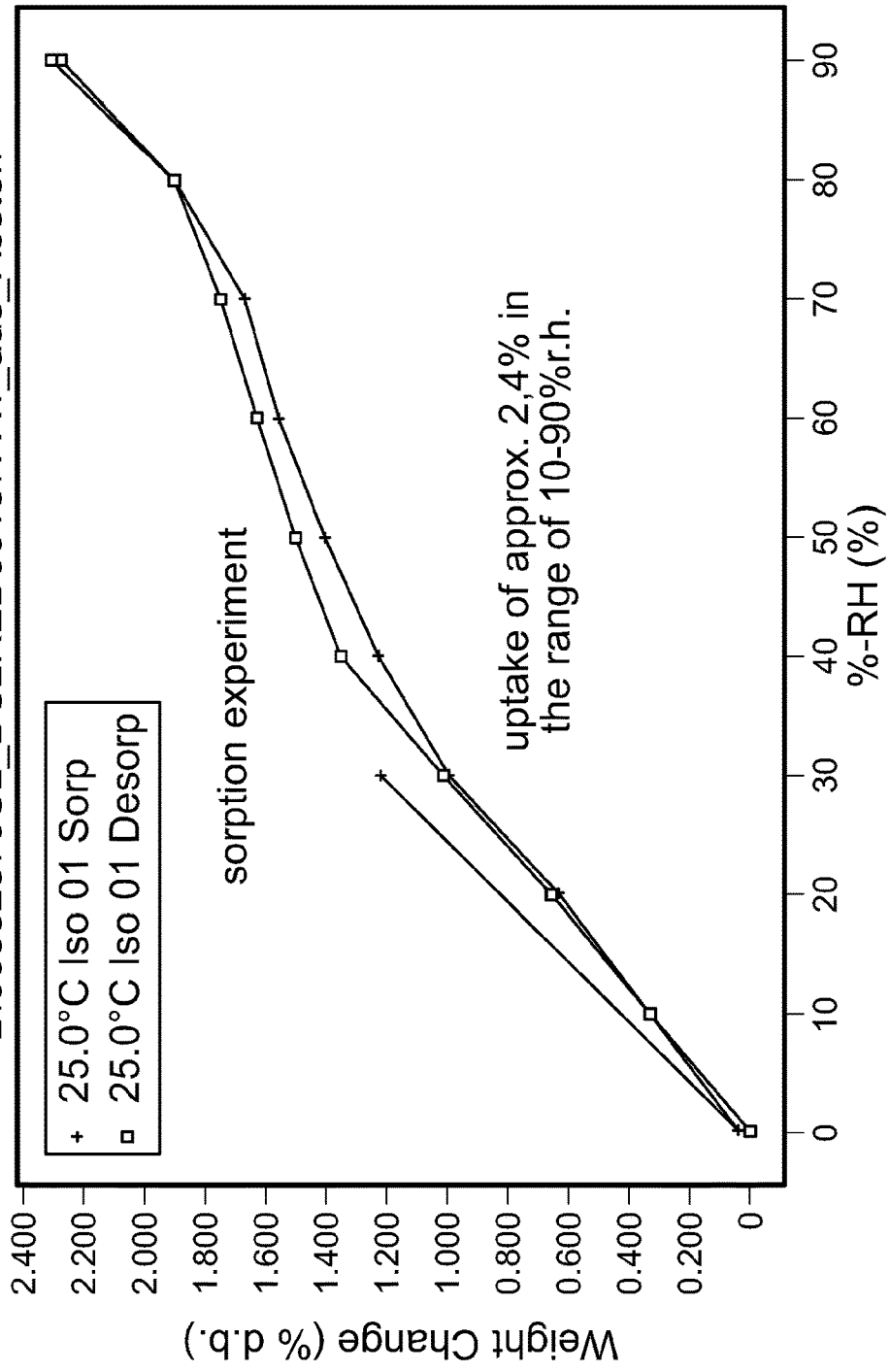
FIG. 8 is a sorption-desorption plot for N-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt showing weight gain and loss when the relative humidity was varied from 0-100%.

FIG. 8 is a sorption-desorption plot for N-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt showing weight gain and loss when the relative humidity was varied from 0-100%. The sample showed a weight gain of approximately 2.4% in the range from 10-90% relative humidity.

Figure 9:
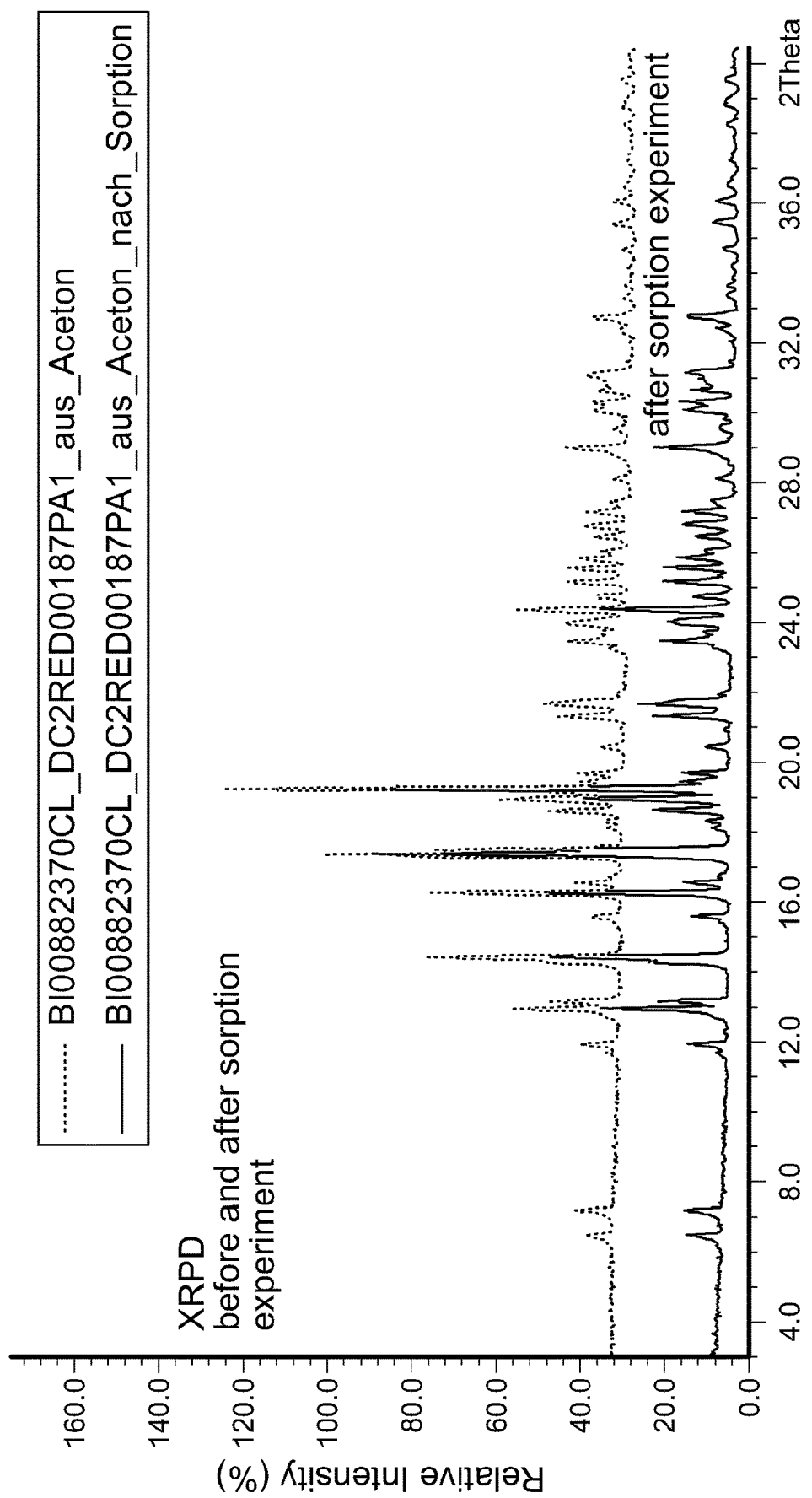
FIG. 9 is a plot of the XRPD of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt before (lower plot) and after (upper plot) a sorption-desorption experiment.

FIG. 9 is a plot of the XRPD of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt before (lower plot) and after (upper plot) the sorption-desorption experiment, showing that no significant change in structure occurred.

Data for N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt obtained by scale-up are shown in FIGS. 10-14.

FIG. 10 is a plot of the XRPD of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt with the sample from well F10 (lower plot) compared to the sample obtained from scale-up synthesis (upper plot).

FIG. 11 is a DSC plot of N-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt. The sample showed an endotherm at about 182° C.

FIG. 12 is a TGA plot of N-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt.

Figure 13:
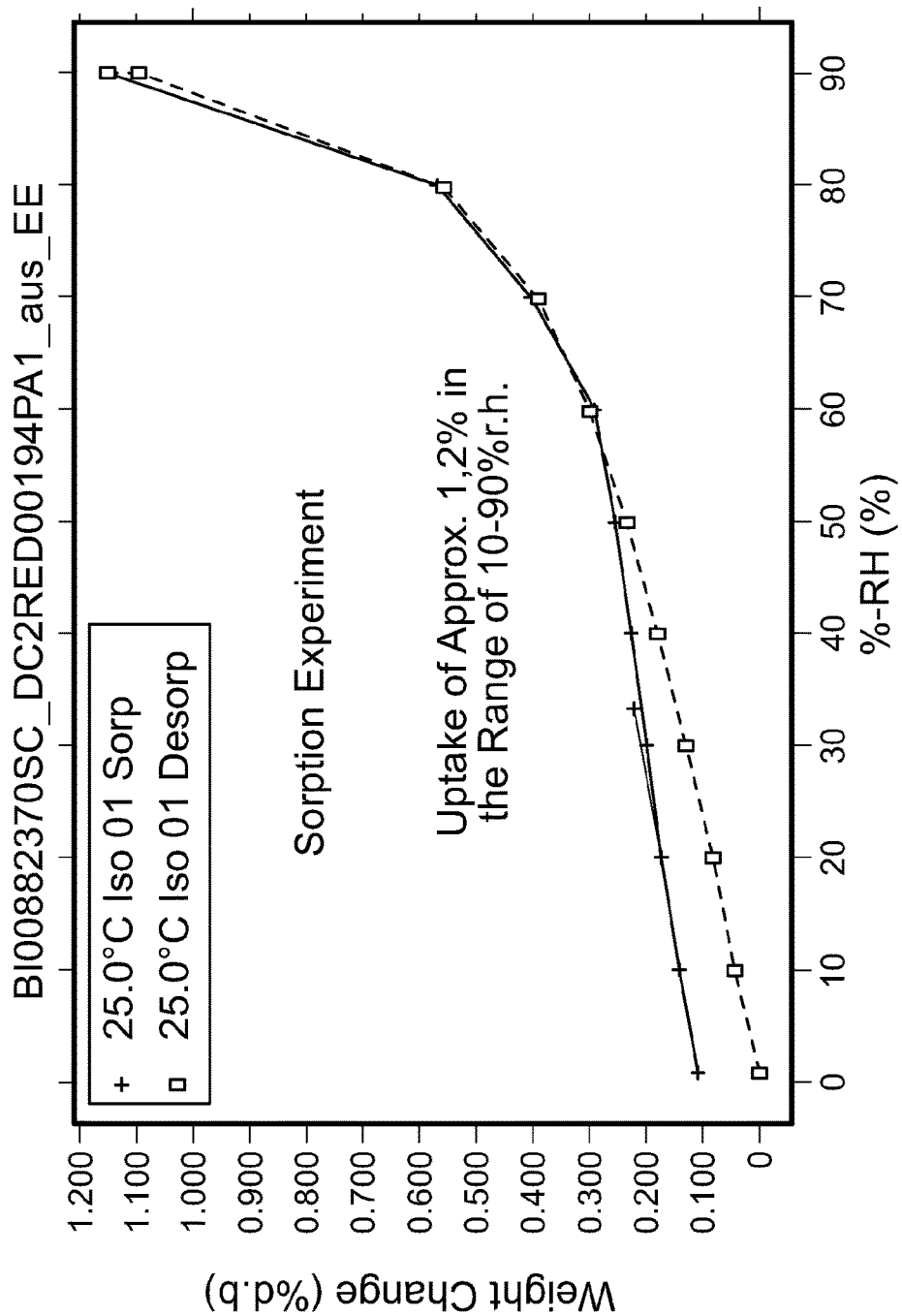
FIG. 13 is a sorption-desorption plot for N-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt showing weight gain and loss when the relative humidity was varied from 0-100%.

FIG. 13 is a sorption-desorption plot for N-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt showing weight gain and loss when the relative humidity was varied from 0-100%. The sample showed a weight gain of approximately 1.2% in the range from 10-90% relative humidity.

Figure 14:
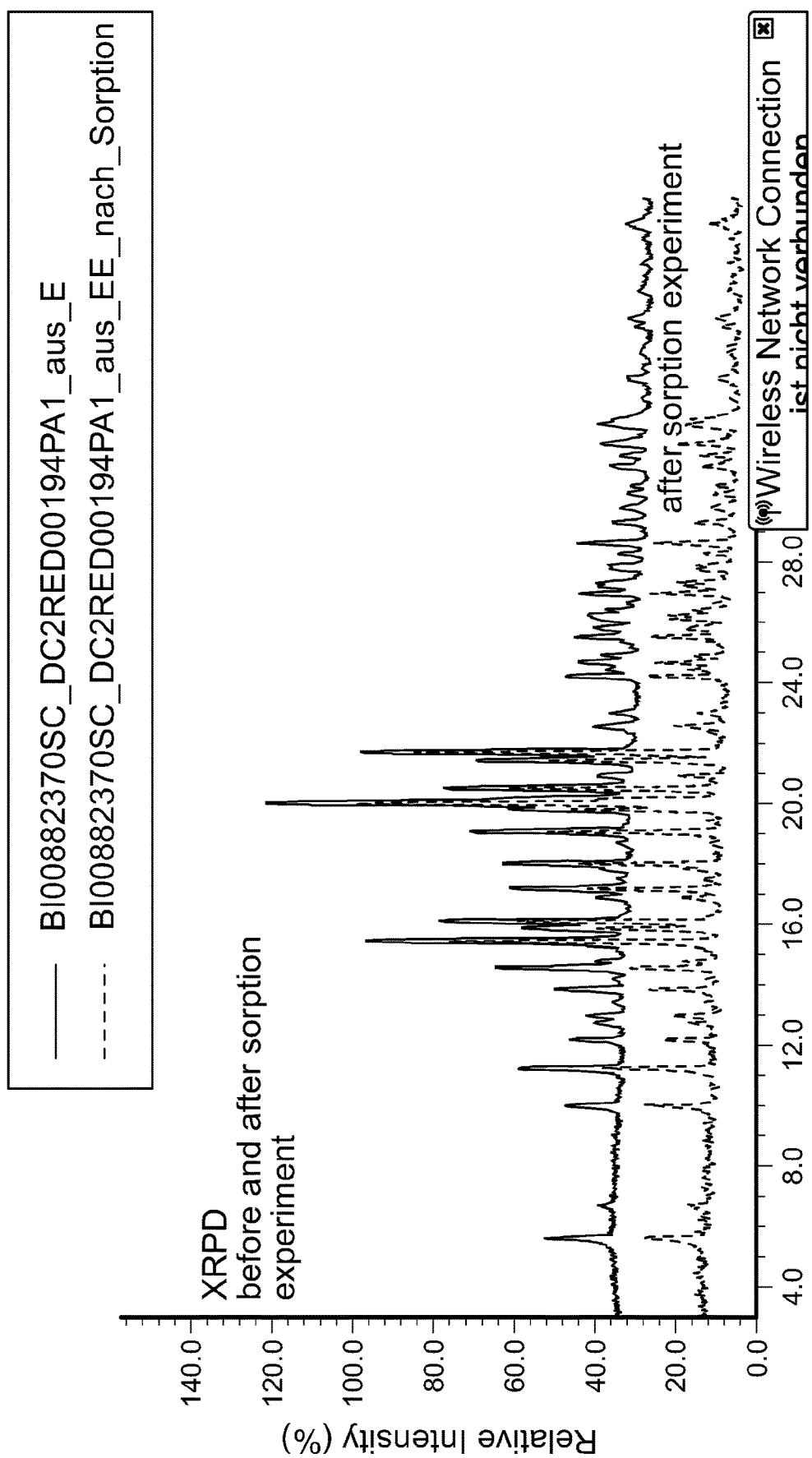
FIG. 14 is a plot of the XRPD of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt before (lower plot) and after (upper plot) a sorption-desorption experiment, showing that no significant change in structure occurred.

FIG. 14 is a plot of the XRPD of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt before (lower plot) and after (upper plot) the sorption-desorption experiment, showing that no significant change in structure occurred.

Synthesis and Properties of N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide Monohydrochloride Salt N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt was prepared in various solvent systems by dissolving N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide (100 mg, 176 μmol) in various solvents (10-20 mL), adding HCl (10 M solution in ethanol; 1 eq.) at 50° C. The resulting solution was then heated with stirring at a temperature of about the boiling point of the solvent for about 1 h then allowed to cool to room temperature and stirred for 3 h or more (e.g., overnight). The salt was then collected by filtration and dried at 50° C.

A summary of the experiments performed is provided in Table 5.

TABLE 5

Synthesis of N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide Monohydrochloride Salt

| Solvent | Yield of Salt | NMR Purity | Crystallinity | Form |
|---|---|---|---|---|
| EtOH (abs). | 79% | >95% | High | A |
| EtOH (90%) | 71% | >95% | High | A |
| iPrOH (abs). | 76% | >95% | High | A |
| iPrOH (90%) | 68% | >95% | High | A |
| Acetone | 65% | >95% | High | A |
| Ethyl Acetate | 73% | >95% | Medium | A |
| MIBK | 74% | >95% | Medium | A |
| THF | 76% | >95% | Low | |
| iPrOH (98%) | 98% | >95% | High | A# |
| EtOH | 95% | | High | A# |

Synthesized on a 1 g scale

Preparative Scale Synthesis of N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide Monohydrochloride Salt N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide (1.0 g, 1.76 mmol) in isopropanol (8 mL) was heated with stirring at 60° C., forming a brown solution. HCl (10 M solution in ethanol; 1.84 mmol, 1.05 eq.) was added. The resulting suspension was heated with stirring at 60° C. for 1 h, then at 80° C. for 1 h, then at 50° C. for 1 h, and was then allowed to cool to room temperature and stirred overnight (about 16 h). The salt was then collected by filtration and dried under reduced pressure at 50° C. overnight (about 16 h). This gave N-(3-(5-((1- ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt (1.023 g, 96% yield) as an off-white solid. Data for the N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt are shown in FIGS. 15-24.

Figure 15:
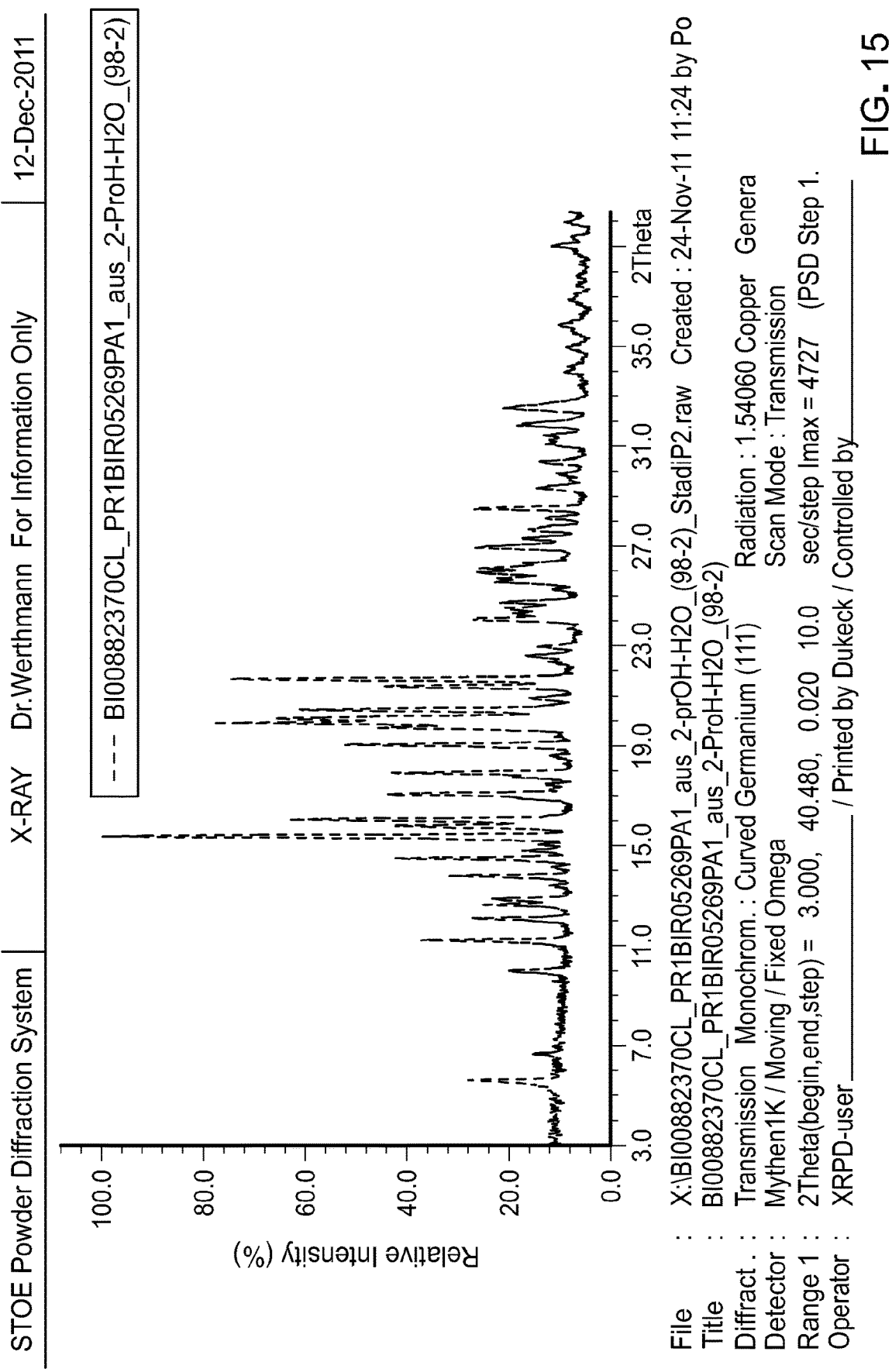
FIG. 15 is a plot of the XRPD of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt.

FIG. 15 is a plot of the XRPD of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt.

Table 6 is a list of representative XRPD peaks, d-values and relative intensities for the XRPD of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt.

TABLE 6

XRPD Peaks, d-Values and Relative Intensities for N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide Monohydrochloride Salt

| 2θ Value (°) | d-Value (Å) | Relative Intensity ($I/I_0$) (%) |
|---|---|---|
| 4.86 | 18.18 | 6 |
| 6.43 | 13.74 | 12 |
| 7.13 | 12.38 | 9 |
| 11.65 | 7.59 | 5 |
| 11.90 | 7.43 | 13 |
| 12.91 | 6.85 | 33 |
| 13.15 | 6.73 | 19 |
| 14.24 | 6.21 | 22 |
| 14.38 | 6.15 | 57 |
| 15.37 | 5.76 | 6 |
| 15.56 | 5.69 | 9 |
| 16.22 | 5.46 | 50 |
| 16.50 | 5.37 | 14 |
| 16.70 | 5.30 | 6 |
| 17.37 | 5.11 | 100 |
| 18.09 | 4.90 | 8 |
| 18.25 | 4.86 | 8 |
| 18.57 | 4.77 | 26 |
| 18.90 | 4.69 | 38 |
| 19.19 | 4.62 | 99 |
| 19.41 | 4.57 | 12 |
| 19.64 | 4.51 | 16 |
| 20.41 | 4.35 | 7 |
| 20.91 | 4.25 | 5 |
| 21.26 | 4.18 | 19 |
| 21.59 | 4.11 | 18 |
| 21.72 | 4.09 | 19 |
| 23.23 | 3.83 | 9 |
| 23.40 | 3.80 | 18 |
| 23.56 | 3.77 | 11 |
| 23.66 | 3.76 | 10 |
| 23.96 | 3.71 | 19 |
| 24.32 | 3.66 | 30 |
| 24.73 | 3.60 | 10 |
| 25.11 | 3.54 | 14 |
| 25.30 | 3.52 | 6 |
| 25.52 | 3.49 | 18 |
| 25.80 | 3.45 | 17 |
| 26.01 | 3.42 | 11 |
| 26.41 | 3.37 | 9 |
| 26.74 | 3.33 | 18 |
| 27.16 | 3.28 | 14 |
| 27.44 | 3.25 | 8 |
| 28.09 | 3.17 | 5 |
| 28.93 | 3.08 | 15 |
| 29.49 | 3.03 | 7 |
| 30.01 | 2.98 | 16 |
| 30.25 | 2.95 | 12 |
| 30.57 | 2.92 | 10 |
| 30.73 | 2.91 | 10 |
| 31.05 | 2.88 | 17 |
| 31.60 | 2.83 | 4 |

TABLE 6-continued

XRPD Peaks, d-Values and Relative Intensities for N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide Monohydrochloride Salt

| 2θ Value (°) | d-Value (Å) | Relative Intensity ($I/I_0$) (%) |
|---|---|---|
| 32.33 | 2.77 | 6 |
| 32.69 | 2.74 | 16 |
| 33.31 | 2.69 | 5 |
| 34.10 | 2.63 | 4 |
| 34.61 | 2.59 | 6 |
| 35.38 | 2.53 | 7 |
| 36.01 | 2.49 | 6 |
| 36.43 | 2.46 | 5 |
| 37.23 | 2.41 | 4 |
| 38.78 | 2.32 | 6 |
| 39.47 | 2.28 | 5 |
| 39.89 | 2.26 | 4 |

Figure 16:
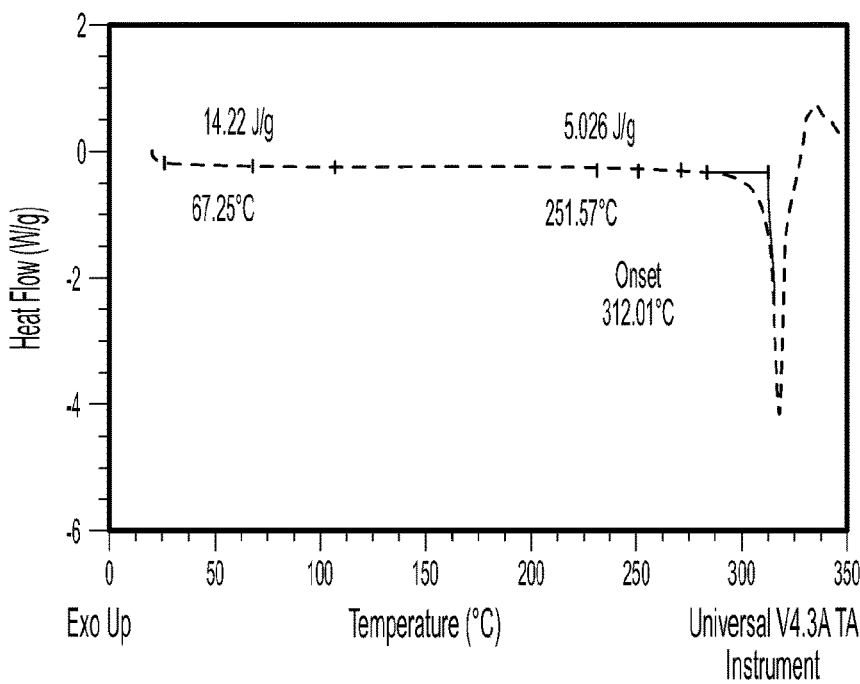
FIG. 16 is a DSC plot of N-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt. The sample showed an endotherm with an onset at about 313° C. In general, samples had an endotherm with an onset in the range of 312-322° C., corresponding to the melting point. The melting point is therefore measured at about 317±5° C. Some samples had an additional endothermic event at about 250° C., corresponding to loss of solvent.

FIG. 16 is a DSC plot of N-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt. The sample showed an endotherm with an onset at about 313° C. In general, samples had an endotherm with an onset in the range of 312-322° C., corresponding to the melting point. The melting point is therefore measured at about 317±5° C. Some samples had an additional endothermic event at about 250° C., corresponding to loss of solvent.

Figure 17:
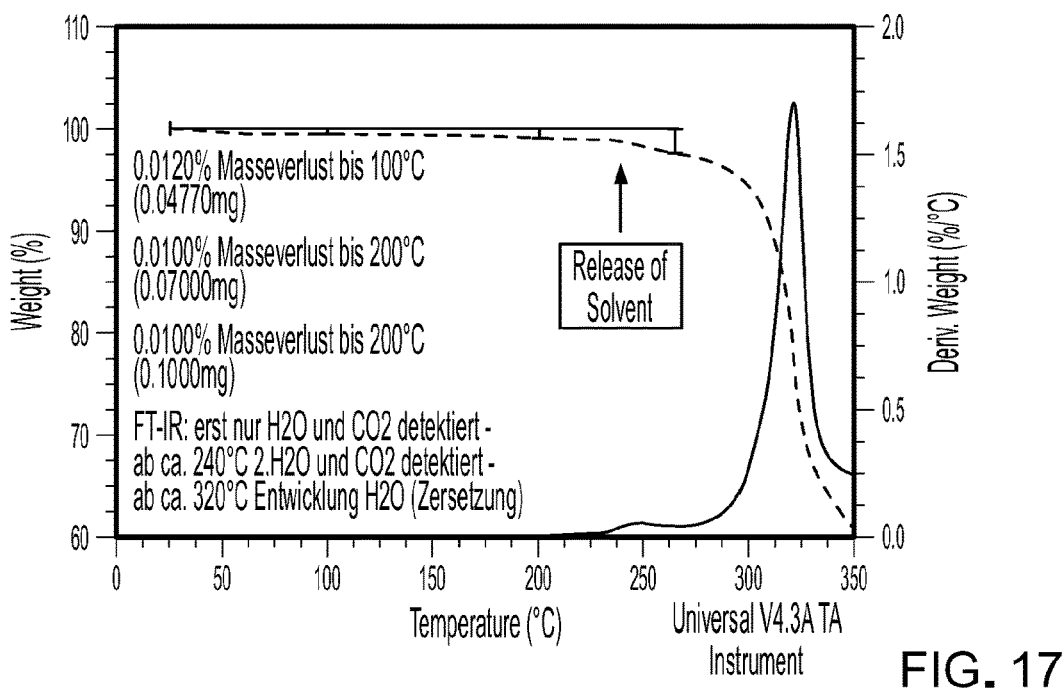
FIG. 17 is a TGA plot of N-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt. The sample exhibited a loss on drying of about 1.7-2.5% up to about 250° C. corresponding to release of water and solvent. The water content was measured at about 0.9% (Karl Fischer method).

FIG. 17 is a TGA plot of N-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt. The sample exhibited a loss on drying of about 1.7-2.5% up to about 250° C. corresponding to release of water and solvent. The water content was measured at about 0.9% (Karl Fischer method).

Figure 18:
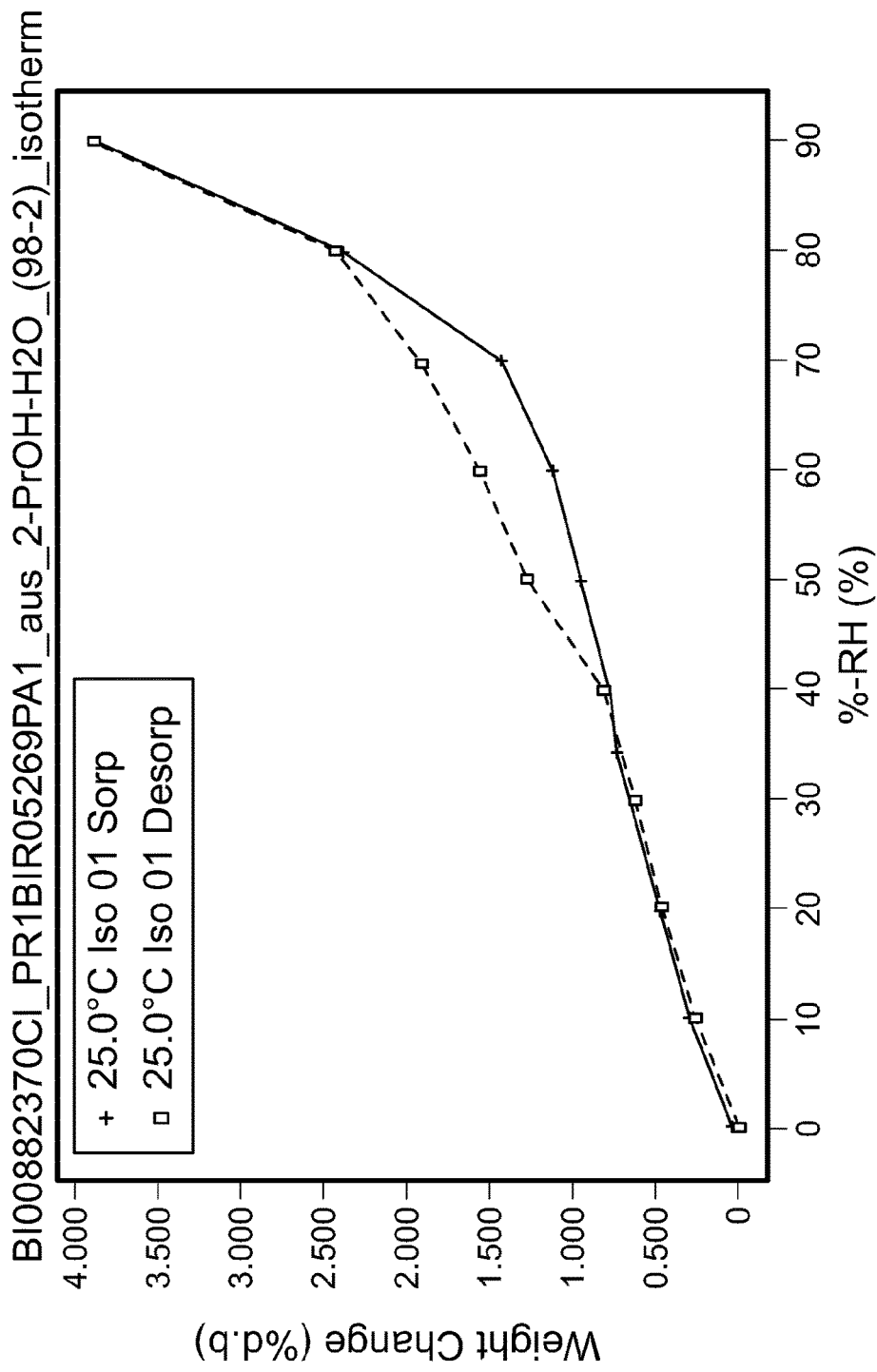
FIG. 18 is an isotherm sorption-desorption plot for N-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt showing weight gain and loss when the relative humidity was varied from 0-90%.

FIG. 18 is an isotherm sorption-desorption plot for N-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt showing weight gain and loss when the relative humidity was varied from 0-90%. The sample showed a reversible weight gain of approximately 4% in the range from 0-90% relative humidity and a reversible weigh gain of approximately 2.5% in the range from 0-80% relative humidity. The amount absorbed and desorbed appears to depend on the amount of organic solvent present in the sample.

Figure 19:
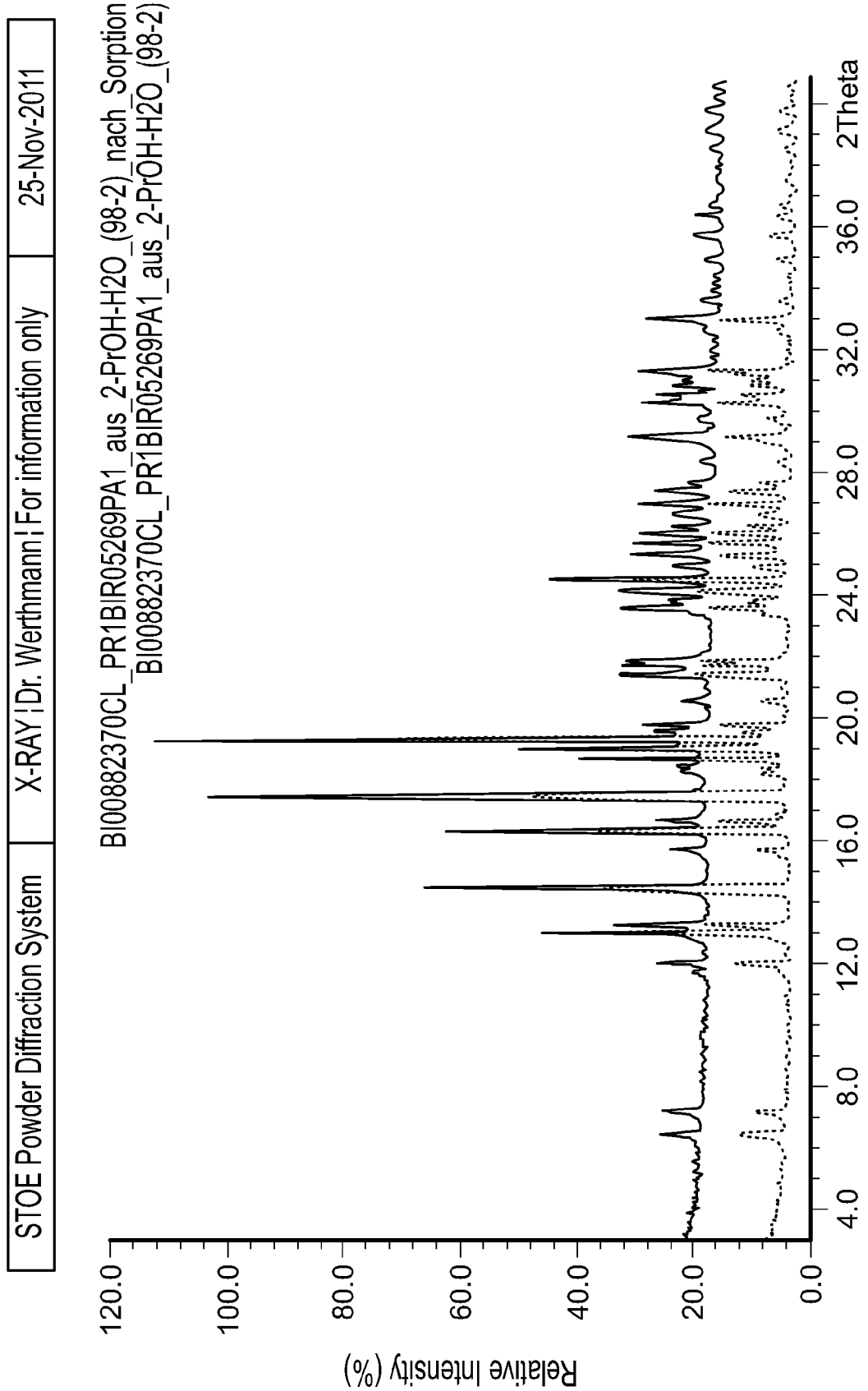
FIG. 19 is a plot of the XRPD of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt before (lower plot) and after (upper plot) a sorption-desorption experiment, showing that no significant change in structure occurred.

FIG. 19 is a plot of the XRPD of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt before (lower plot) and after (upper plot) the sorption-desorption experiment, showing that no significant change in structure occurred.

Figure 20:
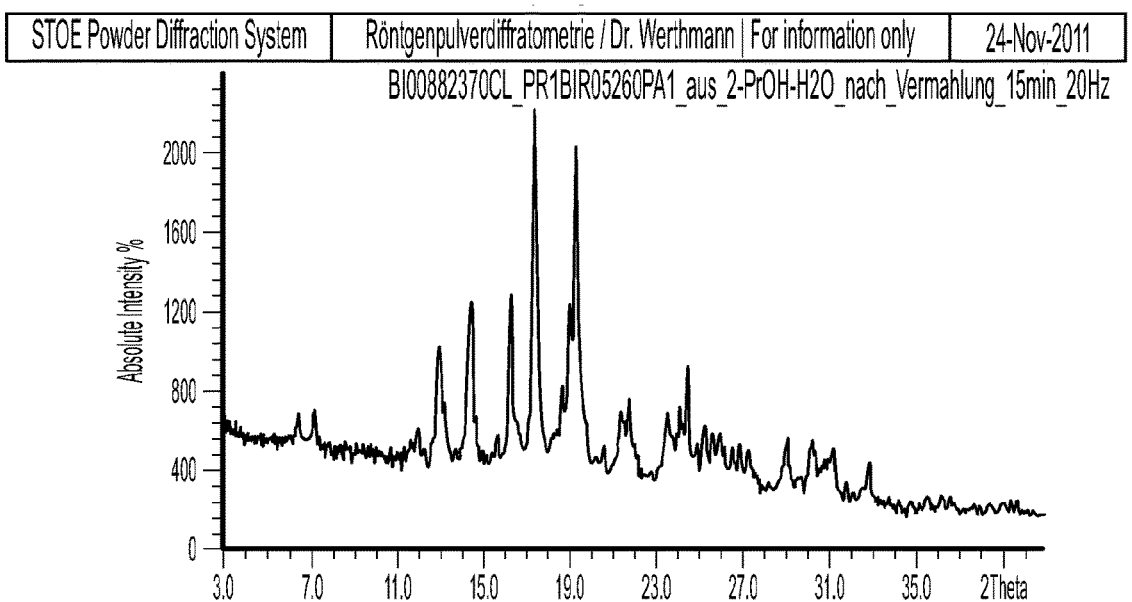
FIG. 20 is a plot of the XRPD of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt following milling in a swing mill for 10 min. at 30 rps.

FIG. 20 is a plot of the XRPD of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt following milling in a swing mill for 10 min. at 30 rps. The sample showed a significant decrease in crystallinity but no change in polymorphic form.

Figure 21:
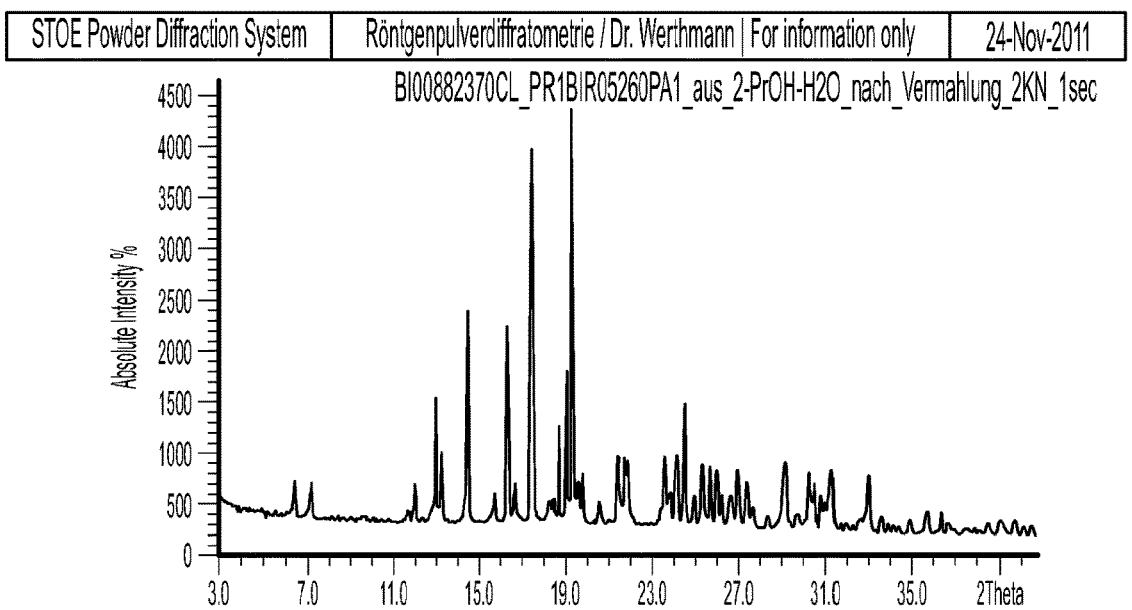
FIG. 21 is a plot of the XRPD of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt following compression at 2000 N for 1 s to a tablet (diameter-5 mm).

FIG. 21 is a plot of the XRPD of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt following compression at 2000 N for 1 s to a tablet (diameter-5 mm). The sample showed a slight decrease in crystallinity but no change in polymorphic form.

Figure 22:
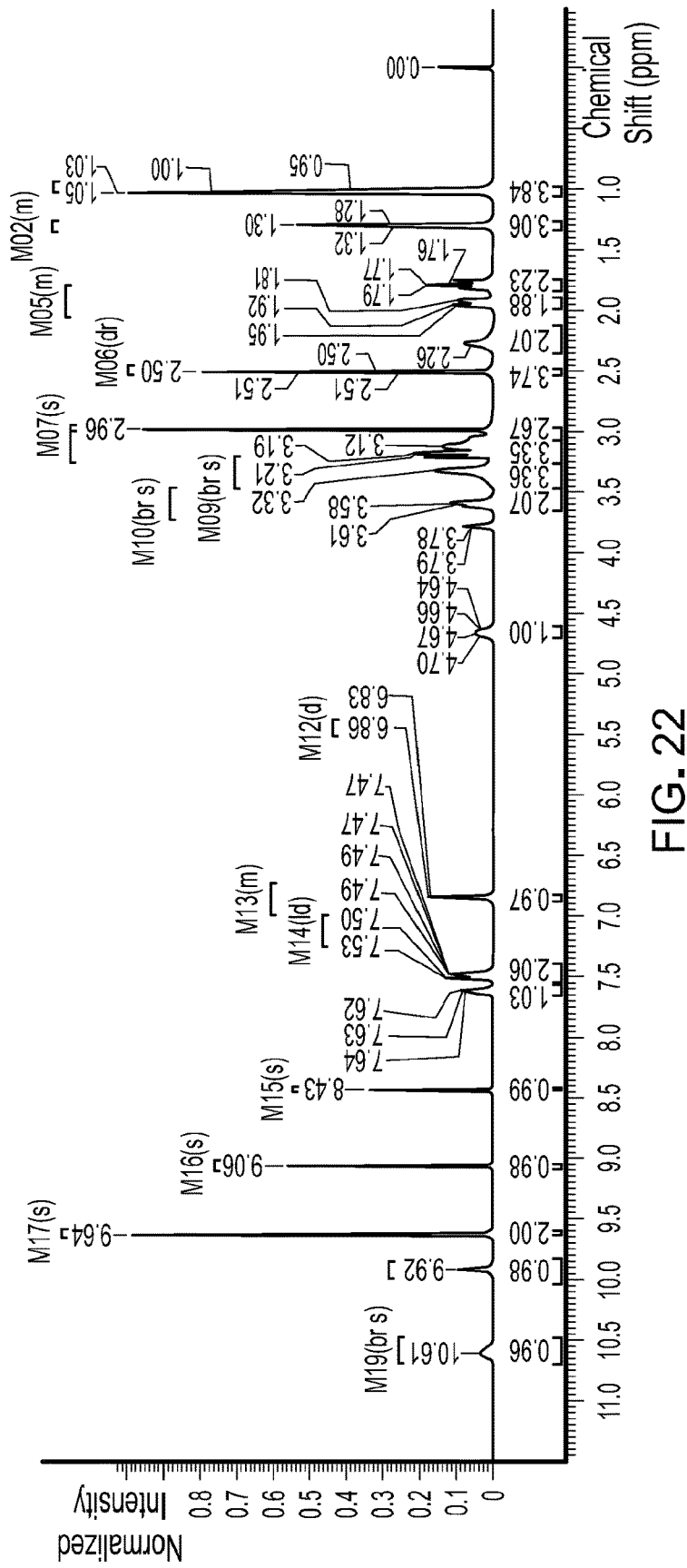
FIG. 22 is a ¹H N.M.R. spectrum (400 MHz, DMSO-d6) of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt.

FIG. 22 is a ¹H N.M.R. spectrum (400 MHz, DMSO-d6) of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt.

Figure 23:
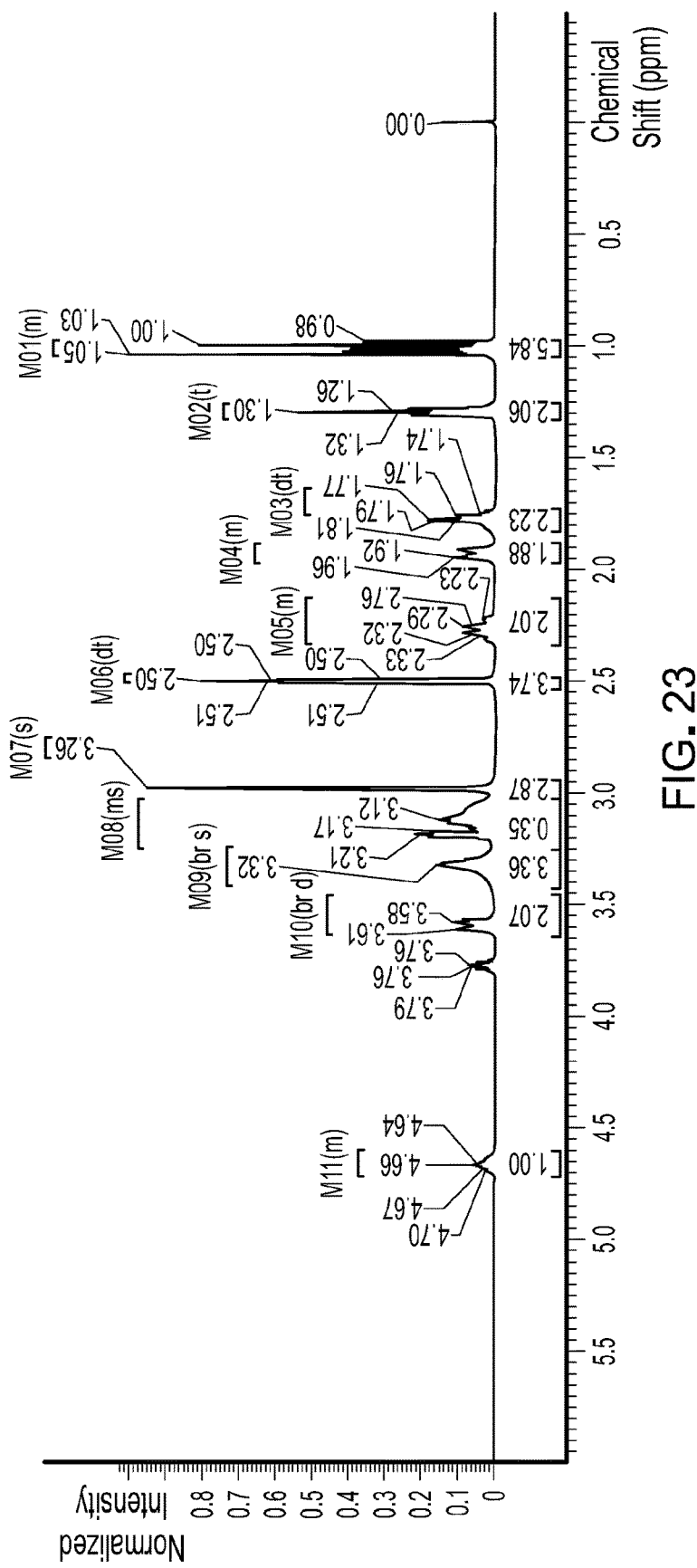
FIG. 23 is an inset on the aliphatic region (δ-0.5-6.0) of the ¹H N.M.R. spectrum (400 MHz, DMSO-d6) of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt.

FIG. 23 is an inset on the aliphatic region (δ-0.5-6.0) of the ¹H N.M.R. spectrum (400 MHz, DMSO-d6) of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt.

Figure 24:
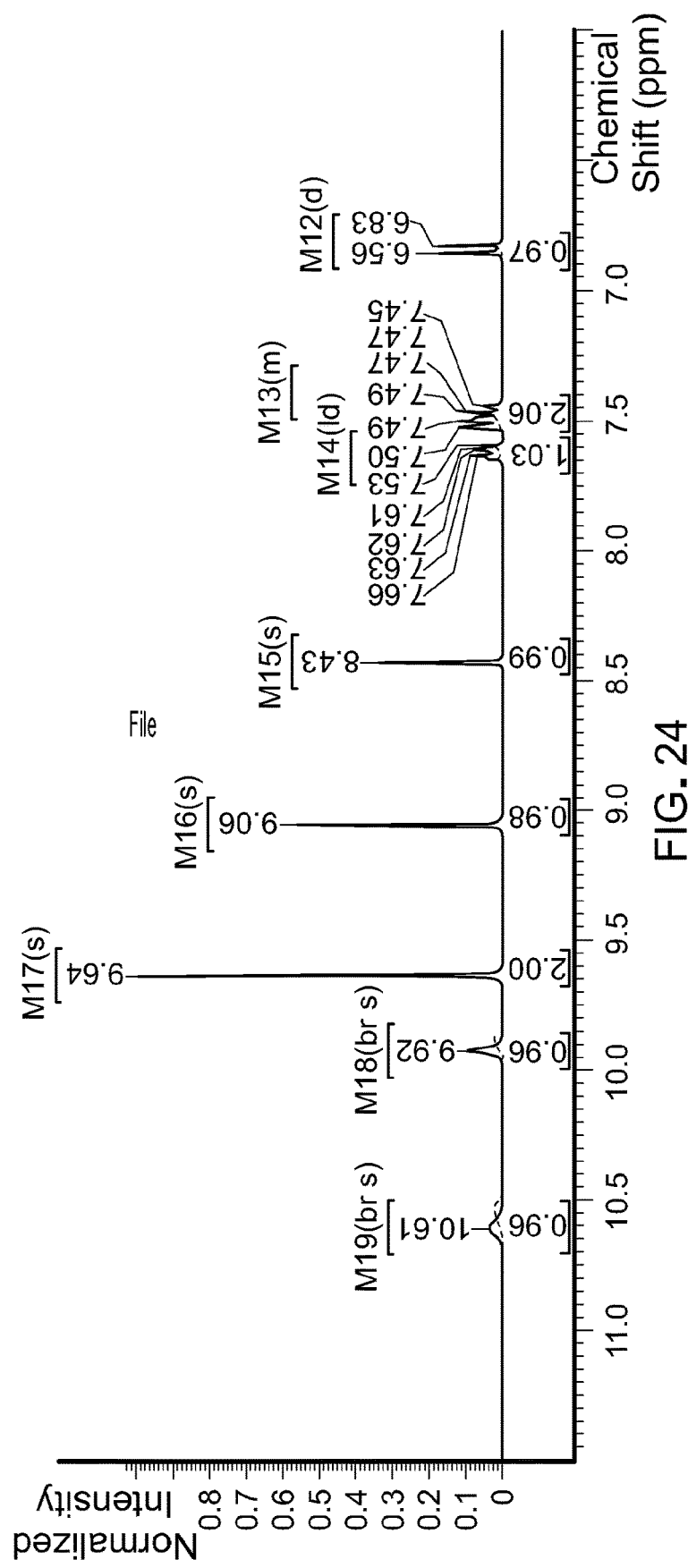
FIG. 24 is an inset on the aromatic region (δ 6.0-11.5) of the ¹H N.M.R. spectrum (400 MHz, DMSO-d6) of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt.

FIG. 24 is an inset on the aromatic region (δ 6.0-11.5) of the ¹H N.M.R. spectrum (400 MHz, DMSO-d6) of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt.

The equilibrium solubility of N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt in various media was determined. The results are summarized in Table 7.

TABLE 7

Solubility of N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide Monohydrochloride Salt In Various Media

| Medium | Solubility after 2 h (mg/mL) |
| --- | --- |
| Water | 0.1 |
| HCl (0.1M) | 0.06 |
| HCl (0.01M) | 0.02 |
| McIlvaine Buffer (pH 2.2) | 0.40 |
| McIlvaine Buffer (pH 3.0) | 0.20 |
| McIlvaine Buffer (pH 4.0) | 0.10 |
| McIlvaine Buffer (pH 4.5) | 0.20 |
| McIlvaine Buffer (pH 5.0) | 0.20 |
| Acetate Buffer (pH 5.0) | 0.20 |
| McIlvaine Buffer (pH 6.0) | 0.10 |
| McIlvaine Buffer (pH 6.8) | 0.10 |
| Phosphate Buffer (pH 6.8) | 0.20 |
| McIlvaine Buffer (pH 7.4) | 0.01 |
| Sorensen Buffer (pH 9.0) | 0.01 |
| Sorensen Buffer (pH 11) | 0.70 |
| 0.1M NaOH | >10.00 |
| 0.1M Citric acid | 0.40 |
| Simulated intestinal fluid (FaSSIF) | 0.002 |
| Simulated intestinal fluid (FeSSIF) | 0.03 |

The intrinsic dissolution rate of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt in various media was measured in media at various pH values. The results are summarized in Table 8.

TABLE 8

Intrinsic Dissolution Rate of N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide Monohydrochloride Salt in Aqueous Media at pH 1.0-7.4

| pH of Medium | Intrinsic Dissolution Rate (μg/cm²/min.) |
| --- | --- |
| 1.0 | 4 |
| 2.2 | 121 |
| 3.0 | 80 |
| 4.5 | 38 |
| 6.8 | 15 |
| 7.4 | 3 |

Figure 25:
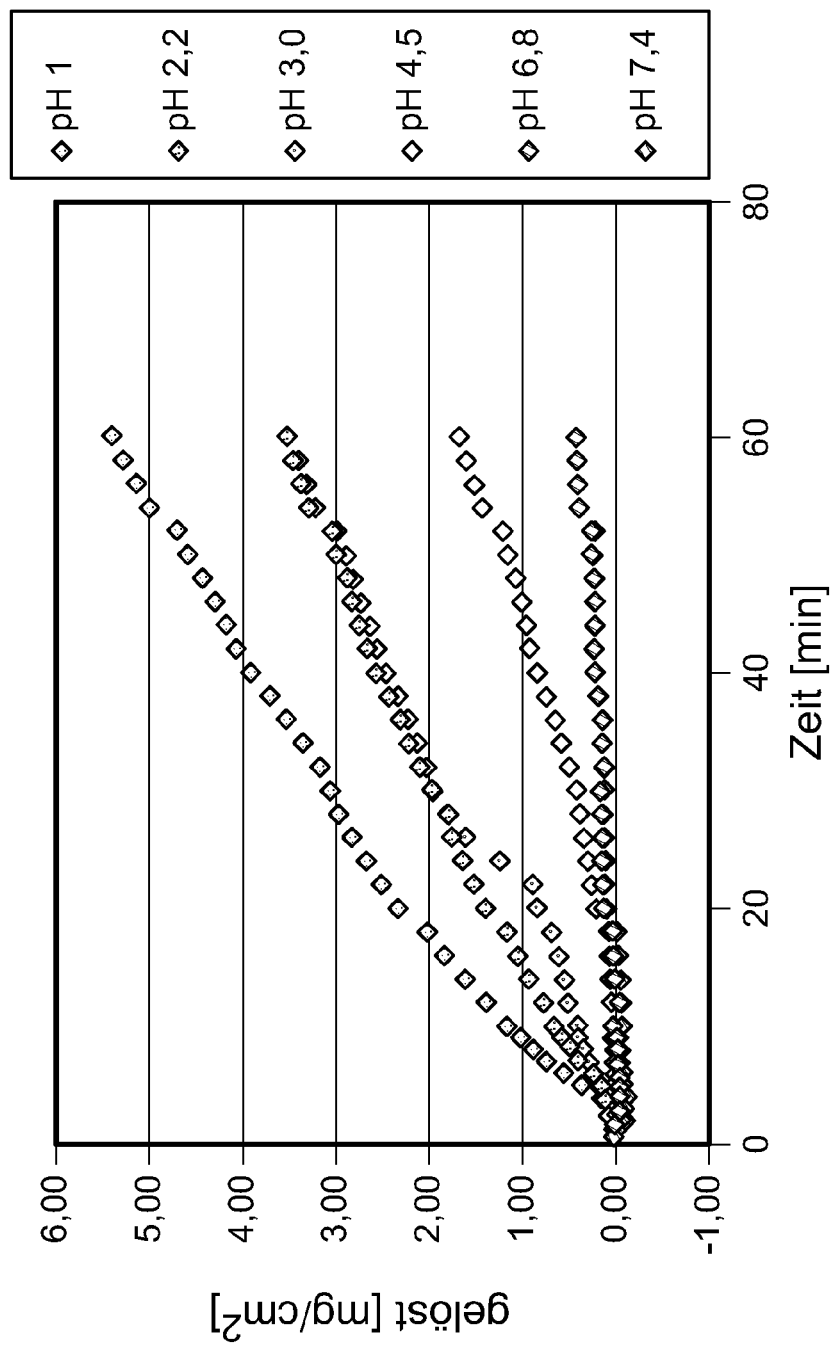
FIG. 25 is a plot showing the rate of dissolution of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt over 0-60 min. in aqueous medium at pH values of 1.0 to 7.4.

FIG. 25 is a plot showing the rate of dissolution of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt over 0-60 min. in aqueous medium at pH values of 1.0 to 7.4.

Synthesis and Properties of N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide Monosuccinate Salt N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt was prepared in various solvent systems by dissolving N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide (100 mg, 176 μmol) in various solvents (about 8-10 mL per mg of the drug) with heating, and adding succinic acid (1 eq.). The resulting solution was heated with stirring at about 60-80° C. for about 1 h then allowed to cool to room temperature and stirred for 3 h or more (e.g., overnight). The salt was then collected by filtration and dried at 50° C.

A summary of the experiments performed is provided in Table 8.

TABLE 8

Synthesis of N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide Monosuccinate Salt

| Solvent | Yield of Salt | NMR Purity | Crystallinity | Form |
| --- | --- | --- | --- | --- |
| EtOH (abs). | 77% | >95% | High | A |
| iPrOH | 85% | >95% | High | A |
| Acetone | 85% | >95% | High | F* |
| Ethyl Acetate | 84% | >95% | High | A |
| MIBK | 0% (No crystallization) | | | |
| EtOH (abs). | 89% | >95% | High | A |
| EtOH (96%) | 70% | ca. 95% | High | A |
| EtOH (96%) | 75% | >95% | High | A |
| EtOH (96%) | 75% | >95% | High | A |
| EtOH (98%). | 92% | >95% | High | A |
| EtOH (abs) | 94% | >95% | High | A |
| EtOH (98%) | 95% | | High | A |
| EtOH (97%) | 92% | >95% | High | A |

*Acetone solvate.

For N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt, crystallization from a number of solvents gave the same crystalline form (form A) as was obtained from the experiments described above, but a different crystalline form (form B) (an acetone solvate) was obtained by crystallization from acetone.

Preparative Scale Synthesis of N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide Monosuccinate Salt (Form A)

N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide (800 mg, 1.40 mol) in ethanol (8 mL) was heated with stirring at 60° C., forming a pale yellow solution. Succinic acid (166 mg, 1.40 mmol, 1.0 eq.) was added. The resulting solution was heated with stirring at 60° C. for 10 min., then at 45° C. for 10 min., until the formation of a precipitate was stirred. The suspension was then heated with stirring at 55° C. for 1 h, and was then allowed to cool to room temperature and stirred overnight (about 16 h). The salt was then collected by filtration and dried under reduced pressure at 50° C. for 3 days. This gave N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt (726 mg, 75% yield) as an off-white solid. Data for the N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt (Form A) obtained are shown in FIGS. 26-35.

FIG. 26 is a plot of the XRPD of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt (Form A).

Table 9 is a list of representative XRPD peaks, d-values and relative intensities for the XRPD of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt (Form A).

TABLE 9

XRPD Peaks, d-Values and Relative Intensities for N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide Monosuccinate Salt (Form A)

| 2θ Value (°) | d-Value (Å) | Relative Intensity ($I/I_0$) (%) |
|---|---|---|
| 5.63 | 15.68 | 20 |
| 6.72 | 13.15 | 5 |
| 7.26 | 12.16 | 1 |
| 10.05 | 8.80 | 13 |
| 11.28 | 7.84 | 32 |
| 12.15 | 7.28 | 20 |
| 12.72 | 6.95 | 17 |
| 12.94 | 6.84 | 17 |
| 13.45 | 6.58 | 3 |
| 13.85 | 6.39 | 25 |
| 14.20 | 6.23 | 3 |
| 14.56 | 6.08 | 38 |
| 14.87 | 5.95 | 9 |
| 15.13 | 5.85 | 6 |
| 15.44 | 5.73 | 100 |
| 15.86 | 5.58 | 38 |
| 16.13 | 5.49 | 63 |
| 16.97 | 5.22 | 12 |
| 17.15 | 5.17 | 40 |
| 17.33 | 5.11 | 4 |
| 17.54 | 5.05 | 6 |
| 17.85 | 4.97 | 13 |
| 18.00 | 4.92 | 37 |
| 18.67 | 4.75 | 4 |
| 19.14 | 4.63 | 47 |
| 19.48 | 4.55 | 2 |
| 19.82 | 4.48 | 43 |
| 20.01 | 4.43 | 79 |
| 20.20 | 4.39 | 62 |
| 20.54 | 4.32 | 60 |
| 21.01 | 4.23 | 10 |
| 21.48 | 4.13 | 44 |
| 21.78 | 4.08 | 74 |
| 22.68 | 3.92 | 10 |
| 23.07 | 3.85 | 6 |
| 24.17 | 3.68 | 23 |
| 24.38 | 3.65 | 13 |
| 24.60 | 3.62 | 16 |
| 24.86 | 3.58 | 15 |
| 25.37 | 3.51 | 5 |
| 25.67 | 3.47 | 17 |
| 25.79 | 3.45 | 17 |
| 26.05 | 3.42 | 21 |
| 26.23 | 3.39 | 20 |
| 26.39 | 3.37 | 12 |
| 26.61 | 3.35 | 3 |
| 27.06 | 3.29 | 21 |
| 27.42 | 3.25 | 11 |
| 27.77 | 3.21 | 11 |
| 27.90 | 3.19 | 8 |
| 28.25 | 3.16 | 7 |
| 28.64 | 3.11 | 24 |
| 29.45 | 3.03 | 9 |
| 29.79 | 3.00 | 3 |
| 30.02 | 2.97 | 5 |

FIG. 27 is a DSC plot of N-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt. The sample showed an endotherm with an onset at about 180° C. In general, samples had an endotherm with an onset in the range of 179-182° C., corresponding to the melting point. The melting point is therefore measured at about 180±3° C. Some samples had an additional endothermic event at about 160-165° C., corresponding to loss of solvent.

FIG. 28 is a TGA plot of N-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt. The sample exhibited a loss on drying of about 1.4-3.7% up to about 250° C. corresponding to release of water and solvent. The water content was measured at about 0.03% (Karl Fischer method). The salt tends to include variable amounts of solvent in the crystals, which is released at temperatures greater than about 160° C.

Figure 29:
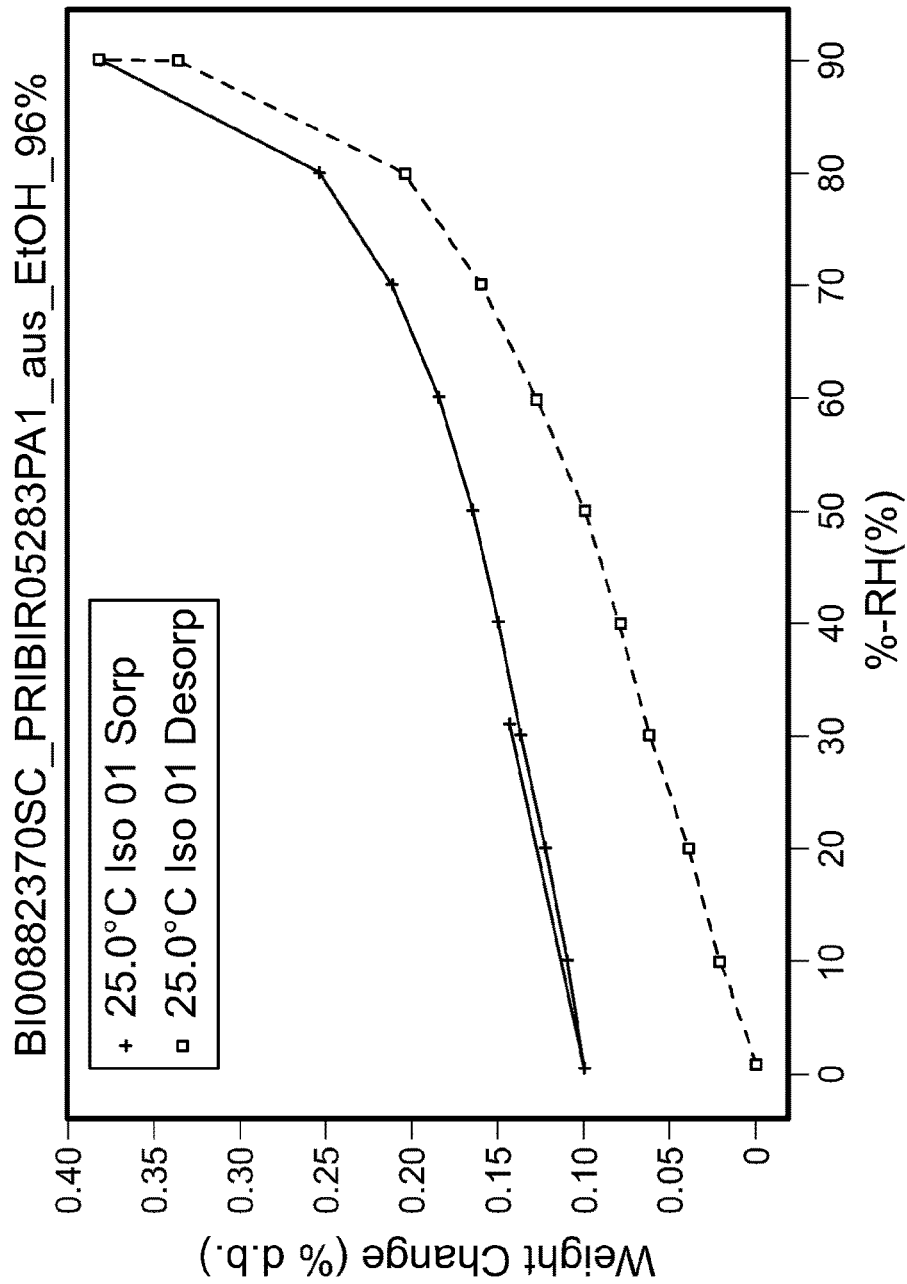
FIG. 29 is an isotherm sorption-desorption plot for N-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt showing weight gain and loss when the relative humidity was varied from 0-90%.

FIG. 29 is an isotherm sorption-desorption plot for N-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt showing weight gain and loss when the relative humidity was varied from 0-90%. The sample showed a reversible weight gain of approximately 0.4% in the range from 0-90% relative humidity and a reversible weigh gain of approximately 0.25% in the range from 0-80% relative humidity. The amount absorbed and desorbed appears to depend on the amount of organic solvent present in the sample. The sorption and desorption were fully reversible with no change in crystallinity or polymorphic form.

Figure 30:
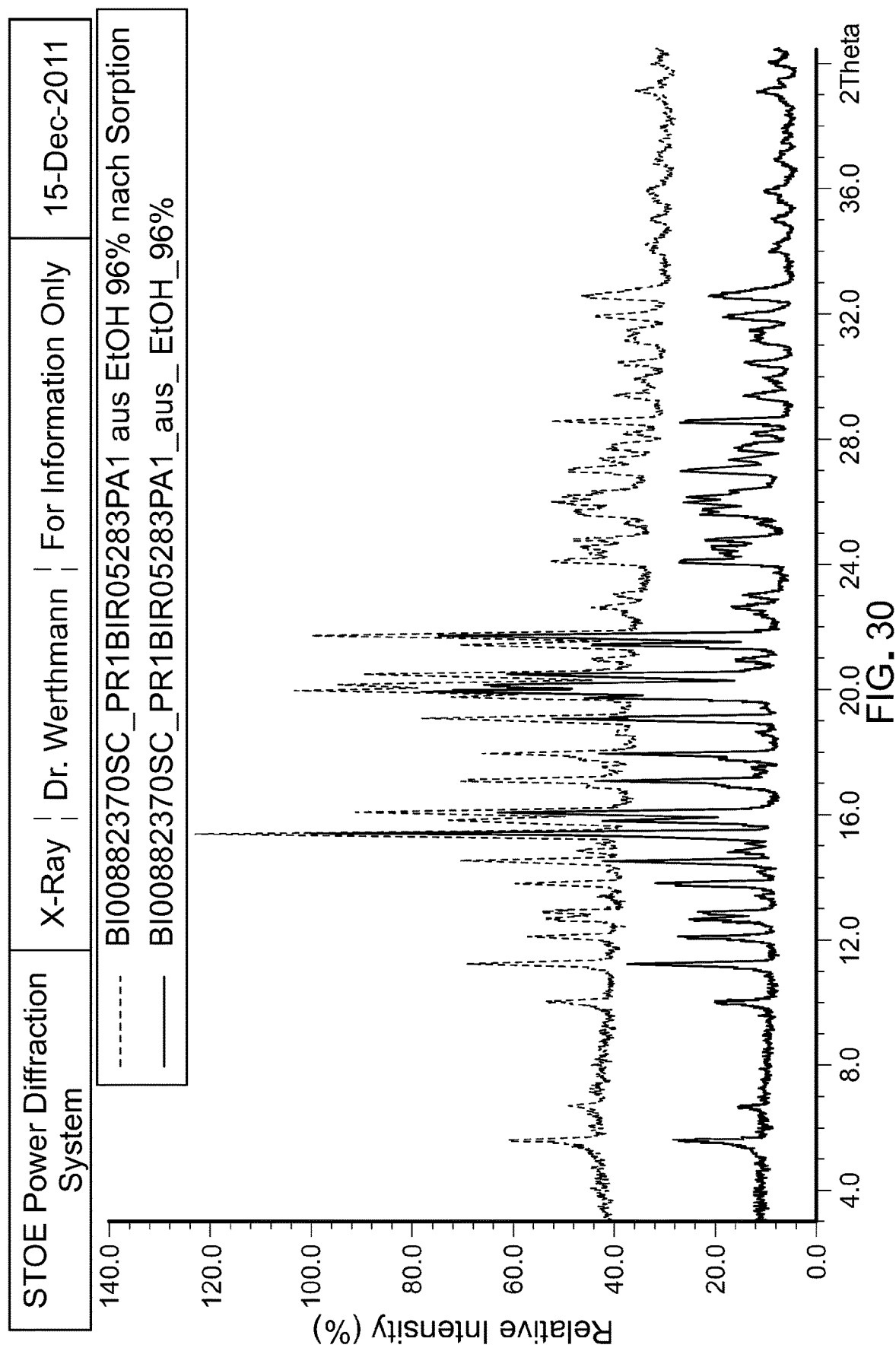
FIG. 30 is a plot of the XRPD of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt before (lower plot) and after (upper plot) a sorption-desorption experiment, showing that no significant change in structure occurred.

FIG. 30 is a plot of the XRPD of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt before (lower plot) and after (upper plot) the sorption-desorption experiment, showing that no significant change in structure occurred.

Figure 31:
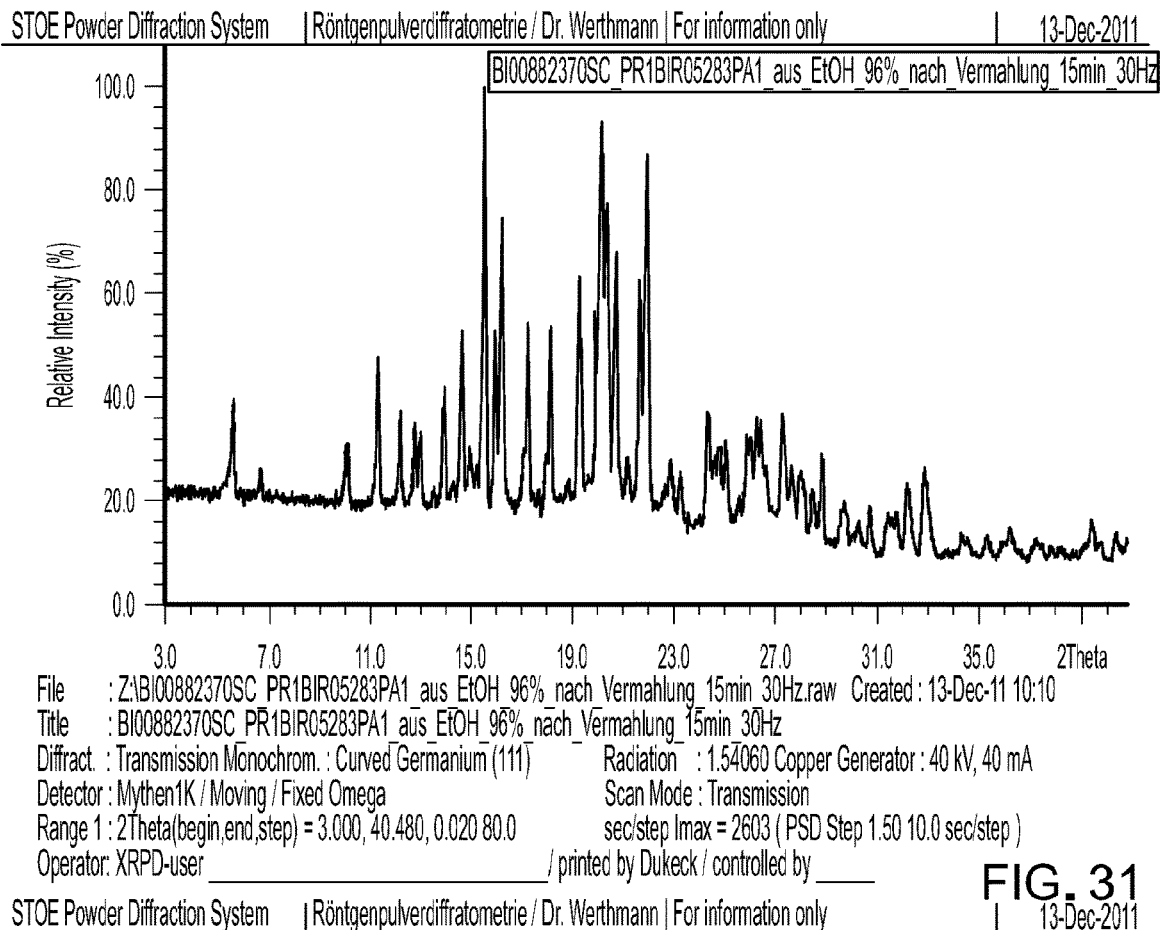
FIG. 31 is a plot of the XRPD of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt following milling in a swing mill for 10 min. at 30 rps.

FIG. 31 is a plot of the XRPD of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt following milling in a swing mill for 10 min. at 30 rps. The sample showed a slight decrease in crystallinity but no change in polymorphic form.

Figure 32:
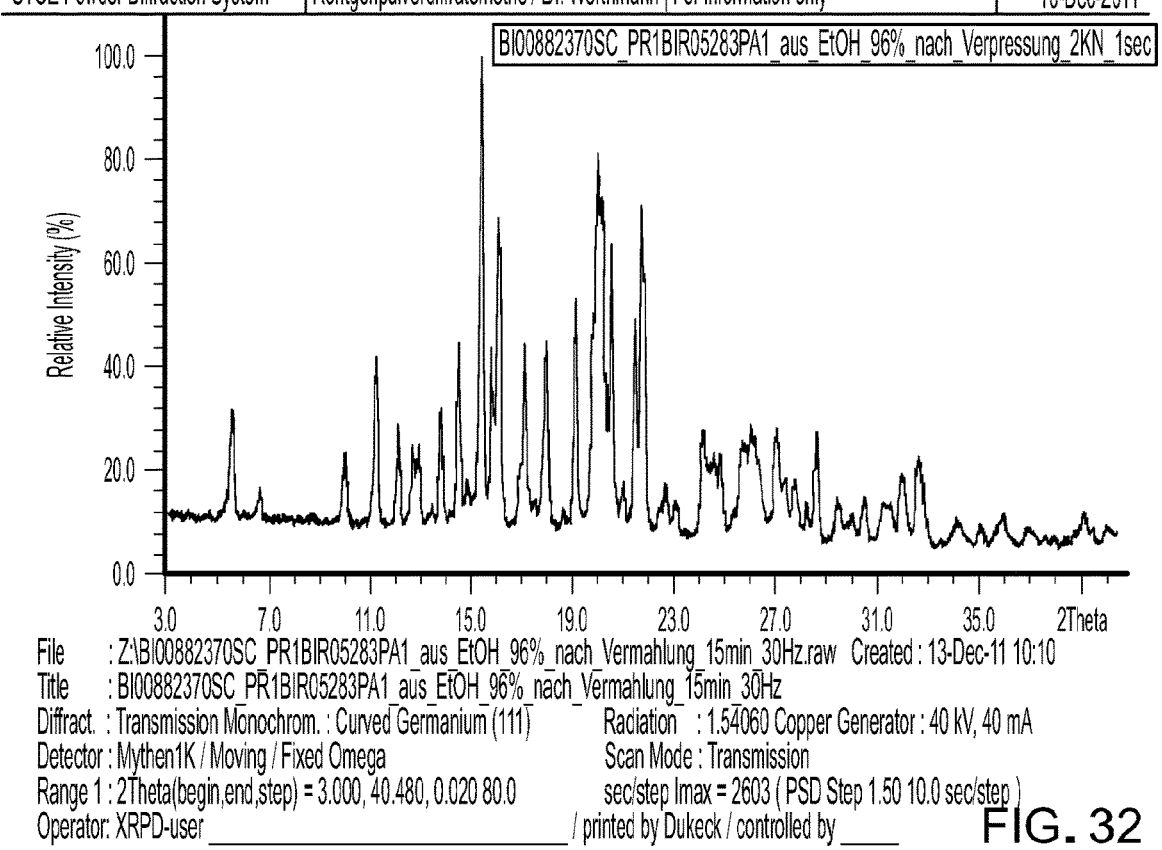
FIG. 32 is a plot of the XRPD of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt following compression at 2000 N for 1 s to a tablet (diameter-5 mm).

FIG. 32 is a plot of the XRPD of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt following compression at 2000 N for 1 s to a tablet (diameter-5 mm). The sample showed no significant decrease in crystallinity or change in polymorphic form.

Figure 33:
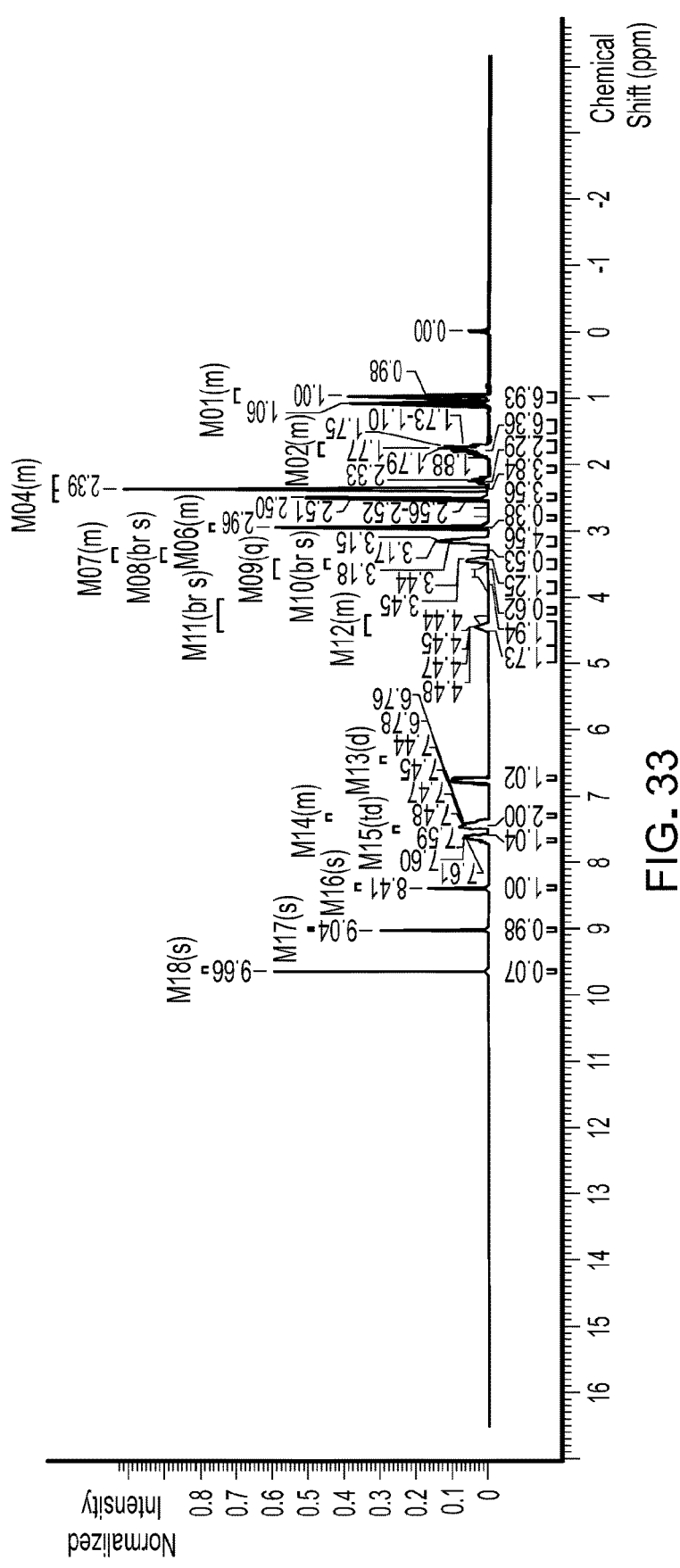
FIG. 33 is a $^1$H N.M.R. spectrum (400 MHz, DMSO-d6) of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt.

FIG. 33 is a $^1$H N.M.R. spectrum (400 MHz, DMSO-d6) of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt.

Figure 34:
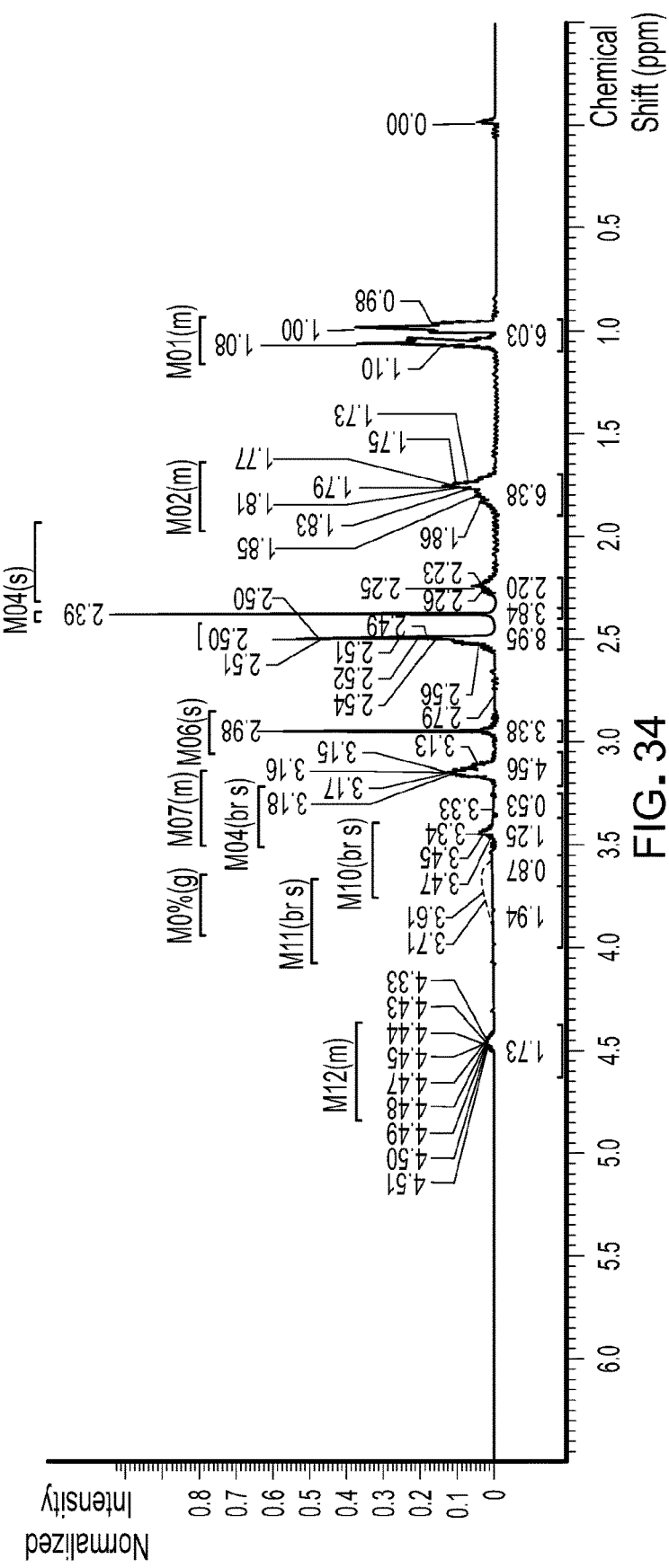
FIG. 34 is an inset on the aliphatic region (δ-0.5-6.0) of the $^1$H N.M.R. spectrum (400 MHz, DMSO-d6) of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt.

FIG. 34 is an inset on the aliphatic region (δ-0.5-6.0) of the $^1$H N.M.R. spectrum (400 MHz, DMSO-d6) of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt.

Figure 35:
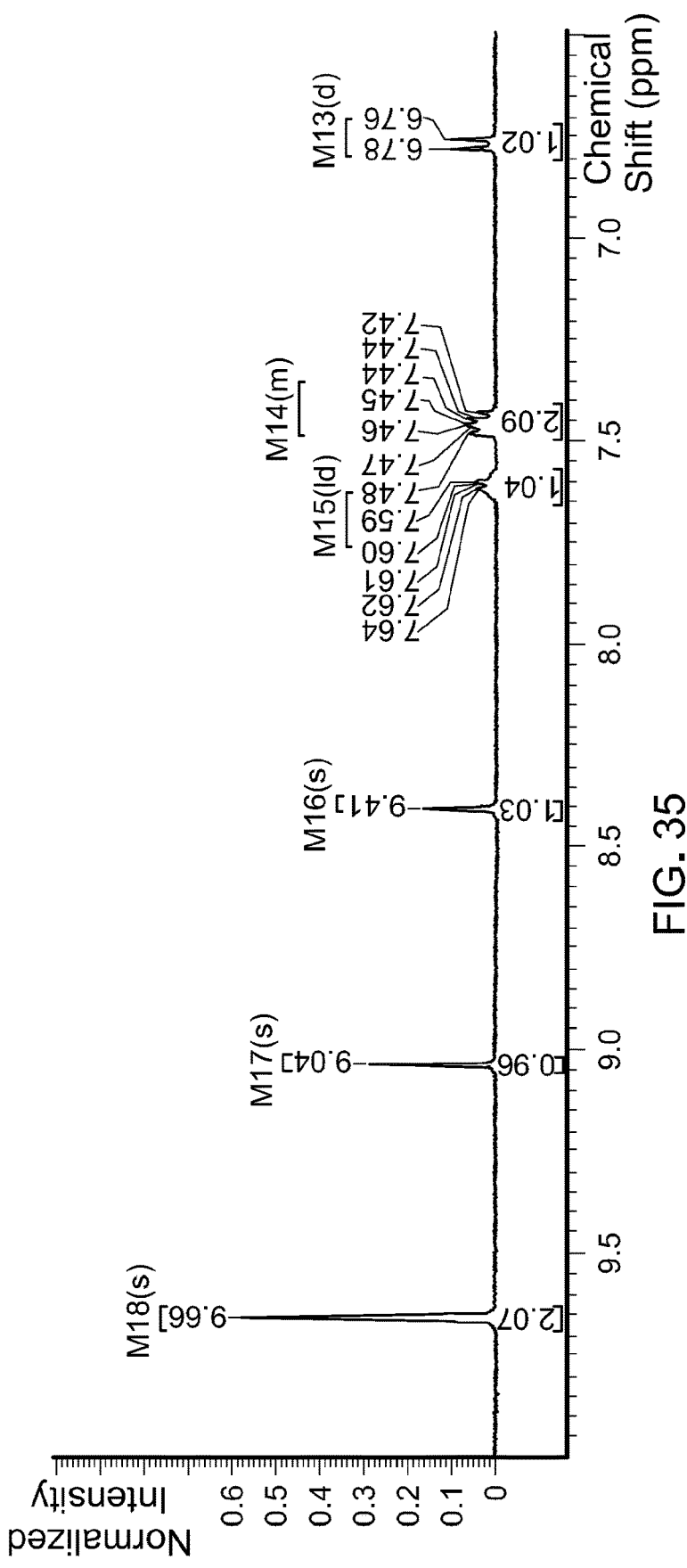
FIG. 35 is an inset on the aromatic region (δ 6.0-10.0) of the $^1$H N.M.R. spectrum (400 MHz, DMSO-d6) of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt.

FIG. 35 is an inset on the aromatic region (δ 6.0-10.0) of the $^1$H N.M.R. spectrum (400 MHz, DMSO-d6) of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt.

The solubility of N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt in various media was determined. The results are summarized in Table 10.

TABLE 10

Solubility of N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide Monosuccinate Salt In Various Media

| Medium | Solubility after 2 h (mg/mL) |
|---|---|
| Water | >2.00 |
| HCl (0.1M) | 0.20 |
| HCl (0.01M) | >0.05 |
| McIlvaine Buffer (pH 2.2) | >5.00 |
| McIlvaine Buffer (pH 3.0) | >5.00 |
| McIlvaine Buffer (pH 4.0) | >5.00 |
| McIlvaine Buffer (pH 4.5) | >5.00 |
| McIlvaine Buffer (pH 5.0) | >5.00 |
| Acetate Buffer (pH 5.0) | >5.00 |
| McIlvaine Buffer (pH 6.0) | 3.7 |
| McIlvaine Buffer (pH 6.8) | >5.00 |
| Phosphate Buffer (pH 6.8) | >5.00 |
| McIlvaine Buffer (pH 7.4) | 0.30 |
| Sorensen Buffer (pH 9.0) | 0.001 |
| Sorensen Buffer (pH 11) | 0.05 |
| 0.1M Citric acid | >5.00 |
| Simulated intestinal fluid (FaSSIF) | 0.003 |
| Simulated intestinal fluid (FeSSIF) | 0.40 |

The intrinsic dissolution rate of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt in various media was measured in media at various pH values. The results are summarized in Table 11.

TABLE 11

Intrinsic Dissolution Rate of N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide Monosuccinate Salt in Aqueous Media at pH 1.0-7.4

| pH of Medium | Intrinsic Dissolution Rate (µg/cm$^2$/min.) |
|---|---|
| 1.0 (0.1M HCl) | 201 |
| 2.2 | 6844 |
| 3.0 | 6605 |
| 4.5 | 2457 |
| 6.8 | 2533 |
| 7.4 | <1 |

Figure 36:
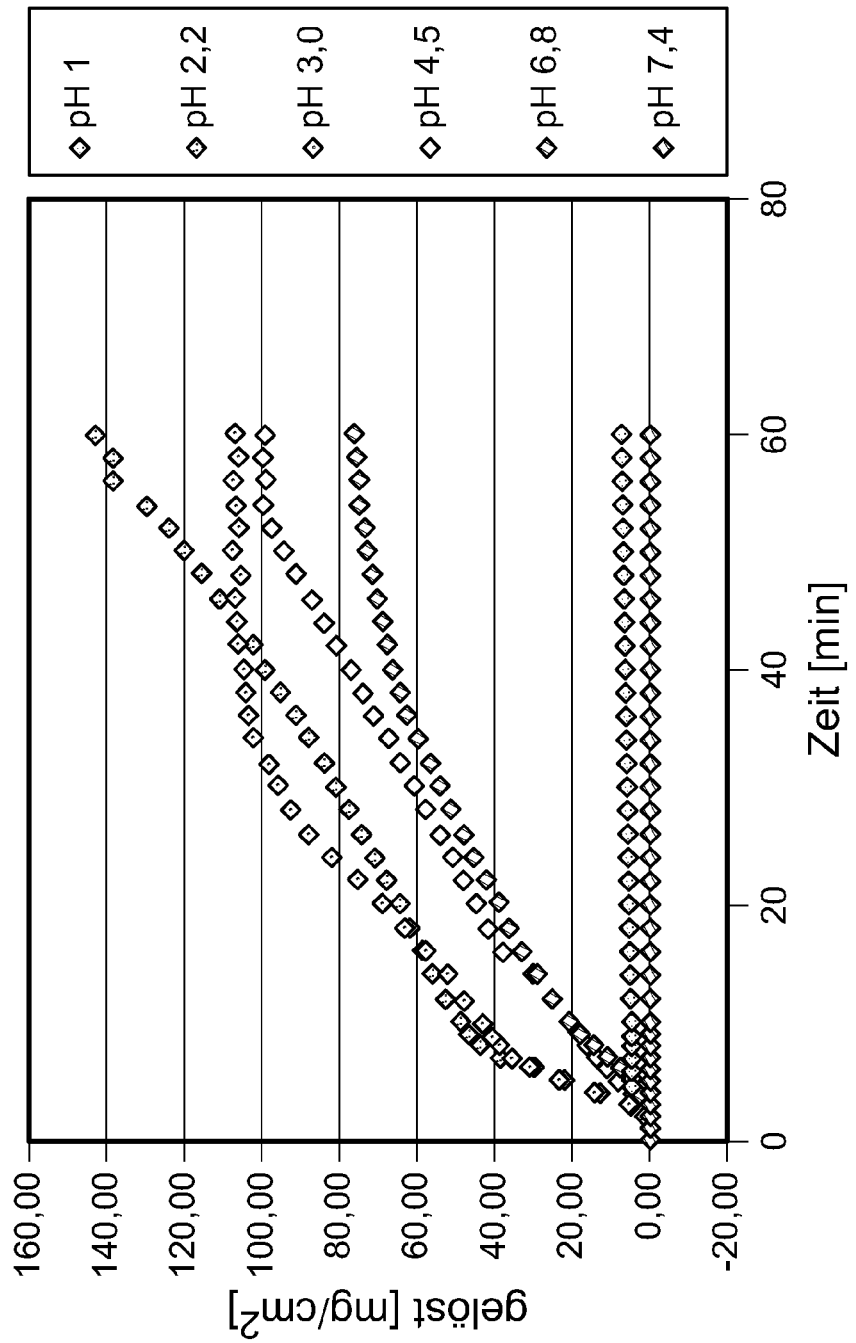
FIG. 36 is a plot showing the rate of dissolution of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt over 0-60 min. in aqueous medium at pH values of 1.0 to 7.4.
Figure 37B:
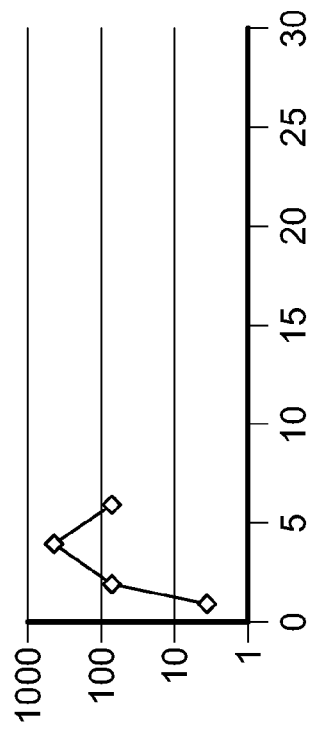
FIG. 37 is a plot of plasma concentration values with versus time following oral administration to rats of (A) N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt at 40 mg/kg; (B) N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt at 80 mg/kg; (C) N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt at 40 mg/kg; (D) N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt at 80 mg/kg.
Figure 37D:
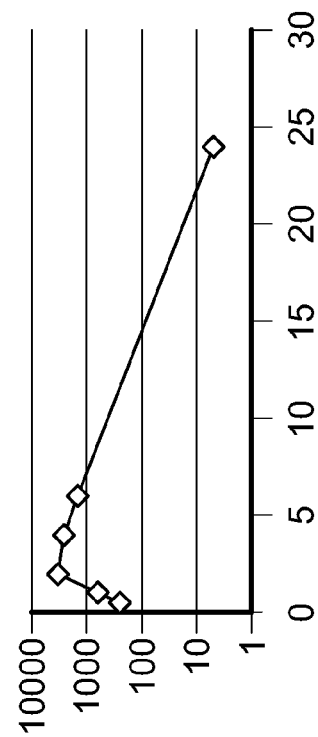
Figure 37A:
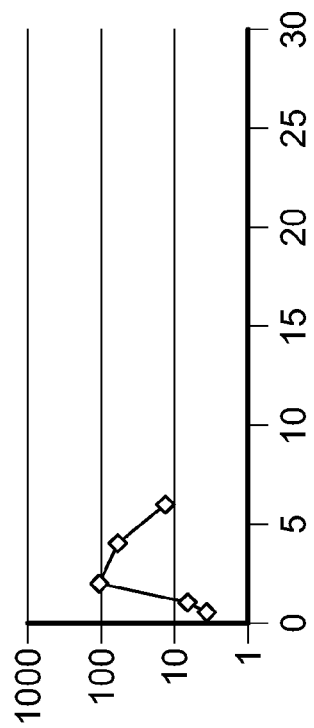
Figure 37C:
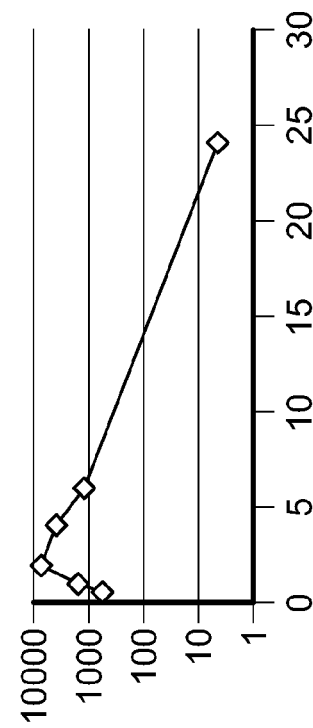

FIG. 36 is a plot showing the rate of dissolution of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt over 0-60 min. in aqueous medium at pH values of 1.0 to 7.4.

Surprisingly, the solubility of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt was substantially higher in a number of media tested than the solubility of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt. The intrinsic dissolution rate of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt was also substantially higher than the intrinsic dissolution rate of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt.

Pharmacokinetics of N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide Monohydrochloride Salt and N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide Monosuccinate Salt in Rat The pharmacokinetics of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide hydrochloride salt and N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide hydrochloride salt were measured following oral administration at 40 mg and 80 mg (dose calculated as the free base) to HsdHan: WIST Norway rats. Each salt was administered to 3 animals. Results are shown in Table 12.

TABLE 12

Mean Plasma Concentrations Following Oral Administration of N-(3-(5-(((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide Monohydrochloride Salt or N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide Monosuccinate Salt to Norway Rats (Average of n = 3 ± Standard Deviation)

| | Blood Plasma Concentrations (nM) | | | |
|---|---|---|---|---|
| Time | Monohydrochloride Salt (40 mg/kg) | Monohydrochloride Salt (80 mg/kg) | Monosuccinate Salt (40 mg/kg) | Monosuccinate Salt (80 mg/kg) |
| 0.5 | 3.53 (±1.76) | | 523 (±303) | 274 (±198) |
| 1.0 | 6.56 (±5.7) | 3.69 | 1320 (±691) | 638 (±713) |
| 2.0 | 107 (±124) | 69.9 (±23.3) | 6550 (±975) | 3380 (±2720) |
| 4.0 | 60.9 (±22.3) | 419 (±32.6) | 3860 (±671) | 2620 (±1640) |
| 6.0 | 13.3 (±8.45) | 69 (±12.8) | 1140 (±299) | 1420 (±1300) |
| 24.0 | | | 3.98 (±0.317) | 5.09 (±198) |
| PK Parameters | | | | |
| AUD Range | 0-6 h | 0-6 h | 0-24 h | 0-24 h |
| AUD (nM · h) | 312 (±211) | 1040 (±51.1) | 30300 (±3120) | 25100 (±20900) |
| $C_{max}$ (nM) | 123 (±107) | 419 (±32.6) | 6550 (±975) | 3520 (±2590) |
| $T_{max}$ (h) | 3.3 (±1.2) | 4.0 (±0.0) | 2.0 (±0.0) | 2.7 (±1.2) |
| Oral Bioavailability | 1% | | 50% | |

The data show that exposure values were substantially higher for the monosuccinate salt than for the monohydrochloride salt. Furthermore, the oral bioavailability at 40 mg/kg dose was only 1% for the monohydrochloride salt, compared with 50% for the monosuccinate salt.

FIG. 37 is a plot of plasma concentration values with versus time following oral administration to rats of (A) N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt at 40 mg/kg; (B) N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monohydrochloride salt at 80 mg/kg; (C) N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt at 40 mg/kg; (D) N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt at 80 mg/kg.

Scale-Up Preparation of N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide Monosuccinate Salt (Form A)

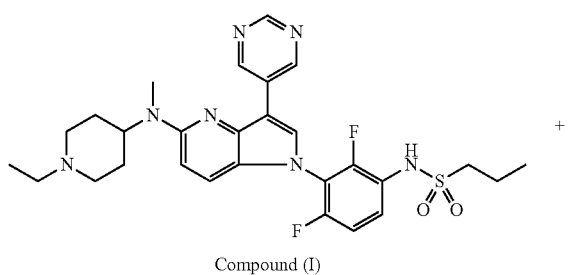

Compound (I)

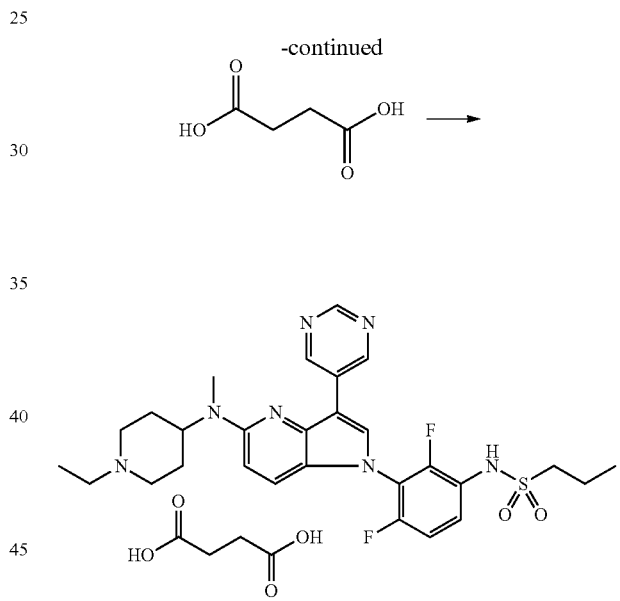

Methanol (11.26 kg) and compound (I) (1.58 kg, 2.63 mol) were added into a reactor, and the resulting mixture was stirred and heated to 60-70° C. until the solid was dissolved. Succinic acid (393 g, 3.16 mol) was added into the mixture. Stirring at 60-70° C. was continued for 0.5-1 h, then the solution was cooled to 10~25° C. Seed crystals of Form A of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt (3 g) were added into the mixture, and stirring was continued for an additional 1 h to fully crystallize the product. The mixture was then cooled to 0-10° C. and held for 3-4 h. The precipitated product was isolated by filtration, and washed with chilled methanol. The solid was dried under vacuum at 45-50° C. to provide Form A of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt (1.53 kg, yield 80.2%).

Further Salt Form Characterization of N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide Monosuccinate Salt Further experiments were performed to characterize Form A of N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt. During the characterization, several additional forms were identified.

Additional General Methods

For the studies described below, unless stated otherwise, instruments and methods used were as described below.

X-Ray Powder Diffraction

XRPD analysis was performed using PANalytical Empyrean and X'Pert3 X-ray powder diffractometers were used using the parameters listed in Table 13.

TABLE 13

XPRD Parameters

| Parameters | Empyrean (Reflection Mode) | X' Pert3 (Reflection Mode) |
|---|---|---|
| X-Rays | Cu, Kα, Kα1: 1.540598 Å; Kα2: 1.544426 Å; Kα2/Kα1 intensity ratio: 0.5 | Cu, Kα, Kα1: 1.540598 Å; Kα2: 1.544426 Å; Kα2/Kα1 intensity ratio: 0.5 |
| X-Ray Tube Setting | 45 kV, 40 mA | 45 kV, 40 mA |
| Divergence Slit | Automatic | 1/8° |
| Scan Mode | Continuous | Continuous |
| Scan Range (°2θ) | 3°-40° | 3°-40° |
| Step Range (°2θ) | 0.0167° | 0.0263° |
| Scan Step Time (s) | 33.02 | 46.665 |
| Test Time (min.) | ~10 min. | ~5 min. |

Thermogravimetric Analysis and Differential Scanning Calorimetry

TGA data were collected using a TA Q500/Q5000/5500 TGA from TA Instruments. DSC was performed using a TA Q200/Q2000/2500 DSC from TA Instruments. Detailed parameters used are listed in Table 14

TABLE 14

XPRD Parameters

| Parameters | TGA | DSC |
|---|---|---|
| Method | Ramp | Ramp |
| Sample Pan | Aluminum, open | Aluminum, crimped |
| Temperature | rt-350° C. | 25-250° C. |
| Heating Rate | 10° C./min. | 10° C./min. |
| Purge Gas | Nitrogen | Nitrogen |

Dynamic Vapor Sorption

DVS was measured via a SMS (Surface Measurement Systems) DVS Intrinsic. The relative humidity at 25° C. was calibrated against the deliquescence point of LiCl, $Mg(NO_3)_2$ and KCl. Parameters for DVS testing are listed in Table 15.

TABLE 15

DVS Parameters

| Parameters | DVS |
|---|---|
| Temperature | 25° C. |
| Sample Size | 10-200 mg |
| Gas and Flow Rate | Nitrogen, 200 mL/min. |
| dm/dt | 0.002%/min. |
| Minimum dm/dt stability duration | 10 min. |
| Maximum equilibration time | 180 min. |
| RH range | 0% RH to 95% RH to 0% RH |
| RH step size | 10% RH from 0% RH to 90% RH 5% RH from 90% RH to 95% RH |

Nuclear Magnetic Resonance $^1$H solution NMR was performed using a Bruker 400 MHz NMR Spectrometer using DMSO-d6 or deuterated methanol as the solvent.

Polarized Light Microscopy

PLM images were captured using an Axio Lab. A1 upright microscope with ProgRes® CT3 camera at rt.

HPLC

HPLC analyses were performed using an Agilent 1260 HPLC was utilized. Chromatographic conditions are listed in Tables 16 and 17.

TABLE 16

HPLC Parameters for Purity Testing

| HPLC | Agilent 1260 with DAD Detector | |
|---|---|---|
| Column | Gemini C18 110 A, 250 × 4.6 mm, 5 μm. | |
| Mobile Phase | A: 0.1% TFA in $H_2O$; B: 0.1% in MeCN | |
| Gradient Table | Time (min.) | % B |
| | 0.00 | 20 |
| | 45.00 | 60 |
| | 45.01 | 20 |
| | 60.00 | 20 |
| Run Time | 60.0 min. | |
| Post Time | 0.0 min. | |
| Flow Rate | 1.0 mL/min. | |
| Injection Volume | 10 μL | |
| Detector wavelength | UV at 234 nm | |
| Column Temperature | 30° C. | |
| Sampler Temperature | rt | |
| Diluent | MeCN/$H_2O$ (20:80 v/v) | |

TABLE 17

HPLC Parameters for Solubility Testing

| HPLC | Agilent 1260 with DAD Detector | |
|---|---|---|
| Column | Gemini C18 110 A, 250 × 4.6 mm, 5 μm. | |
| Mobile Phase | A: 0.1% TFA in $H_2O$; B: 0.1% in MeCN | |
| Gradient Table | Time (min.) | % B |
| | 0.00 | 20 |
| | 5.00 | 70 |
| | 5.10 | 20 |
| | 10.00 | 20 |
| Run Time | 10.0 min. | |
| Post Time | 0.0 min. | |
| Flow Rate | 1.0 mL/min. | |
| Injection Volume | 10 μL | |

TABLE 17-continued

HPLC Parameters for Solubility Testing

| | |
|---|---|
| Detector wavelength | UV at 234 nm |
| Column Temperature | 30° C. |
| Sampler Temperature | rt |
| Diluent | MeCN |

The polymorph screening experiments were performed using anti-solvent addition, reverse anti-solvent addition, solid vapor diffusion, solution vapor diffusion, slurry, slow evaporation, slow cooling and polymer induced crystallization techniques. In addition to Form A, four new succinate forms were identified, which were assigned as succinate Forms C, D, E and F. All of the crystal forms were characterized by X-ray powder diffraction (XRPD), thermogravimetric analysis (TGA), differential scanning calorimeter (DSC), proton nuclear magnetic resonance ($^1$H NMR) and HPLC. Two of the additional forms were anhydrates, one was a solvate, and another was not characterized due to limited amounts of sample and difficulties in re-preparation. Forms C, D, E and F of the succinate salt all had inferior properties to Form A in terms of stability and other properties.

Further Characterization of Form A of N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt The sample of Form A of N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt was characterized further.

XRPD results for two batches of Form A of N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt are shown in FIG. 38.

TGA and DSC analysis results are shown in FIG. 39. In the TGA curve of succinate Form A, a weight loss of 1.9% up to 140° C. was observed on the. On the DSC curve, a step endothermic signal at 159.5° C. (onset) was observed before a sharp endotherm at 181.3° C. (onset).

Figure 40:
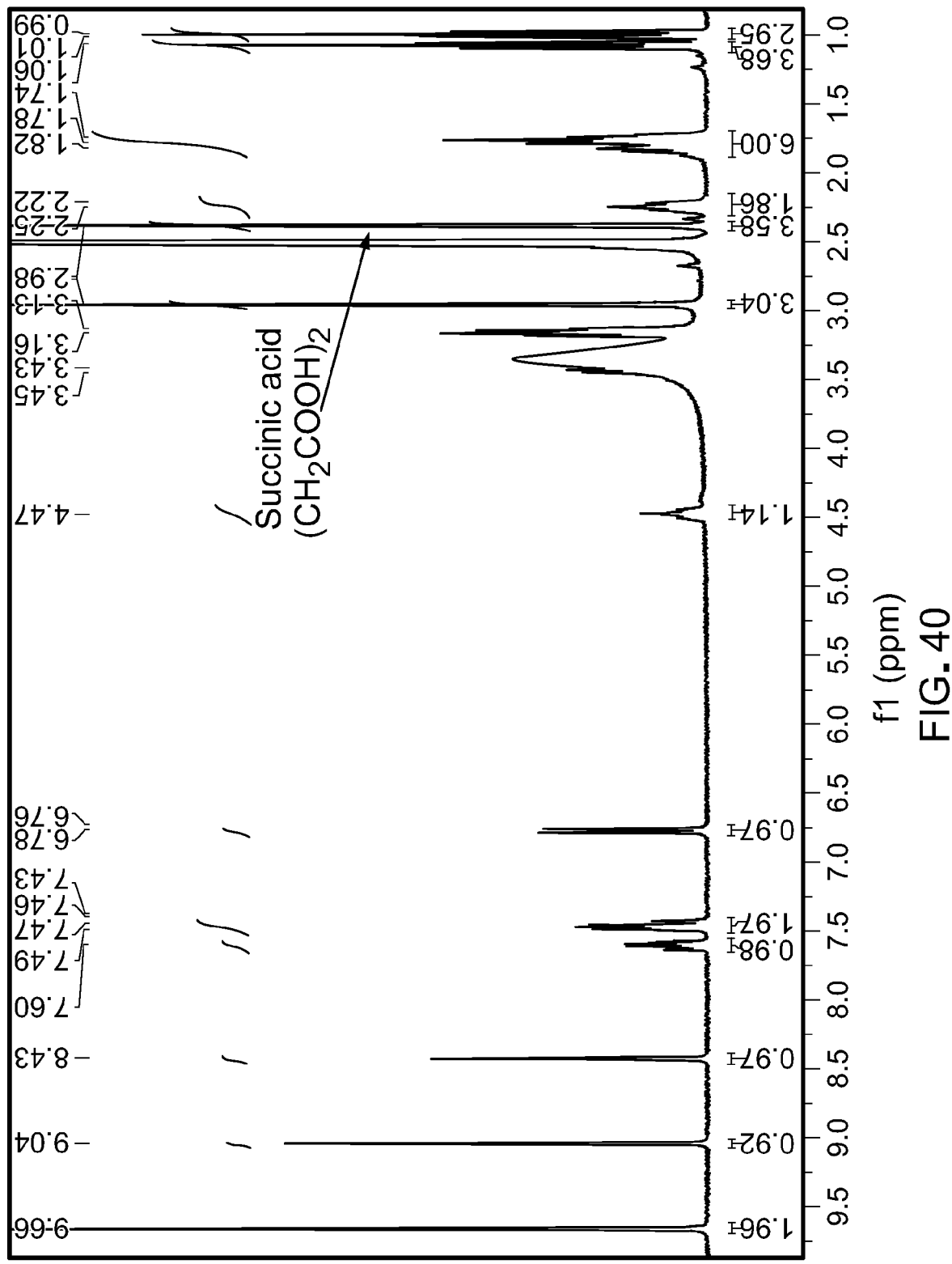
FIG. 40 is a $^1$H N.M.R. spectrum (DMSO-d6) of Form A of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt.
Figure 41:
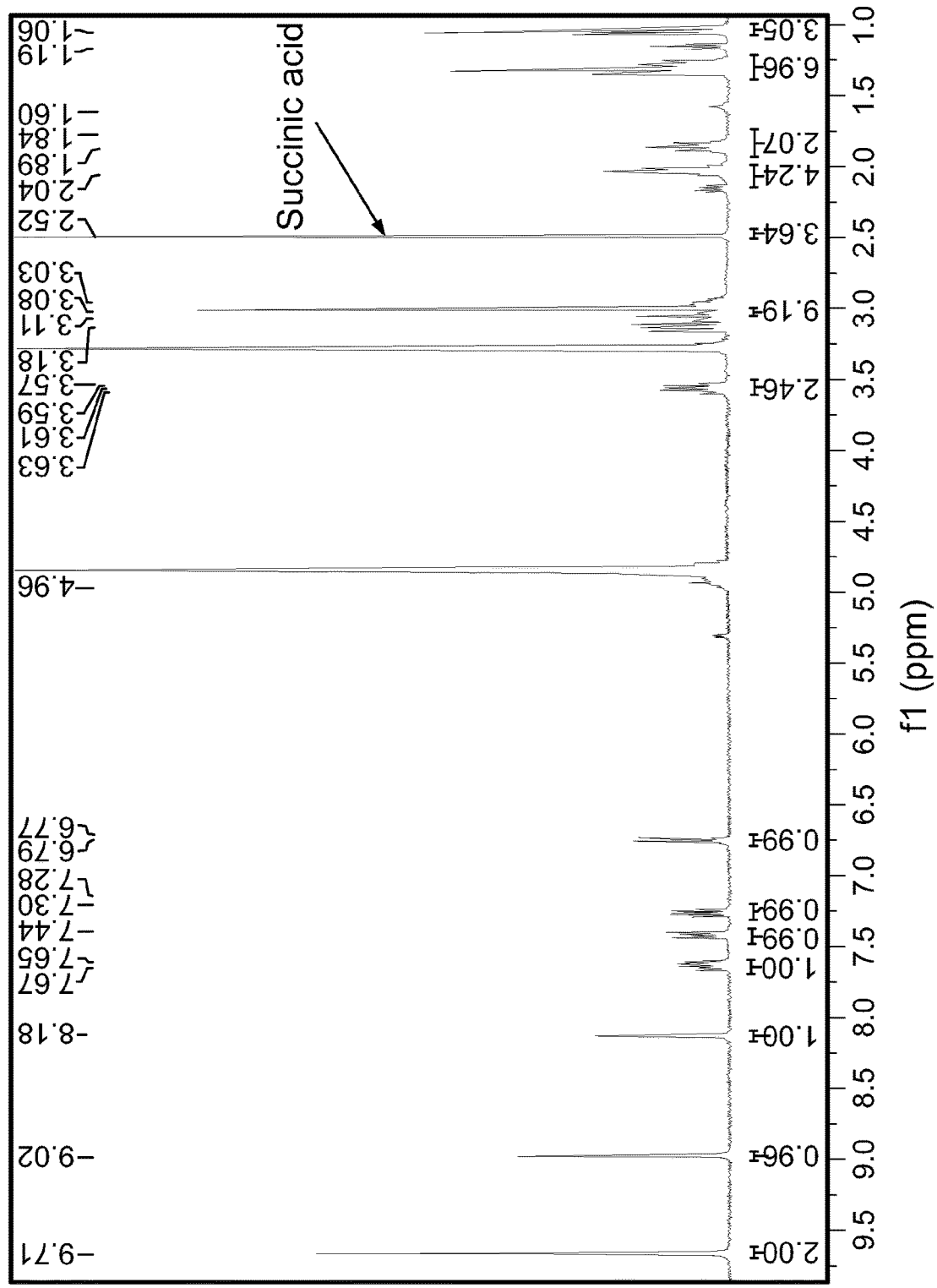
FIG. 41 is a $^1$H N.M.R. spectrum (deuterated methanol) of Form A of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt.
Figure 42:
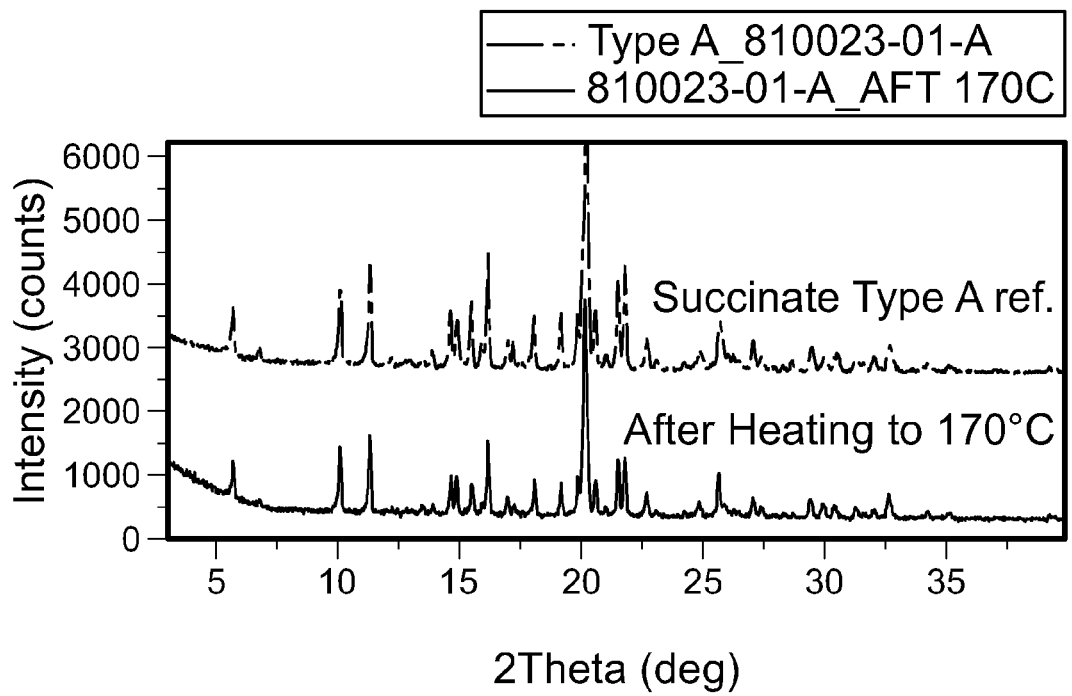
FIG. 42 is a pair of plots of the XRPD of Form A of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt before and after heating to 170° C. and cooling to room temperature.
Figure 43:
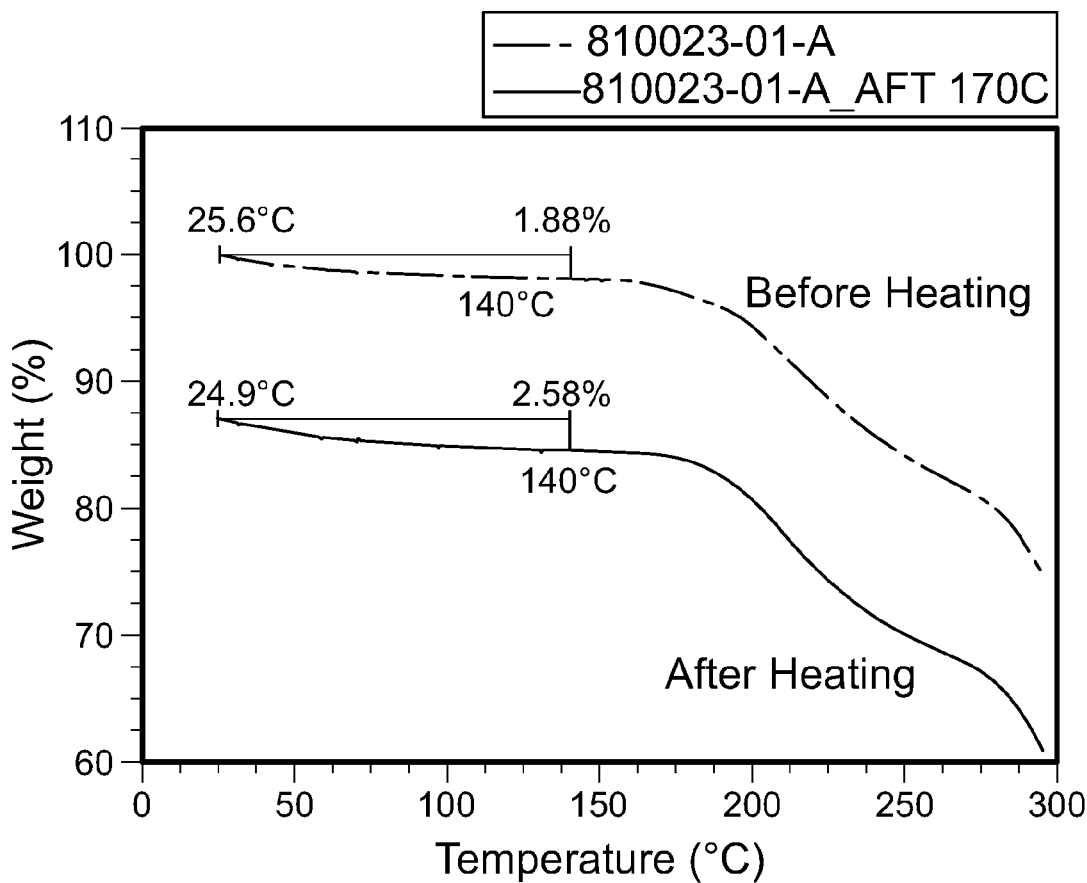
FIG. 43 is a pair of plots of TGA of Form A of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt before and after heating to 170° C. and cooling to room temperature.
Figure 44:
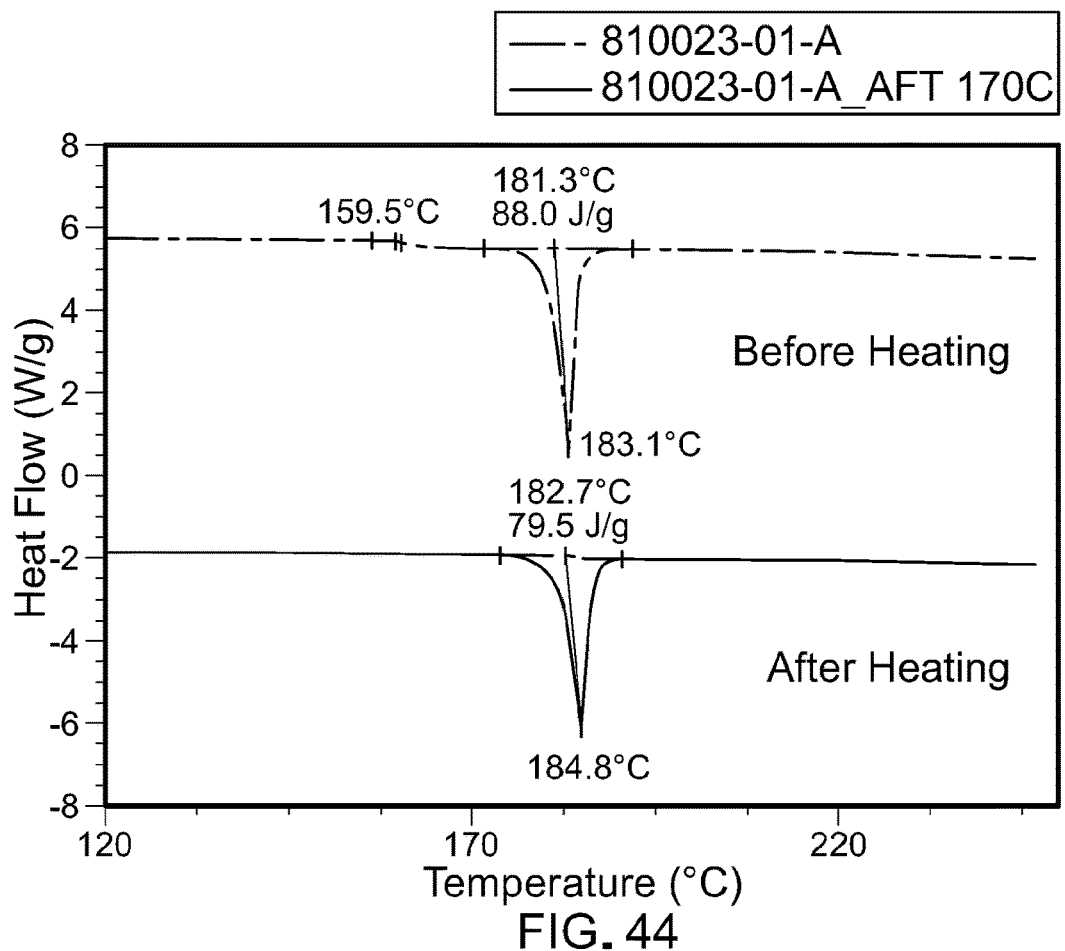
FIG. 44 is a pair of plots of DSC of Form A of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt before and after heating to 170° C. and cooling to room temperature.
Figure 45:
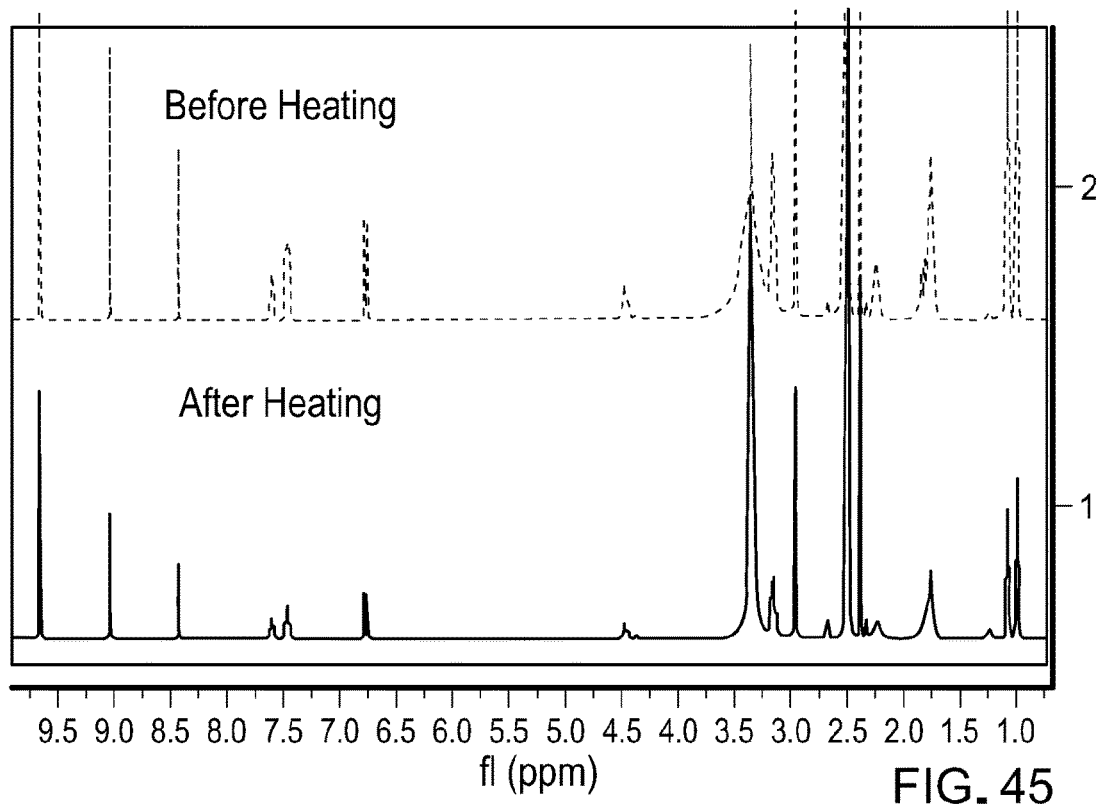
FIG. 45 is a pair of $^1$H N.M.R. spectra (DMSO-d6) of Form A of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt before and after heating to 170° C. and cooling to room temperature.

$^1$H NMR spectra are shown in FIG. 40 (DMSO-d6 as solvent) and FIG. 41 (deuterated MeOH as solvent), and the molar ratio of succinic acid/free base was determined to be 0.9:1. The molar ratio of acid/free base in succinate Type A calculated using the peas integration at 2.38 ppm (integral 3.58, hydrogen atoms of succinate, 4H) and at 1.78 ppm (integral 6.00, hydrogen atoms of free base, 6H).

HPLC analysis confirmed the purity of a sample of succinate Form A (810023-01-A) was 99.5% (area).

Further XRPD, TGA, DSC and $^1$H NMR analyses were performed after heating succinate Form A to 170° C. and then cooling to room temperature. The results were shown in FIG. 42 to FIG. 45.

After heating, XRPD (FIG. 42) confirmed that the crystalline form was still succinate Type A.

In the TGA curve (FIG. 43), a weight loss of 2.6% up to 140° C. was observed, which was likely to be caused by the surface adsorbed moisture as the heated sample was exposed to air before further TGA test. The TGA analysis was performed about 4.5 h after the heating experiment. The weight loss of the heated sample (2.6%) was higher than that initially observed (1.9%), indicating the hygroscopicity of succinate Type A may increase slightly after heat treatment.

In the DSC curve (FIG. 44), only one endotherm at 182.7° C. (onset) was observed.

In the NMR analysis (FIG. 45), the molar ratio of succinic acid/free base was still observed to be 0.9:1.

Based on the above results, succinate Type A was identified as an anhydrate.

Equilibrium Solubility

Equilibrium solubility of Form A in water was measured at room temperature. The solid was suspended into H$_2$O (~800 rpm) at rt. After 24 h., the suspension was centrifuged (10000 rpm, 5 min) followed by filtration (0.45 μm PTFE membrane). The supernatant (first few drops were discarded) was analyzed by HPLC and the pH was measured. The residual solid was analyzed by XRPD. The measured solubility of the Form A was 14.3 mg/mL, respectively.

Figure 46:
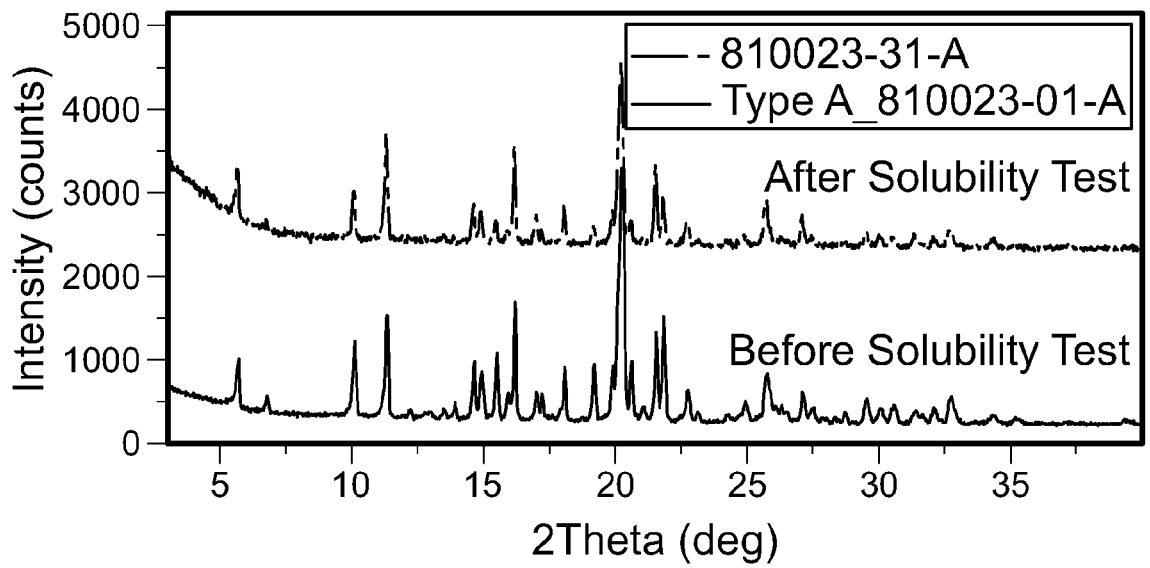
FIG. 46 is a set of XPRD plots showing that the form of Form A of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt does not change during equilibrium solubility testing.

XRPD analysis showed no form change for Form A (FIG. 46) during the dissolution experiment.

Solid State Stability

Samples of Form A of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt were stored under at 80° C. for one day, at 25° C. under 60% RH and at 40° C. under 75% RH for one week. All the samples were then characterized using XRPD and HPLC, with the results summarized in Table 18.

Figure 47:
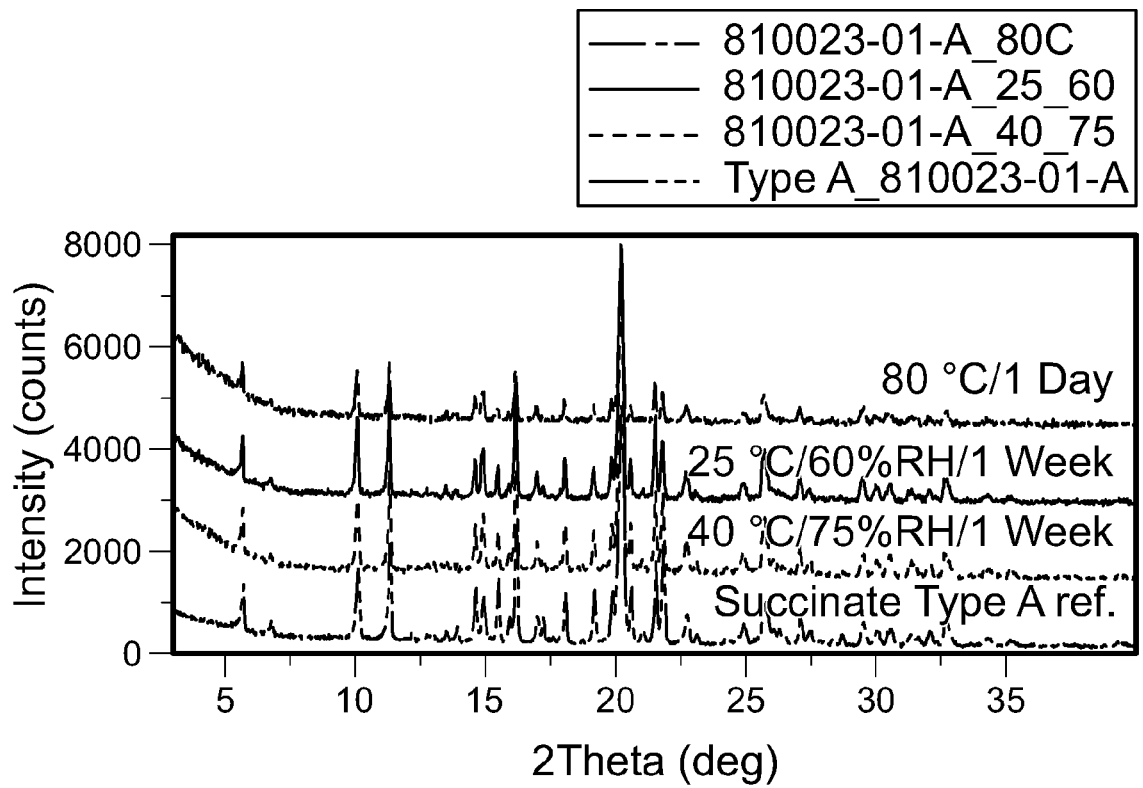
FIG. 47 is a set of XPRD plots showing stability of Form A of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt following storage under various conditions.

No form change or HPLC purity decrease were observed for Form A under any of the conditions, indicating that Form A of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt possesses good solid state stability. XRPD analysis results are shown in FIG. 47.

TABLE 18

Summary of Solid State Stability Evaluation of Form A of N-(3-(5-((1-Ethylpiperidin-4-yl)(methyl)amino)-3-(pyrimidin-5-yl)-1H-pyrrolo[3,2-b]pyridin-1-yl)-2,4-difluorophenyl)propane-1-sulfonamide Monosuccinate Salt

| | Conditions: | | | | | |
|---|---|---|---|---|---|---|
| | 80% C/1 day | | 25° C., 60% RH/1 week | | 25° C., 60% RH/1 week | |
| Initial Purity: | Purity (% of Initial) | Form Change | Purity (% of Initial) | Form Change | Purity (% of Initial) | Form Change |
| 99.5% | 99.9 | No | 100.0 | No | 100.1 | No |

Hygroscopicity

To investigate the solid form stability as a function of humidity, a DVS isotherm plot of Form A of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt was collected at 25° C. between 0 and 95% RH.

Figure 48:
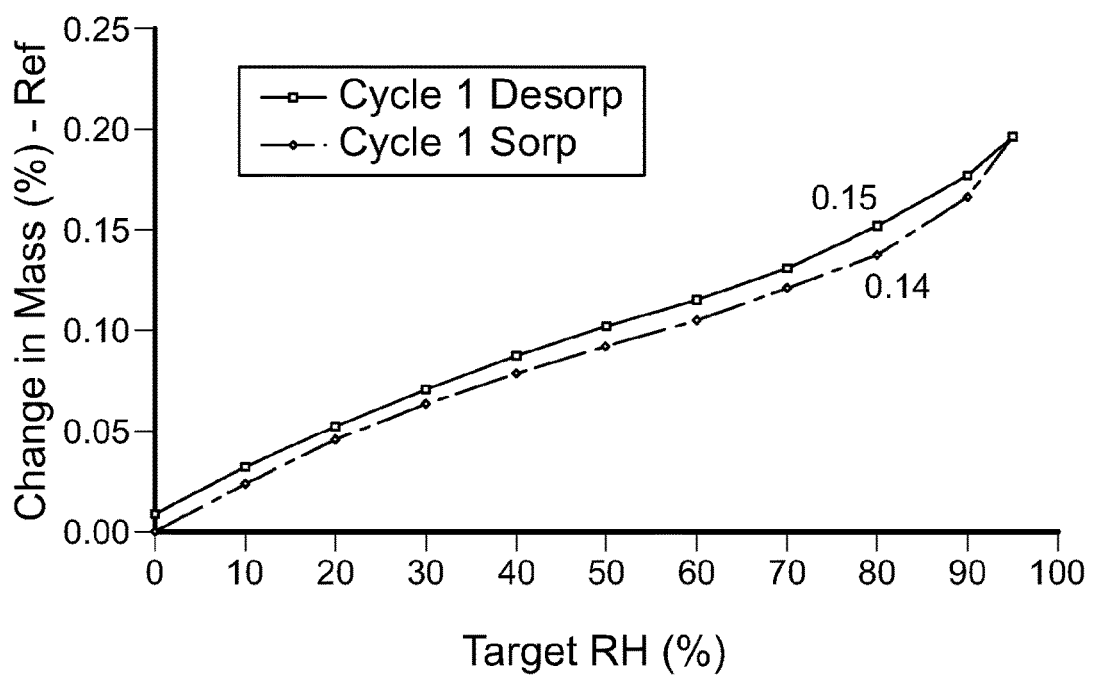
FIG. 48 is a set of DVS isotherm plots showing the low hygroscopicity of Form A of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt.

The DVS plot of Form A of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt show in FIG. 48 indicated 0.14% water uptake at 25° C./80% RH, indicating that Form A is non-hygroscopic.

Figure 49:
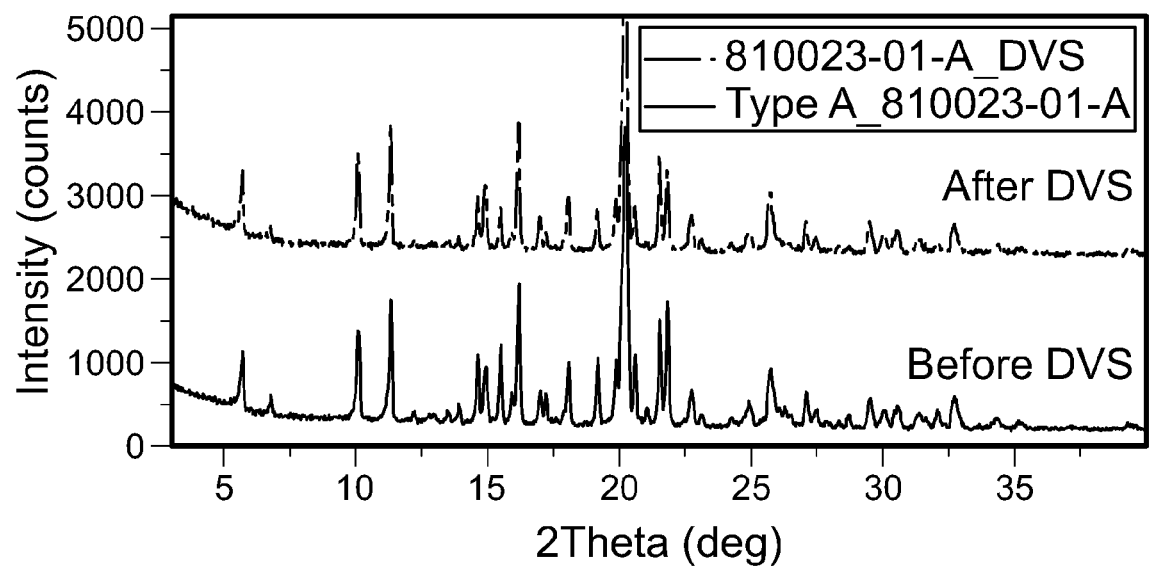
FIG. 49 is a pair of XPRD plots showing that Form A of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt does not change form after DVS testing.

XRPD analysis as shown in FIG. 49 showed that the DVS analysis did not result in any form change for Form A of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt.

Polarized Light Microscopy

Figure 50:
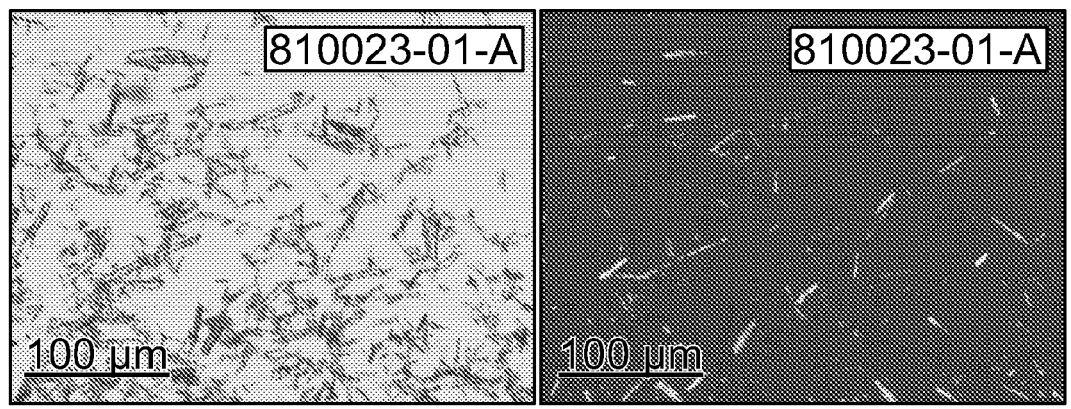
FIG. 50 is a pair of polarized light microscopy images of Form A of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt.

PLM images were recorded to study the morphology of Form A of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt. As shown in FIG. 50, Form A is composed of rod-like crystals.

CONCLUSION

Based on all the above results, Form A of N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt was found to be a stable, non-hygroscopic crystalline form that was suitable for pharmaceutical use.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. Crystalline N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide monosuccinate salt, having an X-ray powder diffraction pattern comprising at least one of the following peaks, in terms of 2θ: 15.4°±0.5°; 20.0°±0.5°; and 21.8°±0.5°.

2. The crystalline salt of claim 1 which is substantially anhydrous and non-solvated.

3. The crystalline salt of claim 1, having an X-ray powder diffraction pattern comprising a peak, in terms of 2θ, at 15.4°±0.5°.

4. The crystalline salt of claim 1, having an X-ray powder diffraction pattern comprising the following peaks, in terms of 2θ: 15.4°±0.5°; 20.0°±0.5°; and 21.8°±0.5°.

5. The crystalline salt of claim 1 having an X-ray powder diffraction pattern substantially as shown in FIG. 10, FIG. 26, or FIG. 38.

6. The crystalline salt of claim 1 having a differential scanning calorimetry thermogram (DSC) substantially as shown in FIG. 11, FIG. 27, or FIG. 39.

7. The crystalline salt of claim 1 having a thermogravimetric analysis (TGA) substantially as shown in FIG. 12, FIG. 28 or FIG. 39.

8. A composition comprising the crystalline salt of claim 1.

9. The composition of claim 8 wherein the composition comprises at least one pharmaceutically acceptable carrier.

10. The composition of claim 9, wherein the composition is a tablet.

11. A process for preparing the crystalline salt of claim 1 comprising reacting N-(3-(5-((1-ethylpiperidin-4-yl)(methyl)amino)-3-(pyrimidin-5-yl)-1H-pyrrolo[3,2-b]pyridin-1-yl)-2,4-difluorophenyl)propane-1-sulfonamide with one equivalent of succinic acid.

12. The process of claim 11 further comprising crystallizing the salt from a $C_{1-4}$ alcohol or aqueous $C_{1-4}$ alcohol or ethyl acetate.

13. The process of claim 11 further comprising crystallizing the salt from ethanol, isopropanol, aqueous ethanol, aqueous isopropanol, or ethyl acetate.

14. A method of treating a cancer in a patient, comprising administering to the patient a therapeutically effective amount of a crystalline salt of claim 1, wherein the cancer is breast cancer, prostate cancer, colon cancer, endometrial cancer, brain cancer, bladder cancer, skin cancer, uterus cancer, ovarian cancer, lung cancer, pancreatic cancer, renal cancer, gastric cancer, hematological cancer, malignant melanoma, thyroid cancer, colorectal cancer, or biliary tract cancer.

15. The method of claim 14, wherein the cancer is lung cancer.

16. The method of claim 14, wherein the cancer is malignant melanoma.

17. The method of claim 14, wherein the cancer is thyroid cancer.

18. The method of claim 14, wherein the cancer is colorectal cancer.

19. The method of claim 14, wherein the cancer is biliary tract cancer.

20. The method of claim 14, wherein the cancer is non-small cell lung cancer.

* * * * *

UNITED STATES PATENT AND TRADEMARK OFFICE
CERTIFICATE OF CORRECTION

| | |
|---|---|
| PATENT NO. | : 11,306,086 B2 |
| APPLICATION NO. | : 16/759187 |
| DATED | : April 19, 2022 |
| INVENTOR(S) | : Werthmann et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 57 days.

Signed and Sealed this
Thirteenth Day of December, 2022

Katherine Kelly Vidal
*Director of the United States Patent and Trademark Office*